US012617858B2

(12) United States Patent
Tuohy et al.

(10) Patent No.: US 12,617,858 B2
(45) Date of Patent: May 5, 2026

(54) ANTI-MÜLLERIAN HORMONE RECEPTOR 2 ANTIBODIES AND METHODS OF USE

(71) Applicant: The Cleveland Clinic Foundation, Cleveland, OH (US)

(72) Inventors: Vincent K. Tuohy, Cleveland, OH (US); Suparna Mazumder, Cleveland, OH (US); Justin M. Johnson, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 897 days.

(21) Appl. No.: 17/792,195

(22) PCT Filed: Jan. 29, 2021

(86) PCT No.: PCT/US2021/015910

§ 371 (c)(1),
(2) Date: Jul. 12, 2022

(87) PCT Pub. No.: WO2021/155295

PCT Pub. Date: Aug. 5, 2021

(65) Prior Publication Data

US 2023/0078601 A1     Mar. 16, 2023

Related U.S. Application Data

(60) Provisional application No. 62/968,840, filed on Jan. 31, 2020.

(51) Int. Cl.
| | |
|---|---|
| *C07K 16/28* | (2006.01) |
| *A61K 9/107* | (2006.01) |
| *A61K 39/00* | (2006.01) |
| *A61K 39/39* | (2006.01) |
| *A61K 39/395* | (2006.01) |
| *A61K 45/06* | (2006.01) |
| *A61P 35/00* | (2006.01) |
| *A61P 37/04* | (2006.01) |

(52) U.S. Cl.
CPC .......... *C07K 16/2869* (2013.01); *A61K 9/107* (2013.01); *A61K 39/001102* (2018.08); *A61K 39/39* (2013.01); *A61K 39/3955* (2013.01); *A61K 45/06* (2013.01); *A61P 35/00* (2018.01); *A61P 37/04* (2018.01); *A61K 2039/545* (2013.01); *A61K 2039/55566* (2013.01); *A61K 2039/55583* (2013.01); *C07K 2317/21* (2013.01); *C07K 2317/34* (2013.01); *C07K 2317/565* (2013.01); *C07K 2317/73* (2013.01); *C07K 2317/732* (2013.01); *C07K 2317/734* (2013.01); *C07K 2317/76* (2013.01); *C07K 2317/77* (2013.01); *C07K 2317/92* (2013.01)

(58) Field of Classification Search
CPC ........... C07K 16/2869; C07K 2317/21; C07K 2317/34; C07K 2317/565; C07K 2317/73; C07K 2317/732; C07K 2317/734; C07K 2317/76; C07K 2317/77; C07K 2317/92; A61K 9/107; A61K 39/001102; A61K 39/39; A61K 39/3955; A61K 45/06; A61K 2039/545; A61K 2039/55566; A61K 2039/55583; A61K 2039/505; A61P 35/00; A61P 37/04
See application file for complete search history.

(56) References Cited

U.S. PATENT DOCUMENTS

| | | | |
|---|---|---|---|
| 4,816,567 | A | 3/1989 | Cabilly et al. |
| 5,500,362 | A | 3/1996 | Robinson et al. |
| 5,530,101 | A | 6/1996 | Queen et al. |
| 5,565,332 | A | 10/1996 | Hoogenboom et al. |
| 5,571,894 | A | 11/1996 | Wels et al. |
| 5,585,089 | A | 12/1996 | Queen et al. |
| 5,587,458 | A | 12/1996 | King et al. |
| 5,639,641 | A | 6/1997 | Pedersen et al. |
| 5,648,237 | A | 7/1997 | Carter |
| 5,693,761 | A | 12/1997 | Queen et al. |
| 5,693,762 | A | 12/1997 | Queen et al. |
| 5,766,886 | A | 6/1998 | Studnicka et al. |
| 5,770,196 | A | 6/1998 | Studnicka |
| 5,789,199 | A | 8/1998 | Joly et al. |
| 5,821,123 | A | 10/1998 | Studnicka |
| 5,821,337 | A | 10/1998 | Carter et al. |
| 5,840,523 | A | 11/1998 | Simmons et al. |
| 5,859,205 | A | 1/1999 | Adair et al. |
| 5,869,619 | A | 2/1999 | Studnicka |
| 5,877,293 | A | 3/1999 | Adair et al. |

(Continued)

FOREIGN PATENT DOCUMENTS

| | | | |
|---|---|---|---|
| EP | 3344286 | A1 | 7/2018 |
| JP | WO2002031140 | A1 | 2/2004 |

(Continued)

OTHER PUBLICATIONS

Abhinandan., et al., "Analysis and Improvements to Kabat and Structurally Correct Numbering of Antibody Variable Domains", Molecular Immunology, Aug. 2008. vol. 45, No. 14, pp. 3832-3839.

(Continued)

*Primary Examiner* — Nelson B Moseley, II
*Assistant Examiner* — Josephine K Darpolor
(74) *Attorney, Agent, or Firm* — Jason R. Bond; Casimir Jones, S.C.

(57) ABSTRACT

Provided herein are anti-Anti-Müllerian Hormone Receptor 2 (AMHR2) antibodies and methods of using such antibodies, for example, in the treatment of cancer.

16 Claims, 6 Drawing Sheets

Specification includes a Sequence Listing.

(56) References Cited

U.S. PATENT DOCUMENTS

| | | | |
|---|---|---|---|
| 5,886,152 | A | 3/1999 | Nakatani et al. |
| 5,959,177 | A | 9/1999 | Hein et al. |
| 6,040,498 | A | 3/2000 | Stomp et al. |
| 6,054,297 | A | 4/2000 | Carter et al. |
| 6,072,035 | A | 6/2000 | Hardman et al. |
| 6,180,370 | B1 | 1/2001 | Queen et al. |
| 6,194,551 | B1 | 2/2001 | Idusogie et al. |
| 6,417,429 | B1 | 7/2002 | Hein et al. |
| 6,420,548 | B1 | 7/2002 | Vezina et al. |
| 6,602,684 | B1 | 8/2003 | Umana et al. |
| 6,706,477 | B2 | 3/2004 | Zauderer |
| 6,800,442 | B2 | 10/2004 | Zauderer |
| 6,872,518 | B2 | 3/2005 | Zauderer |
| 6,881,557 | B2 | 4/2005 | Foote |
| 6,893,625 | B1 | 5/2005 | Robinson et al. |
| 6,949,245 | B1 | 9/2005 | Sliwkowski |
| 6,982,321 | B2 | 1/2006 | Winter |
| 7,022,500 | B1 | 4/2006 | Queen et al. |
| 7,125,978 | B1 | 10/2006 | Vezina et al. |
| 8,409,572 | B2 | 4/2013 | Beliard et al. |
| 2002/0164328 | A1 | 11/2002 | Shinkawa et al. |
| 2003/0115614 | A1 | 6/2003 | Kanda et al. |
| 2003/0157108 | A1 | 8/2003 | Presta |
| 2004/0093621 | A1 | 5/2004 | Shitara et al. |
| 2004/0109865 | A1 | 6/2004 | Niwa et al. |
| 2004/0110282 | A1 | 6/2004 | Kanda et al. |
| 2004/0110704 | A1 | 6/2004 | Yamane et al. |
| 2004/0132140 | A1 | 7/2004 | Satoh et al. |
| 2005/0123546 | A1 | 6/2005 | Umana et al. |
| 2014/0234213 | A1 | 8/2014 | Adams et al. |
| 2017/0035903 | A1 | 2/2017 | Dubreuil et al. |

FOREIGN PATENT DOCUMENTS

| | | | | |
|---|---|---|---|---|
| JP | WO2003084570 | A1 | 8/2005 | |
| JP | WO2003085119 | A1 | 8/2005 | |
| JP | WO2005035778 | A1 | 12/2006 | |
| JP | WO2005053742 | A1 | 6/2007 | |
| JP | WO2005035586 | A1 | 11/2007 | |
| JP | 2010508810 | A | 3/2010 | |
| JP | 2018526390 | A | 9/2018 | |
| WO | WO-1993011794 | A1 | 6/1993 | |
| WO | WO-9316185 | A2 | 8/1993 | |
| WO | WO-1997030087 | A1 | 8/1997 | |
| WO | WO-1998058964 | A1 | 12/1998 | |
| WO | WO-1999022764 | A1 | 5/1999 | |
| WO | WO-1999051642 | A1 | 10/1999 | |
| WO | WO-2000061739 | A1 | 10/2000 | |
| WO | WO-2001029246 | A1 | 4/2001 | |
| WO | WO-2003011878 | A2 | 2/2003 | |
| WO | WO-2003085107 | A1 | 10/2003 | |
| WO | WO-2004056312 | A2 | 7/2004 | |
| WO | WO-2008077546 | A1 | 7/2008 | |
| WO | WO-2011120134 | A1 | 10/2011 | |
| WO | WO-2011120135 | A1 | 10/2011 | |
| WO | WO-2012166712 | A1 | 12/2012 | |
| WO | WO-2017040969 | A1 * | 3/2017 | ........... A61K 31/337 |
| WO | WO-2018189379 | A1 | 10/2018 | |
| WO | WO-2018189381 | A1 | 10/2018 | |

OTHER PUBLICATIONS

Al-Lazikani B., et al., "Standard Conformations for the Canonical Structures of Immunoglobulins," Journal of Molecular Biology, 1997, vol. 273, pp. 927-948 (17 Pages).

Altschul S.F., et al., "Basic Local Alignment Search Tool", Journal of Molecular Biology, vol. 215, No. 3, 1990, pp. 403-410.

Altschul S.F., et al., "Gapped BLAST and PSI-BLAST: A New Generation of Protein Database Search Programs", Nucleic Acids Research, Sep. 1, 1997, vol. 25, No. 17, pp. 3389-3402.

Batzer et al., Enhanced evolutionary PCR using oligonucleotides with inosine at the 3'-terminus. Nucleic Acids Res. Sep. 25, 1991;19(18):5081.

Capel P.J.A., et al., "Heterogeneity of Human IgG Fc Receptors", ImmunoMethods, Feb. 1994, vol. 4, No. 1, pp. 25-34.

Charlton K.A., et al., "Expression and Isolation of Recombinant Antibody Fragments in E. coli", Methods in molecular biology, vol. 248. B.K.C. Lo, ed, Humana Press, Totowa, N.J., 2003, pp. 245-254.

Chothia C., et al., "Canonical Structures for the Hypervariable Regions of Immunoglobulins," Journal of Molecular Biology, Aug. 20, 1987, vol. 196, No. 4, pp. 901-917.

Chu S.Y., et al., "Inhibition of B cell Receptor-mediated Activation of Primary Human B Cells by Coengagement of CD19 and FcgammaRIIb with Fc-Engineered Antibodies", Molecular Immunology, Sep. 2008, vol. 45, No. 15, pp. 3926-3933.

Clynes R., et al., "Fc Receptors are Required in Passive and Active Immunity to Melanoma", Proceedings of the National Academy of Sciences of the USA, vol. 95, No. 2, pp. 652-656, Jan. 1998.

Cox., et al., "Immunoassay Methods," in Assay Guidance Manual, Mar. 15, 2023, www.ncbi.nlm.nih.gov/books/NBK92434/, 10 Pages.

Creighton T.E, "Proteins: Structures and Molecular Properties", W H Freeman & Co, 2nd edition, Dec. 1993, 6 Pages.

Daeron M., et al., "FC Receptor Biology", Annual Review of Immunology, vol. 15, 1997, pp. 203-234.

De Gregorio E., et al., "Vaccine Adjuvants: Mode of Action," Frontiers in Immunology, Jul. 31, 2013, vol. 4, No. 214, pp. 1-6.

Estupina P., et al., "The Anti-Tumor Efficacy of 3C23K, a Glyco-Engineered Humanized Anti-MISRII Antibody, in an Ovarian Cancer Model Is Mainly Mediated by Engagement of Immune Effector Cells", Oncotarget, 2017, vol. 8, No. 23, pp. 37061-37079, DOI: 10.18632/oncotarget.15715, XP055403879.

Fendly B.M., et al., "Characterization of Murine Monoclonal Antibodies Reactive to Either the Human Epidermal Growth Factor Receptor or HER2/neu gene product", Cancer Research, vol. 50, Mar. 1, 1990, pp. 1550-1558.

Finco D., et al., "Comparison of Competitive Ligand-binding Assay and Bioassay Formats for the Measurement of Neutralizing Antibodies to Protein Therapeutics", Journal of Pharmaceutical and Biomedical Analysis, vol. 54, 2011, pp. 351-358.

Fishwild et al., High-avidity human IgG kappa monoclonal antibodies from a novel strain of minilocus transgenic mice. Nat BiotechnoL Jul. 1996;14(7):845-51.

Galluzzil L., et al., "Molecular Mechanisms of Cell Death: Recommendations of the Nomenclature Committee on Cell Death 2018", Cell Death & Differentiation, vol. 25, Jan. 23, 2018, pp. 486-541.

Gazzano-Santoro H., et al., "A Non-radioactive Complement-dependent Cytotoxicity Assay for Anti-CD20 Monoclonal Antibody", Journal of Immunological Methods, vol. 202, 1997, pp. 163-171.

Gerngross T.U., "Advances in the Production of Human Therapeutic Proteins in Yeasts and Filamentous Fungi", Nature Biotechnology, vol. 22, No. 11, Nov. 2004, pp. 1409-1414.

Ghahroudi M.A., et al., "Selection and Identification of Single Domain Antibody Fragments from Camel Heavy-Chain Antibodies," FEBS Letters, Sep. 15, 1997, vol. 414, No. 3, pp. 521-526.

Graham et al. Characteristics of a human cell line transformed by DNA from human adenovirus type 5. J Gen Virol. Jul. 1977;36(1):59-74.

Guyer R.L., et al., "Immunoglobulin Binding by Mouse Intestinal Epithelial Cell Receptors", Journal of Immunology, vol. 117, No. 2, Aug. 1, 1976, pp. 587-593.

Harmsen M.M., et al., "Properties, Production, and Applications of Camelid Single-Domain Antibody Fragments," Applied Microbiology and Biotechnology, Nov. 2007, vol. 77, No. 1, pp. 13-22.

Honegger A., et al., "Yet Another Numbering Scheme for Immunoglobulin Variable Domains: An Automatic Modeling and Analysis Tool", Journal of Molecular Biology, vol. 309, No. 3, Jun. 8, 2001, pp. 657-670.

Horsten H.H.V., et al., "Production of Non-fucosylated Antibodies by Co-expression of Heterologous GDP-6-Deoxy-D-Lyxo-4-Hexulose Reductase", Glycobiology, 2010, vol. 20 No. 12, pp. 1607-1618.

(56)        References Cited

OTHER PUBLICATIONS

Huang H., et al., "Characterization and Optimization of the Glucan Particle-Based Vaccine Platform," Clinical and Vaccine Immunology, Oct. 2013, vol. 20, No. 10, pp. 1585-1591.

Hunkapiller M., et al., "A Microchemical Facility for the Analysis and Synthesis of Genes and Proteins," Nature, Jul. 12, 1984, vol. 310, No. 5973, pp. 105-111.

Idusogie E. E., et al., "Mapping of the C1q Binding Site on Rituxan, a Chimeric Antibody With a Human IgG1 Fc," Journal of Immunology, Apr. 15, 2000, vol. 164, No. 8, pp. 4178-4184 (8 pages).

International Search Report and Written Opinion for International Application No. PCT/US2021/015910, mailed May 14, 2021, 21 Pages.

Janeway C. A., et al., "Immuno Biology: The Immune System in Health and Disease", Elsevier Science Ltd., NY, 2001, 5th ed., pp. 1-41 (TOC only).

Jones P.T., et al., "Replacing the Complementarity-determining Regions in a Human Antibody with Those from a Mouse", Nature, May 29, 1986, vol. 321, No. 6069, pp. 522-525.

Junghans R. P., et al., "Anti-Tac-H, A Humanized Antibody to the Interleukin 2 Receptor With New Features for Immunotherapy in Malignant and Immune Disorders," Cancer Research, May 1, 1990, vol. 50, pp. 1495-1502.

Kabat E.A., "Sequences of Proteins of Immunological Interest," U.S. Department of Health and Human Services, 1991, vol. 1, Fifth Edition, TOC Only, 13 Pages.

Kanda Y., et al., "Comparison of Cell Lines for Stable Production of Fucose-Negative Antibodies With Enhanced ADCC", Biotechnology and Bioengineering, Jul. 5, 2006, vol. 94, No. 4, pp. 680-688.

Karlin S., et al., "Applications and Statistics for Multiple High-Scoring Segments in Molecular Sequences," Proceedings of the National Academy of Sciences of the United States of America, Jun. 15, 1993, vol. 90, No. 12, pp. 5873-5877.

Karlin S., et al., "Methods for Assessing the Statistical Significance of Molecular Sequence Features by Using General Scoring Schemes," Proceedings of the National Academy of Sciences of the United States of America, Mar. 1990, vol. 87, No. 6, pp. 2264-2268, DOI:10.1073/pnas.87.6.2264.

Kersual N., et al., "The Human Mullerian Inhibiting Substance Type II Receptor as Immunotherapy Target for Ovarian Cancer: Validation Using mAb12G4," MAbs, 2014, vol. 6, No. 5, pp. 1314-1326.

Kim J-K., et al., "Identifying Amino Acid Residues That Influence Plasma Clearance of Murine IgG1 Fragments by Site-directed Mutagenesis", European Journal of Immunology, 1994, vol. 24, No. 3, pp. 542-548.

Knappik A., et al., "Fully Synthetic Human Combinatorial Antibody Libraries (HuCAL) Based on Modular Consensus Frameworks and CDRS Randomized With Trinucleotides," Journal of Molecular Biology, Feb. 11, 2000, vol. 296, No. 1, pp. 57-86.

Krebs B., et al., "High-throughput Generation and Engineering of Recombinant Human Antibodies", Ournal of Immunological Methods, Aug. 1, 2001, vol. 254, pp. 6784.

Lazar et al., "Engineered Antibody FC Variants with Enhanced Effector Function", Proceedings of the National Academy of Sciences, USA, 2006, vol. 103, No. 11, pp. 4005-4010.

Leenaars M., et al., "Immune Responses and Side Effects of Five Different Oil-based Adjuvants in Mice," Veterinary Immunology and Immunopathology, Feb. 27, 1998, vol. 61, No. 2-4, pp. 291-304.

Lefranc M-P., et al., "IMGT Unique Numbering for Immunoglobulin and T Cell Receptor Variable Domains and Ig Superfamily V-like Domains", Developmental and Comparative Immunology, vol. 27, No. 1, Jan. 2003, pp. 55-77.

Li., et al., "Optimization of Humanized IgGs in Glycoengineered Pichia Pastoris", Nature Biotechnology, vol. 24, No. 2, Feb. 2006, pp. 210-215.

Lonberg N., et al., "Antigen-specific Human Antibodies from Mice Comprising Four Distinct Genetic Modifications", Nature, Apr. 28, 1994, vol. 368, No. 6474, pp. 856-859.

Lu Y., et al., "Identification of IgG1 Variants with Increased Affinity to FcγRIIIa and UNaltered Affinity to FcγRI and FcRn: Comparison of Soluble Receptor-based and Cell-based Binding Assays", Journal of Immunological Methods vol. 365 , Feb. 28, 2011, vol. 365, No. 1, pp. 132-141.

Luger D., et al., "Either a Th17 or a Th1 Effector Response Can Drive Autoimmunity: Conditions of Disease Induction Affect Dominant Effector Category," Journal of Experimental Medicine Apr. 14, 2008, vol. 205, No. 4, pp. 799-810.

MacCallum R.M. et al., "Antibody-antigen Interactions: Contact Analysis and Binding Site Topography", Journal of Molecular Biology, Oct. 11, 1996, vol. 262, No. 5, pp. 732-745.

Mather J.P., "Establishment and Characterization of Two Distinct Mouse Testicular Epithelial Cell Lines," Biology of Reproduction, Aug. 1980, vol. 23, No. 1, pp. 243-252.

Mather J.P., et al., "Culture of Testicular Cells in Hormone-Supplemented Serum-Free Medium," Annals of the New York Academy of Sciences, 1982, vol. 383, pp. 44-68.

Mazumder S., et al., "Primary Immunoprevention of Epithelial Ovarian Carcinoma by Vaccination against the Extracellular Domain of Anti-Mullerian Hormone Receptor II," Cancer Prevention Research, Philadelphia, Nov. 2017, vol. 10, No. 11, pp. 612-624.

Mendez M.J., et al., "Functional Transplant of Megabase Human Immunoglobulin Loci Recapitulates Human Antibody Response in Mice", Nature Genetics, Feb. 1997, vol. 15, No. 2, pp. 146-156.

Morrison S.L., et al., "Chimeric Human Antibody Molecules: Mouse Antigen-Binding Domains with Human Constant Region Domains", Proceedings of the National Academy of Sciences of the United States of America, Nov. 1984, vol. 81, No. 21, pp. 6851-6855.

Muyldermans S., et al., "Recognition of Antigens by Single-Domain Antibody Fragments: The Superfluous Luxury of Paired Domains," Trends in Biochemical Sciences, Apr. 2001, vol. 26, No. 4, pp. 230-235.

Neuberger M.S., et al., "Recombinant Antibodies Possessing Novel Effector Functions," Nature, Dec. 13-19, 1984, vol. 312. No. 5995. pp. 604-608.

Nordstrom J.L., et al., "Anti-Tumor Activity and Toxicokinetics Analysis of MGAH22, an Anti-HER2 Monoclonal Antibody with Enhanced Fc(Gamma) Receptor Binding Properties," Breast Cancer Research, 2011, vol. 13, No. 6 (R123), 14 Pages.

Ohtsuka E., et al., "An Alternative Approach to Deoxyoligonucleotides as Hybridization Probes by Insertion of Deoxyinosine at Ambiguous Codon Positions," The Journal of Biological Chemistry, Mar. 10, 1985, vol. 260, No. 5, pp. 2605-2608.

Okazaki A., et al., "Fucose Depletion From Human LgG1 Oligosaccharide Enhances Binding Enthalpy and Association Rate Between LgG1 and Fc(Gamma)RIIIa," Journal of Molecular Biology, Mar. 5, 2004, vol. 336, No. 5, pp. 1239-1249.

Pluckthun A., "Antibodies from *Escherichia coli*," The Phamacology of Monoclonal Antibodies, Springer-Verlag, Edited by Rosenburg M., Moore G.P., New York, 1994, vol. 113, pp. 269-315, 48 Pages.

Presta L.G., "Antibody Engineering," Current Opinion in Structural Biology, 1992, vol. 2, pp. 593-596.

Rak A.Y., et al., "Anti-mullerian Hormone Receptor Type II as a Potential Target for Antineoplastic Therapy," Biochemistry, Moscow, Supplement Series B: Biomedical Chemistry, Maik Nauka—Interperiodica, RU, vol. 13, No. 3, Aug. 14, 2019, pp. 202-213, DOI: 10.1134/S1990750819030053, ISSN: 1990-7508, XP036862693, [retrieved on Aug. 14, 2019].

Ravetch J.V., et al., "Fc Receptors", Annual Review of Immunology, 1991, vol. 9, pp. 457-492.

Remington., "Pharmaceutical Sciences", Mack Publishing, 1985, TOC only, 4 pages.

Riechmann L., et al., "Reshaping Human Antibodies for Therapy," Nature, Mar. 24, 1988, vol. 332 (6162), pp. 323-327.

Ripka J., et al., "Two Chinese Hamster Ovary Glycosylation Mutants Affected in the Conversion of GDP-Mannose to GDP-Fucose", Archives of Biochemistry and Biophysics, Sep. 1986, vol. 249, No. 2, pp. 533-545.

(56) References Cited

OTHER PUBLICATIONS

Roguska M.A., et al., "A Comparison of Two Murine Monoclonal Antibodies Humanized by CDR-Grafting and Variable Domain Resurfacing," Protein Engineering, 1996, vol. 9, No. 10, pp. 895-904.

Rossolini G M., et al., "Use of Deoxyinosine-containing Primers vs Degenerate Primers for Polymerase Chain Reaction Based on Ambiguous Sequence Information", Molecular and Cellular Probes, Apr. 1994, vol. 8, No. 2, pp. 91-98.

Sakalar C., et al., "A Novel Peptide-specific Monoclonal Antibody with a Potential Use for Immunotherapy Recognizes AMHR2 Expressed by Ovarian Cancer Cells", European Journal of Cancer, vol. 61, Suppl. 1, 2016, S9-S218, p. S212, XP029634586.

Sakalar C., et al., "Regulation of Murine Ovarian Epithelial Carcinoma by Vaccination against the Cytoplasmic Domain of Anti-Mullerian Hormone Receptor II," Journal of Immunology Research, 2015, vol. 2015, Article ID. 630287, 14 Pages.

Scopes R.K., "Protein Purification: Principles and Practice", 3rd Edition, Springer-Verlag, NY, 1993, TOC only, 15 pages.

Shields R.L., et al., "High Resolution Mapping of the Binding Site on Human IgG1 for Fc (Gamma) RI, Fc (Gamma) RII, Fc (Gamma) RIII, and FcRn and Design of LgG1 Variants With Improved Binding to the Fc (Gamma) R," Journal of Biological Chemistry, Mar. 2, 2001, vol. 276, No. 9, pp. 6591-6604 (15 Pages).

Shields R.L., et al., "Lack of Fucose on Human IgG1 N-linked Oligosaccharide Improves Binding to Human Fcgamma RIII and Antibody-dependent Cellular Toxicity," Journal of Biological Chemistry, Jul. 26, 2002, vol. 277, No. 30, pp. 26733-26740.

Siiman O., et al., "Competitive Antibody Binding to Soluble CD16B Antigen and CD16B Antigen on Neutrophils in Whole Blood by Flow Cytometry", Cytometry, May 1, 2001, vol. 44, No. 1, pp. 30-37.

Stavenhagen J.B., et al., "Fc Optimization of Therapeutic Antibodies Enhances Their Ability to Kill Tumor Cells in Vitro and Controls Tumor Expansion in Vivo via Low-affinity Activating Fc(Gamma) Receptors," Cancer Research, Sep. 15, 2007, vol. 67, No. 18, pp. 8882-8890.

Steinman L., "A Brief History of T(H)17, The First Major Revision in the T(H) 1/T(H)2 Hypothesis of T Cell-Mediated Tissue Damage," Nature Medicine, Feb. 2007, vol. 13, No. 2, pp. 139-145 (8 Pages).

Stewart R., et al., "A Variant Human IgG1-Fc Mediates Improved ADCC", Protein Engineering Design & Selection, Sep. 2011, vol. 24, No. 9, pp. 671-678.

Strohl., et al., "Antibody Fragments as Therapeutics, In Woodhead Publishing Series in Biomedicine," Therapeutic Antibody Engineering, Woodhead Publishing, 2012, pp. 265-595.

Tan P., et al., ""Superhumanized" Antibodies: Reduction of Immunogenic Potential by Complementarity-determining Region Grafting With Human Germline Sequences: Application to an Anti-CD28," The Journal of Immunology, Jul. 15, 2002, vol. 169, No. 2, pp. 1119-1125 (8 Pages).

Urlaub G., et al., "Isolation of Chinese Hamster Cell Mutants Deficient in Dihydrofolate Reductase Activity", The Proceedings of the National Academy of Sciences, USA, vol. 77, No. 7, Jul. 1980, pp. 4216-4220.

Vaswani S.K., et al., "Humanized Antibodies As Potential Therapeutic Drugs", Annals of Allergy, Asthma & Immunology, 1998, vol. 81, pp. 105-119.

Verhoeyen M., et al., "Reshaping Human Antibodies: Grafting an Antilysozyme Activity," Science, Mar. 25, 1988, vol. 239, No. 4847, pp. 1534-1536.

Winter G., "Synthetic Human Antibodies and a Strategy for Protein Engineering", FEBS Letters, Jun. 1998, vol. 23, No. 430, pp. 92-94.

Yamane-Ohnuki N., et al., "Establishment of FUT8 Knockout Chinese Hamster Ovary Cells: An Ideal Host Cell Line for Producing Completely Defucosylated Antibodies With Enhanced Antibody-Dependent Cellular Cytotoxicity", Biotechnology and Bioengineering, Sep. 5, 2004, vol. 87, No. 5, pp. 614-622.

Yazaki P.J., et al., "Expression of Recombinant Antibodies in Mammalian Cell Lines", Methods in molecular biology, 2004, vol. 248, pp. 255-268.

* cited by examiner

ANTI-MÜLLERIAN HORMONE RECEPTOR 2 ANTIBODIES AND METHODS OF USE

CROSS-REFERENCE TO RELATED APPLICATIONS

This application claims the benefit under 35 U.S.C. § 119 of U.S. provisional application No. 62/968,840, filed Jan. 31, 2020, wherein the contents are incorporated herein by reference in their entirety.

BACKGROUND

Epithelial ovarian carcinoma (EOC) is the most prevalent and lethal form of ovarian cancer representing ~85% of all ovarian cancers. An array of non-definitive symptoms associated with EOC onset and the lack of effective biomarkers for early detection often results in late diagnoses at advanced diseased stages resulting in high rates of disease recurrence and poor prognoses following current standard of care.

AMHR2 is a serine/threonine kinase receptor homologous to type II receptors of the transforming growth factor-beta (TGFβ) superfamily. Anti-Müllerian hormone (AMH) is the cognate ligand of AMHR2, and binding of AMH to the extracellular domain of AMHR2 (AMHR2-ED) signals cell cycle arrest and programmed cell death resulting in regression of the Müllerian ducts during male development and regulation of oocyte development, and control of ovarian reserve and fertility in adult females. AMHR2 is overexpressed in the majority of human EOCs.

Accordingly, there is an urgent need for need for new and effective therapies for treating and managing cancer, especially EOC, including therapies targeting AMHR2.

SUMMARY

The invention is based, in part, on the discovery of anti-AMHR2 antibodies and AMHR2 vaccine formulations that are useful in the treatment of cancers, for example, ovarian cancer.

In one aspect, provided is an isolated antibody that binds to human Anti-Müllerian Hormone Receptor II (AMHR2), wherein the antibody binds within residues 11-32 (SEQ ID NO: 12) of the AMHR2 extracellular domain (SEQ ID NO: 11). In some embodiments, the antibody binds within residues 20-26 (SEQ ID NO: 13) of the AMHR2 extracellular domain (SEQ ID NO: 11). In some embodiments, the antibody binds within residues 22-26 (SEQ ID NO: 14) of the AMHR2 extracellular domain (SEQ ID NO: 11).

In one aspect, provided is an isolated antibody that binds to human AMHR2 (SEQ ID NO: 9), wherein the antibody competes for binding to human AMHR2 with Anti-Müllerian Hormone (AMH). In one aspect, provided is an isolated antibody that binds to human AMHR2 (SEQ ID NO: 9), wherein the antibody competes for binding to human AMHR2 with an antibody disclosed herein.

In one aspect, provided is an isolated antibody comprising a heavy chain comprising a variable heavy (VH) chain sequence comprising three heavy chain CDR sequences, CDR-H1, CDR-H2, and CDR-H3, and a light chain comprising a variable light (VL) chain sequence comprising three light chain CDR sequences, CDR-L1, CDR-L2, and CDR-L3, wherein CDR-H1 comprises the sequence shown in SEQ ID NO: 1, CDR-H2 comprises the sequence shown in SEQ ID NO: 2, CDR-H3 comprises the sequence shown in SEQ ID NO: 3, CDR-L1 comprises the sequence shown in SEQ ID NO: 4, CDR-L2 comprises the sequence shown in SEQ ID NO: 5, and CDR-L3 comprises the sequence shown in SEQ ID NO: 6.

In some embodiments of any of the foregoing antibodies, the VH chain sequence comprises the sequence shown in SEQ ID NO: 7, and/or the VL chain sequence comprises the sequence show in SEQ ID NO: 8. In some embodiments, the VH chain sequence consists essentially of the sequence shown in SEQ ID NO: 7, and/or the VL chain sequence consists essentially of the sequence show in SEQ ID NO: 8. In some embodiments, the VH chain sequence consists of the sequence shown in SEQ ID NO: 7, and/or the VL chain sequence consists of the sequence show in SEQ ID NO: 8.

In some embodiments of any of the foregoing antibodies, the antibody binds to human AMHR2 with a $K_D$ of less than or equal to about 0.1, 0.2, 0.5, 1, 2, 3, 4, or 5×10–9 M, as measured by surface plasmon resonance (SPR).

In some embodiments of any of the foregoing antibodies, the antibody is a humanized, human, or chimeric antibody. For example, in some embodiments, the heavy chain and light chain CDRs are interposed between human or humanized immunoglobulin framework regions. In some embodiments, the antibody is a monoclonal antibody.

In some embodiments of any of the foregoing antibodies, the antibody comprises a heavy chain human constant region or a human Fc region of a class selected from IgG, IgA, IgD, IgE, and IgM. In some embodiments, the heavy chain human constant region or the human Fc region is of the class IgG and a subclass selected from IgG1, IgG2, IgG3, and IgG4, e.g., the antibody comprises a wild-type human IgG1 Fc region. In some embodiments, the heavy chain human constant region or the human Fc region comprise one or more amino acid substitutions, wherein the one or more substitutions result in increased antibody half-life, increased ADCC activity, increased ADCP activity, or increased CDC activity compared with the constant region or Fc without the one or more substitutions. In some embodiments, the heavy chain human constant region or the human Fc region binds an Fcγ Receptor selected from the group consisting of: FcγRI, FcγRIIa, FcγRIIb, FcγRIIc, FcγRIIIa, and FcγRIIIb.

In some embodiments of any of the foregoing antibodies, the antibody induces apoptosis of a cell (e.g., an AMHR2+ cell). In some embodiments, the antibody has antibody-dependent cell-mediated cytotoxicity (ADCC) activity. In some embodiments, the antibody has antibody-mediated cellular phagocytosis (ADCP) activity. In some embodiments, the antibody has complement-dependent cytotoxicity (CDC) activity.

In one aspect, provided is an isolated polynucleotide or set of polynucleotides encoding any of the foregoing antibodies, a VH thereof, a VL thereof, a light chain thereof, a heavy chain thereof, or an antigen-binding portion thereof. In some embodiments, the isolated polynucleotide or set of polynucleotides comprises cDNA. In one aspect, provided is a vector or set of vectors comprising any of the foregoing polynucleotides or sets of polynucleotides. In one aspect, provided is a host cell comprising any of the foregoing polynucleotides or sets of polynucleotides or any of the foregoing vectors or sets of vectors. In one aspect, provided is method of producing an antibody comprising (i) incubating any of the foregoing host cells under conditions so that the host cell expresses the antibody and (ii) purifying the antibody.

In one aspect, provided is a pharmaceutical composition comprising any of the foregoing antibodies and a pharmaceutically acceptable carrier or excipient. In one aspect, provided herein a kit comprising any of the foregoing antibodies or compositions and instructions for use.

In one aspect, provided herein is a method of killing, disabling, or depleting cells that express AMHR2 on the cell surface (AMHR2+ cells), comprising contacting the AMHR2+ cells with any of the foregoing antibodies or compositions. In some embodiments, the antibody kills, disables, or depletes the AMHR2+ cells by at least one of programmed cell death, antibody-dependent cell-mediated cytotoxicity (ADCC), complement-dependent cytotoxicity (CDC), and antibody-mediated phagocytosis (ADCP). In some embodiments, contacting the AMHR2+ cells with the antibody or composition induces apoptosis (e.g., mediated by caspase-3), lysis, death, phagocytosis, or growth arrest of the AMHR2+ cells. In some embodiments, the antibody induces cleavage of PARP-1 in the cell. In some embodiments, the antibody is internalized by the cell. In some embodiments, the antibody has receptor-ligand blocking, agonist, or antagonist activity.

In some embodiments, the AMHR2+ cell is a cancer cell. In some embodiments, contacting the AMHR2+ cells with the antibody or composition occurs in vitro. In some embodiments, contacting the AMHR2+ cells with the antibody or composition occurs in vivo, e.g., in a subject, e.g., a subject with cancer. In some embodiments, the cancer is a solid cancer, e.g., ovarian cancer, e.g., stage I, stage IA, stage IB, stage IC, stage II, stage IIA, stage IIB, stage III, stage IIIA1, stage IIIA2, stage IIIB, stage IIIC, stage IV, stage IVA, or stage IVB ovarian cancer. In some embodiments, the cancer is a metastatic and/or refractory cancer.

In one aspect, provided herein is a method of treating cancer (e.g., an AMHR2+ cancer) in a subject in need thereof, comprising administering to the subject any of the foregoing antibodies or compositions. In some embodiments, the cancer is a solid cancer, e.g., ovarian cancer, e.g., stage I, stage IA, stage IB, stage IC, stage II, stage IIA, stage IIB, stage III, stage IIIA1, stage IIIA2, stage IIIB, stage IIIC, stage IV, stage IVA, or stage IVB ovarian cancer. In some embodiments, the cancer is a metastatic and/or refractory cancer. In some embodiments, the antibody is effective at reducing a cancer volume as compared to the cancer volume prior to administration of the antibody. In some embodiments, the antibody is effective at reducing a cancer growth rate as compared to the cancer growth rate prior to administration of the antibody. In some embodiments, the antibody is effective at eliminating the cancer.

In one aspect, provided is a method of inducing an immune response in a subject in need thereof, comprising administering to the subject a composition comprising an AMHR2 extracellular domain polypeptide. In one aspect, provided is a method of treating a cancer (e.g., an AMHR2+ cancer) in a subject in need thereof, comprising administering to the subject a composition comprising an AMHR2 extracellular domain polypeptide. In some embodiments, the administration induces an immune response in the subject. In some embodiments, the immune response is an adaptive immune response. In some embodiments, the AMHR2 extracellular domain polypeptide comprises the amino acid sequence of SEQ ID NO: 11 or an amino acid sequence that comprises at least 8 consecutive amino acids of SEQ ID NO: 11. In some embodiments, the composition further comprises an adjuvant, wherein the adjuvant comprises (a) a carbohydrate, and (b) a metabolizable oil.

In one aspect, provided is a method of treating a cancer (e.g., an AMHR2+ cancer) in a subject in need thereof, comprising administering to the subject a therapeutically effective amount of (i) an anti-AMHR2 antibody (for example, an antibody disclosed herein) and (ii) a composition comprising an AMHR2 extracellular domain polypeptide. In some embodiments, the AMHR2 extracellular domain polypeptide comprises the amino acid sequence of SEQ ID NO: 11 or an amino acid sequence that comprises at least 8 consecutive amino acids of SEQ ID NO: 11.

In some embodiments, the anti-AMHR2 antibody and the composition comprising the AMHR2 extracellular domain polypeptide are administered simultaneously (for example, the composition comprising the AMHR2 extracellular domain polypeptide further comprises the anti-AMHR2 antibody). In some embodiments, the anti-AMHR2 antibody and the composition comprising the AMHR2 extracellular domain polypeptide are administered separately, for example, the anti-AMHR2 antibody is administered first and the composition comprising the AMHR2 extracellular domain polypeptide is administered second. In some embodiments, the composition comprising the AMHR2 extracellular domain further comprises an adjuvant, wherein the adjuvant comprises (a) a carbohydrate, and (b) a metabolizable oil.

In one aspect, provided is a method of treating a cancer (e,g, an AMHR2+ cancer) in a subject in need thereof, comprising administering to the subject a therapeutically effective amount of a composition comprising an AMHR2 extracellular domain polypeptide and an adjuvant, wherein the adjuvant comprises (a) a carbohydrate, and (b) a metabolizable oil. In some embodiments, the AMHR2 extracellular domain polypeptide comprises the amino acid sequence of SEQ ID NO: 11 or an amino acid sequence that comprises at least 8 consecutive amino acids of SEQ ID NO: 11.

In some embodiments of the foregoing methods, where the method comprises administering a composition comprising an adjuvant, the adjuvant comprises a carbohydrate comprising a polysaccharide. In some embodiments, the polysaccharide comprises a mixture of at least two or three polysaccharides. In some embodiments, the adjuvant comprises a carbohydrate having a mixture of at least two or three polysaccharides and the composition is capable of inducing an antigen-specific T cell immune response comprising both a type-1 and a type-17 proinflammatory T cell response when the composition is administered to the subject. In some embodiments, the carbohydrate binds to a pattern recognition receptor, e.g., TLR2 or dectin-1. In some embodiments the polysaccharide, or each polysaccharide in the mixture of polysaccharides, is selected from the group consisting of chitin, dextran, glucan, lentanan, mannan, and combinations thereof. In some embodiments, the polysaccharide or mixture of polysaccharides comprises a glucan, e.g., a β-glucan, e.g., a 1-3 β-glucan. In some embodiments, the mixture of polysaccharides comprises a mixture of chitins, glucans, and mannans. In some embodiments, at least 50% of the carbohydrates in the adjuvant are β-glucans. In some embodiments, the adjuvant comprises zymosan.

In some embodiments of the foregoing methods, where the method comprises administering a composition comprising an adjuvant, the adjuvant comprises a metabolizable oil comprising a purified oil. In some embodiments, the purified oil is mineral oil, e.g., DRAKEOL™ 6 VR. In some embodiments, the metabolizable oil comprises a biodegradable oil, for example, isopropyl myristate, squalene oil, squalane oil, a vegetable oil (e.g., almond oil, castor oil, chaulmoogra oil, coconut oil, corn oil, cottonseed oil, olive oil, peanut oil, persic oil, safflower oil, or soya bean oil), or a combination thereof. In some embodiments, the metabolizable oil comprises a pharmaceutical grade oil.

In some embodiments of the foregoing methods, where the method comprises administering a composition comprising an adjuvant, the adjuvant further comprises a surfactant. In some embodiments, the surfactant comprises mannide monooleate (e.g., MONTANIDE™, e.g., MONTANIDE™ ISA 51 VG), isomannide monooleate, or a combination thereof.

In some embodiments of the foregoing methods, where the method comprises administering a composition comprising an adjuvant, the adjuvant is an emulsion of water and oil, e.g., a water-in-oil emulsion. In some embodiments, the antigen and the carbohydrate are present in a ratio of from about 10:1 to about 1:10 (w/w), for example, the antigen and the carbohydrate are present in a ratio of about 1:1 (w/w).

In some embodiments of the foregoing methods, where the method comprises administering a composition comprising an AMHR2 extracellular domain polypeptide, the method induces an antigen-specific T cell immune response, e.g., a CD4+ T cell and/or a CD8+ T cell response. In some embodiments, the T cell immune response comprises a type-1 and/or a type-17 proinflammatory T cell response. In some embodiments, administering the composition causes reduced granuloma formation relative to a reference level, for example, the level of granuloma formation observed in a subject administered a composition comprising Complete Freund's Adjuvant.

In some embodiments of any of the foregoing methods, the subject has been administered, will be administered, or is simultaneously administered an additional anti-cancer therapy. In some embodiments, the anti-cancer therapy comprises an anti-cancer agent, for example, an anti-cancer agent selected from bevacizumab, bleomycin, carboplatin, cisplatin, cyclophosphamide, docetaxel, doxorubicin, etoposide, gemcitabine, letrozole, olaparib, tamoxifen, topotecan, trabectedin, a CTLA4 antibody, a PD-1 antibody, a PD-L1 antibody, and a TGFβ antibody.

In one aspect, provided is a formulation comprising a water-in-oil emulsion of an AMHR2 extracellular domain polypeptide, zymosan, and MONTANIDE™, wherein the AMHR2 extracellular domain polypeptide and zymosan are present in the formulation at a ratio of between about 1:5 (w/w) and 5:1 (w/w), and wherein the AMHR2 extracellular domain polypeptide comprises an amino acid sequence that is at least 80%, 85%, 90%, 95%, or 100% identical to the amino acid sequence of SEQ ID NO: 11. In some embodiments, the formulation further comprises an anti-AMHR2 antibody (e.g., an anti-AMHR2 antibody disclosed herein).

These and other aspects and features of the invention are described in the following detailed description and claims.

DETAILED DESCRIPTION

I. Definitions

Figure 1:
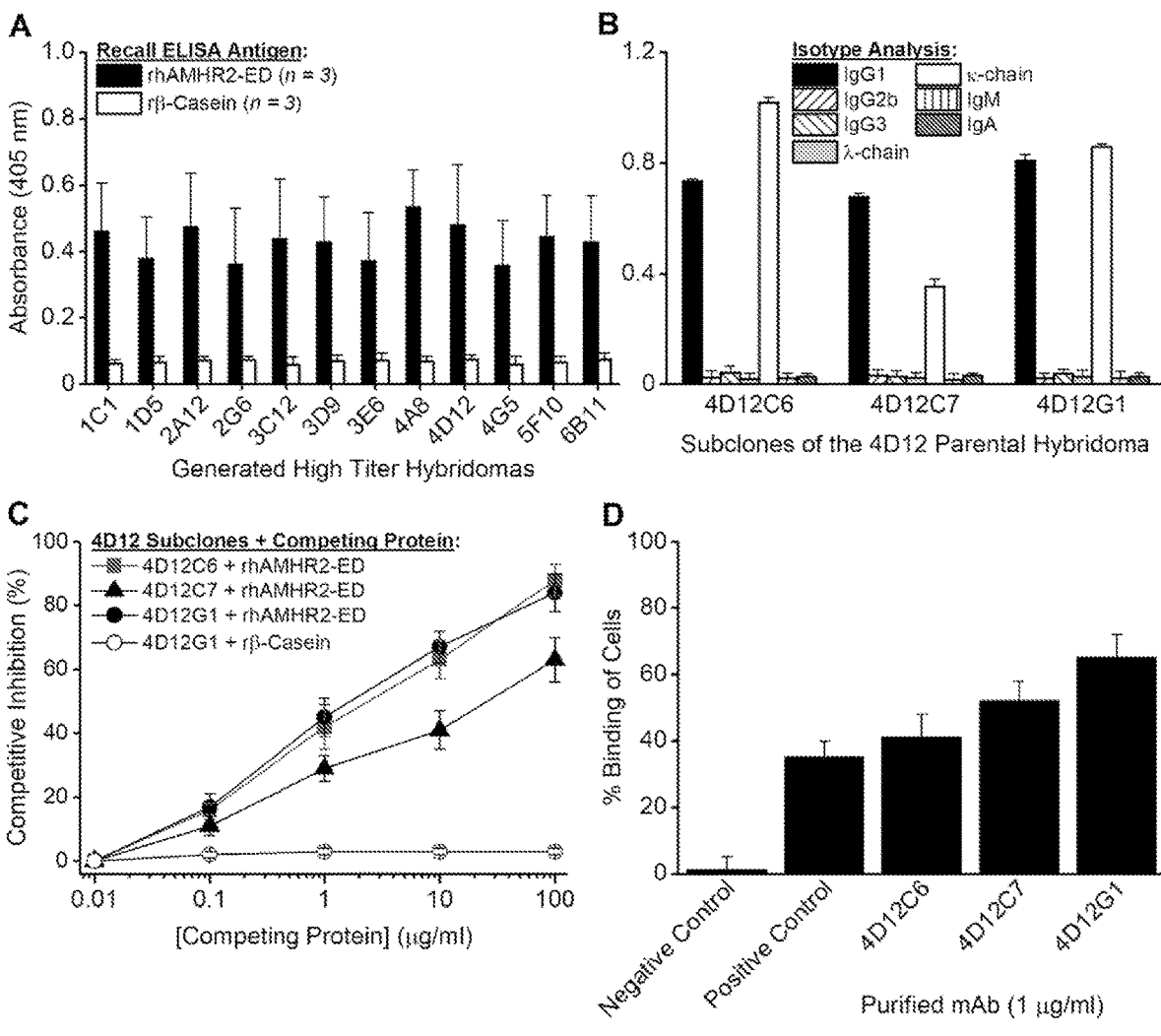
FIG. 1 shows generation of mAbs specific for rhAMHR2-ED. (A) ELISAs show responses of 12 hybridomas to AMHR2-ED and the specificity control antigen, recombinant β-casein at serum dilutions of 1/10,000. (B) Isotype analysis of the 4D12C6, 4D12C7, and 4D12G1 subclones of the 4D12 hybridoma at 1/10,000 dilutions. Determination of antigen-specificity of each subclone (C) by competitive ELISA and (D) by flow cytometry analysis of binding to OVCAR8 cells. Positive control staining of AMHR2-ED-OVCAR8 cells was performed using a commercially available anti-AMHR2-ED mAb (Abcam) whereas IgG1 isotype antibodies with irrelevant specificities were used as negative controls. In all cases, error bars indicate ±SD and the results shown are representative of three experiments yielding similar results.

For convenience, certain terms employed in the specification, examples, and appended claims are collected here.

The articles "a" and "an" are used herein to refer to one or to more than one (i.e., to at least one) of the grammatical object of the article. By way of example, "an element" means one element or more than one element.

As used herein, "adjuvant" means substances, which when administered before, together with, or after administration of an antigen, accelerates, prolong and/or enhances the quality and/or strength of an immune response to the antigen in comparison to the response elicited by administration of the antigen alone.

As used herein, "anti-cancer therapy" means a therapy directed to treating, ameliorating, and/or reducing risk or progression of cancer or a cancerous condition. In some embodiments, an anti-cancer therapy comprises an anti-cancer agent, an agent that is used to treat, ameliorate, and/or reduce risk or progression of cancer or a cancerous condition.

As used herein, the term "antigen" has its ordinary meaning in the art and refers to any molecule or portion of a molecule that can, either by itself or in conjunction with an adjuvant and/or pharmaceutically acceptable carrier, generate an immune response, e.g., an antibody and/or T cell response.

As used herein, the term "administering" means providing a pharmaceutical agent or composition to a subject, and includes, but is not limited to, administering by a medical professional and self-administering.

As used herein, "biodegradable", when used in reference to a material, means those materials that, when introduced into cells, are broken down by cellular machinery (e.g., enzymatic degradation) or by hydrolysis into components that cells can reuse or dispose of without significant toxic effects on the cells. In some embodiments, components generated by breakdown of a biodegradable material do not induce inflammation and/or other adverse effects in vivo. In some embodiments, biodegradable materials are enzymatically broken down. Alternatively or additionally, in some embodiments, biodegradable materials are broken down by hydrolysis.

The term "immune response" refers herein to any response to an antigen or antigenic determinant by the immune system. Exemplary immune responses include humoral immune responses (e.g. production of antigen-specific antibodies (neutralizing or otherwise)) and cell-mediated immune responses (e.g. lymphocyte proliferation). Type-1 proinflammatory immune responses are character-ized by the production of IFNγ. Type-2 regulatory immune responses are characterized by expression of IL-4 or IL-5. Type-17 proinflammatory immune responses are character-ized by expression of IL-17. In some instances, a mixed immune response can be generated. For example, in some instances a mixed Type-1/Type-17 inflammatory immune response is generated that is characterized by the expression of both IFNγ and IL-17.

As used herein, the phrase "metabolizable oil" means an oil that, when introduced into an organism, (1) can be broken down by or eliminated from the organism to a greater extent; (2) can be broken down by or eliminated from the organism more rapidly; and/or (3) results in reduced granuloma for-mation as compared to a reference level, such as the level of granuloma formation in a subject administered Complete Freund's Adjuvant or the level in a subject administered Incomplete Freund's Adjuvant. Thus, a "metabolizable oil," as that phrase is used herein, need not be completely metabolizable. "Reduced granuloma formation" may be characterized, for example, by one or more of: fewer granu-lomas formed, granulomas of reduced severity, granulomas whose severity decreases more rapidly, and granulomas that resolve (partially or completely) more quickly.

As used herein, the terms "polypeptide" and "protein" are used interchangeably and generally have their art-recog-nized meaning of a polymer of at least three amino acids. The term "polypeptide" can refer to polypeptides in their neutral (uncharged) forms or as salts, and either unmodified or modified, e.g., by glycosylation, side chain oxidation, or phosphorylation. The term "polypeptide" can also be used to refer to specific functional classes of polypeptides. When used to refer to a functional class of polypeptides, the term is intended to include functional fragments, variants (e.g., allelic variants), and derivatives of a reference polypeptide, as well as the full length, wild type version of the reference polypeptide. In some embodiments, a polypeptide of a certain functional class shares at least 50%, at least 55%, at least 60%, at least 65%, at least 70%, at least 75%, at least 80%, at least 85%, at least 90%, at least 95%, or at least 97.5% sequence identity at the amino acid level with the full-length version of a reference polypeptide.

As used herein, "percent identity" between amino acid sequences is synonymous with "percent homology," which can be determined using the algorithm of Karlin and Alts-chul (*Proc. Natl. Acad. Sci. USA* 87, 2264-2268, 1990), modified by Karlin and Altschul (*Proc. Natl. Acad. Sci. USA* 90, 5873-5877, 1993). The noted algorithm is incorporated into the NBLAST and XBLAST programs of Altschul et al. (*J. Mol. Biol.* 215, 403-410, 1990). BLAST nucleotide searches are performed with the NBLAST program, score=100, wordlength=12, to obtain nucleotide sequences homologous to a polynucleotide described herein. BLAST protein searches are performed with the XBLAST program, score=50, wordlength=3, to obtain amino acid sequences homologous to a reference polypeptide. To obtain gapped alignments for comparison purposes, Gapped BLAST is utilized as described in Altschul et al. (*Nucleic Acids Res.* 25, 3389-3402, 1997). When utilizing BLAST and Gapped BLAST programs, the default parameters of the respective programs (e.g., XBLAST and NBLAST) are used.

The phrase "pharmaceutically acceptable carrier" as used herein means a pharmaceutically acceptable material, composition, or vehicle, such as a liquid or solid filler, diluent, excipient, thickening agent, solvent, or encapsulating mate-rial, involved in carrying or transporting the subject com-pound from one organ, or portion of the body, to another organ, or portion of the body. The term "carrier" encom-passes both carriers that are not covalently attached and those that are covalently attached to the compounds or compositions they transport.

As used herein, the term "purified" means enrichment of a molecule, compound, or composition relative to other components normally associated with the molecule, com-pound, or composition in a native environment. The term "purified" does not necessarily indicate that complete purity of the molecule, compound, or composition has been achieved. In some embodiments, a "purified" molecule, compound, or composition is at least 90%, at least 95%, or at least 97.5% free of other components.

As used herein, the term "tumor-associated antigen" has its art-recognized meaning and refers to an antigen whose expression is highly correlated with a tumor cell. The tumor-associated antigen may or may not also be expressed in normal cells. In some embodiments, the tumor-associated antigen is over-expressed in tumor cells. In some embodi-ments, expression of the tumor-associated antigen is corre-lated with a particular subtype or particular subtypes of tumor cells.

As used herein, the terms "subject" and "patient" are interchangeable and refer to an organism that receives a treatment (e.g., by being administered an antibody, compo-sition or formulation as disclosed herein). Examples of subjects and patients include mammals, such as humans or non-human animals.

The phrases "therapeutically-effective amount" and "effective amount" as used herein means the amount of an agent that is effective for producing the desired therapeutic effect in at least a sub-population of cells in a subject at a reasonable benefit/risk ratio applicable to any medical treat-ment.

"Treating" a disease in a subject or "treating" a subject having a disease refers to subjecting the subject to a phar-maceutical treatment, e.g., the administration of a drug, such that at least one symptom of the disease is decreased or prevented from worsening.

The term "reference" refers to any sample, standard, or level that is used for comparison purposes. The phrases "reference standard" and "reference level" may be used interchangeably and refer to a value or number derived from a reference sample or subject. In some embodiments, the sample or subject from whom the reference level is derived is matched to a sample of a subject by at least one of the following criteria: age, weight, disease stage, and overall health. For example, in some embodiments, a reference level is a clinical grade or score, or an average clinical grade or score.

The terms "retired self-antigen" and "retired self-pro-teins" are used herein interchangeably and refer to self-proteins that are no longer expressed in normal aged tissues at autoimmunogenic levels.

The term "surfactant" as used herein has its art-recog-nized meaning and refers to a substance that tends to reduce the surface tension between two liquids, between a gas and a liquid, or between a liquid and a solid. In some embodi-ments, the surfactant is an emulsifier, a substance that stabilizes an emulsion.

The term "optionally" is meant, when used sequentially, to include from one to all of the enumerated combinations and contemplates all subcombinations.

The terms "modulate" and "modulation" refer to reducing or inhibiting or, alternatively, activating or increasing, a recited variable.

The terms "increase" and "activate" refer to an increase of 10%, 20%, 30%, 40%, 50%, 60%, 70%, 75%, 80%, 85%, 90%, 95%, 100%, 2-fold, 3-fold, 4-fold, 5-fold, 10-fold, 20-fold, 50-fold, 100-fold, or greater in a recited variable.

The terms "reduce" and "inhibit" refer to a decrease of 10%, 20%, 30%, 40%, 50%, 60%, 70%, 75%, 80%, 85%, 90%, 95%, 2-fold, 3-fold, 4-fold, 5-fold, 10-fold, 20-fold, 50-fold, 100-fold, or greater in a recited variable.

The term "agonize" refers to the activation of receptor signaling to induce a biological response associated with activation of the receptor. An "agonist" is an entity that binds to and agonizes a receptor.

The term "antagonize" refers to the inhibition of receptor signaling to inhibit a biological response associated with activation of the receptor. An "antagonist" is an entity that binds to and antagonizes a receptor.

For any of the structural and functional characteristics described herein, methods of determining these characteristics are known in the art.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present invention, whether explicit or implicit herein. For example, where reference is made to a particular compound, that compound can be used in various embodiments of compositions of the present invention and/or in methods of the present invention, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

It should be understood that the expression "at least one of" includes individually each of the recited objects after the expression and the various combinations of two or more of the recited objects unless otherwise understood from the context and use. The expression "and or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

It should be understood that the order of steps or order for performing certain actions is immaterial so long as the present invention remain operable. Moreover, two or more steps or actions may be conducted simultaneously.

The use of any and all examples, or exemplary language herein, for example, "such as" or "including," is intended merely to illustrate better the present invention and does not pose a limitation on the scope of the invention unless claimed. No language in the specification should be construed as indicating any non-claimed element as essential to the practice of the present invention.

II. Anti-Müllerian Hormone Receptor 2 Antibodies
General

Anti-Müllerian Hormone Receptor 2 (AMHR2) is a serine/threonine kinase receptor homologous to type II receptors of the transforming growth factor-beta (TGFβ) superfamily. Anti-Müllerian hormone (AMH) is the cognate ligand of AMHR2, and binding of AMH to the extracellular domain of AMHR2 (AMHR2-ED) signals cell cycle arrest and programmed cell death resulting in regression of the Müllerian ducts during male development and regulation of oocyte development, and control of ovarian reserve and fertility in adult females. In adult women, the longest AMHR2 transcript codes for a 573 amino acid protein expressed exclusively in the ovary and including the ovarian-specific 127 amino acid AMHR2-ED ligand binding domain, along with a 26 amino acid transmembrane domain, and a 403 amino acid cytoplasmic kinase domain (AMHR2-CD) both of which show extra-ovarian expression.

Provided herein are antibodies against Anti-Müllerian Hormone Receptor 2. In some embodiments, the antibody comprises an isolated antibody that binds to human Anti-Müllerian Hormone Receptor II (AMHR2) (SEQ ID NO: 9) wherein the antibody binds within residues 11-32 (SEQ ID NO: 12) of the AMHR2 extracellular domain (SEQ ID NO: 11). In some embodiments, the antibody binds within residues 20-26 (SEQ ID NO: 13) of the AMHR2 extracellular domain (SEQ ID NO:11). In some embodiments, the antibody binds within residues 22-26 (SEQ ID NO: 14) of the AMHR2 extracellular domain (SEQ ID NO: 11). In some embodiments, the isolated antibody that binds to human AMHR2 (SEQ ID NO: 9) competes for binding to human AMHR2 with Anti-Müllerian Hormone (AMH). In some embodiments, the isolated antibody that binds to human AMHR2 (SEQ ID NO: 9) competes for binding to human AMHR2 with an antibody disclosed herein. In some embodiments, the antibody comprises a human Fc region.

Also provided herein are isolated antibodies comprising a heavy chain comprising a variable heavy (VH) chain sequence comprising three heavy chain CDR sequences, CDR-H1, CDR-H2, and CDR-H3, and a light chain comprising a variable light (VL) chain sequence comprising three light chain CDR sequences, CDR-L1, CDR-L2, and CDR-L3, wherein CDR-H1 comprises the sequence shown in SEQ ID NO: 1, CDR-H2 comprises the sequence shown in SEQ ID NO: 2, CDR-H3 comprises the sequence shown in SEQ ID NO: 3, CDR-L1 comprises the sequence shown in SEQ ID NO: 4, CDR-L2 comprises the sequence shown in SEQ ID NO: 5, and CDR-L3 comprises the sequence shown in SEQ ID NO: 6.

In some embodiments, the VH chain sequence comprises the VH sequence shown in SEQ ID NO: 7. In some embodiments, the VL chain sequence comprises the VL sequence show in SEQ ID NO: 8. In some embodiments, the VH chain sequence comprises the VH sequence shown in SEQ ID NO: 7; and the VL chain sequence comprises the VL sequence show in SEQ ID NO: 8. In some embodiments, the VH chain sequence comprises the VH sequence shown in SEQ ID NO: 7; and the VL chain sequence comprises the VL sequence show in SEQ ID NO: 8 and the human Fc region comprises a wild-type, human IgG1 Fc.

In some embodiments, the VH chain sequence consists of the VH sequence shown in SEQ ID NO: 7. In some embodiments, the VL chain sequence consists of the VL sequence show in SEQ ID NO: 8. In some embodiments, the VH chain sequence consists of the VH sequence shown in SEQ ID NO: 7; and the VL chain sequence consists of the VL sequence show in SEQ ID NO: 8. In some embodiments, the VH chain sequence consists of the VH sequence shown in SEQ ID NO: 7; and the VL chain sequence consists of the VL sequence shown in SEQ ID NO: 8 and the human Fc region comprises a wild-type, human IgG1 Fc.

The term "antibody" is used herein in its broadest sense and includes certain types of immunoglobulin molecules comprising one or more antigen-binding domains that specifically bind to an antigen or epitope. As used herein, unless otherwise indicated, the term "antibody" is understood to mean an intact antibody (e.g., an intact monoclonal antibody), or a fragment thereof, such as a Fc fragment of an antibody (e.g., an Fc fragment of a monoclonal antibody), or an antigen-binding fragment of an antibody (e.g., an antigen-binding fragment of a monoclonal antibody), including an intact antibody, antigen-binding fragment, or Fc fragment that has been modified, engineered, or chemically conjugated. Examples of antigen-binding fragments include Fab, Fab', (Fab')₂, Fv, single chain antibodies (e.g., scFv), minibodies, and diabodies. Examples of antibodies that have been modified or engineered include chimeric antibodies, humanized antibodies, and multispecific antibodies (e.g., bispecific antibodies). An example of a chemically conjugated antibody is an antibody conjugated to a toxin moiety.

The recognized immunoglobulin genes include the kappa, lambda, alpha, gamma, delta, epsilon and mu constant region genes, as well as the myriad immunoglobulin variable region genes. Light chains are classified as either kappa or lambda. The "class" of an antibody or immunoglobulin refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG₂, IgG₃, IgG₄, IgA1, and IgA₂. The heavy chain constant domains that correspond to the different classes of immunoglobulins are called α, δ, ε, γ, and μ, respectively.

An exemplary immunoglobulin (antibody) structural unit is composed of two pairs of polypeptide chains, each pair having one "light" (about 25 kDa) and one "heavy" chain (about 50-70 kDa). The N-terminal domain of each chain defines a variable region of about 100 to 110 or more amino acids primarily responsible for antigen recognition. The terms variable light chain (VL) and variable heavy chain (VH) refer to these light and heavy chain domains respectively. The IgG1 heavy chain comprises of the VH, CH1, CH2 and CH3 domains respectively from the N to C-terminus. The light chain comprises of the VL and CL domains from N to C terminus. The IgG1 heavy chain comprises a hinge between the CH1 and CH2 domains. In certain embodiments, the immunoglobulin constructs comprise at least one immunoglobulin domain from IgG, IgM, IgA, IgD, or IgE connected to a therapeutic polypeptide. In some embodiments, the immunoglobulin domain found in an antibody provided herein, is from or derived from an immunoglobulin based construct such as a diabody, or a nanobody. In certain embodiments, the immunoglobulin constructs described herein comprise at least one immunoglobulin domain from a heavy chain antibody such as a camelid antibody. In certain embodiments, the immunoglobulin constructs provided herein comprise at least one immunoglobulin domain from a mammalian antibody such as a bovine antibody, a human antibody, a camelid antibody, a mouse antibody or any chimeric antibody.

In some embodiments, the antibodies provided herein comprise a heavy chain. In one embodiment, the heavy chain is an IgA. In one embodiment, the heavy chain is an IgD. In one embodiment, the heavy chain is an IgE. In one embodiment, the heavy chain is an IgG. In one embodiment, the heavy chain is an IgM. In one embodiment, the heavy chain is an IgG1. In one embodiment, the heavy chain is an IgG2. In one embodiment, the heavy chain is an IgG3. In one embodiment, the heavy chain is an IgG4. In one embodiment, the heavy chain is an IgA1. In one embodiment, the heavy chain is an IgA2.

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the complementarity determining regions (CDRs), the latter being of highest sequence variability and/or involved in antigen recognition. With the exception of CDR1 in VH, CDRs generally comprise the amino acid residues that form the hypervariable loops. Hypervariable regions (HVRs) are also referred to as "complementarity determining regions" (CDRs), and these terms are used herein interchangeably in reference to portions of the variable region that form the antigen-binding regions. This particular region has been described by Kabat et al., U.S. Dept. of Health and Human Services, Sequences of Proteins of Immunological Interest (1983) and by Chothia et al., J Mol Biol 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The exact residue numbers which encompass a particular CDR will vary depending on the sequence and size of the CDR. Those skilled in the art can routinely determine which residues comprise a particular CDR given the variable region amino acid sequence of the antibody.

The amino acid sequence boundaries of a CDR can be determined by one of skill in the art using any of a number of known numbering schemes, including those described by Kabat et al., supra ("Kabat" numbering scheme); Al-Lazikani et al., 1997, J. Mol. Biol., 273:927-948 ("Chothia" numbering scheme); MacCallum et al., 1996, J. Mol. Biol. 262:732-745 ("Contact" numbering scheme); Lefranc et al., Dev. Comp. Immunol., 2003, 27:55-77 ("IMGT" numbering scheme); and Honegge and Pluckthun, J Mol. Biol., 2001, 309:657-70 ("AHo" numbering scheme); each of which is incorporated by reference in its entirety.

Table A provides the positions of CDR-L1, CDR-L2, CDR-L3, CDR-H1, CDR-H2, and CDR-H3 as identified by the Kabat and Chothia schemes. For CDR-H1, residue numbering is provided using both the Kabat and Chothia numbering schemes.

CDRs may be assigned, for example, using antibody numbering software, such as Abnum, available at www.bio-inf.org.uk/abs/abnum/, and described in Abhinandan and Martin, *Immunology,* 2008, 45:3832-3839, incorporated by reference in its entirety.

TABLE A

| CDR | Kabat | Chothia |
|---|---|---|
| | Residues in CDRs according to Kabat and Chothia numbering schemes. | |
| L1 | L24-L34 | L24-L34 |
| L2 | L50-L56 | L50-L56 |
| L3 | L89-L97 | L89-L97 |
| H1 (Kabat Numbering) | H31-H35B | H26-H32 or H34* |
| H1 (Chothia Numbering) | H31-H35 | H26-H32 |
| H2 | H50-H65 | H52-H56 |
| H3 | H95-H102 | H95-H102 |

*The C-terminus of CDR-H1, when numbered using the Kabat numbering convention, varies between H32 and H34, depending on the length of the CDR.

The "EU numbering scheme" is generally used when referring to a residue in an antibody heavy chain constant region (e.g., as reported in Kabat et al., supra). Unless stated otherwise, the EU numbering scheme is used to refer to residues in antibody heavy chain constant regions described herein.

As used herein, the term "single-chain" refers to a molecule comprising amino acid monomers linearly linked by peptide bonds. In a particular such embodiment, the C-terminus of the Fab light chain is connected to the N-terminus of the Fab heavy chain in the single-chain Fab molecule. As described in more detail herein, an scFv has a variable domain of light chain (VL) connected from its C-terminus to the N-terminal end of a variable domain of heavy chain (VH) by a polypeptide chain. Alternately the scFv comprises of polypeptide chain where in the C-terminal end of the VH is connected to the N-terminal end of VL by a polypeptide chain.

The "Fab fragment" (also referred to as fragment antigen-binding) contains the constant domain (CL) of the light chain and the first constant domain (CHI) of the heavy chain along with the variable domains VL and VH on the light and heavy chains respectively. The variable domains comprise the complementarity determining loops (CDR, also referred to as hypervariable region) that are involved in antigen-binding. Fab' fragments differ from Fab fragments by the addition of a few residues at the carboxy terminus of the heavy chain CHI domain including one or more cysteines from the antibody hinge region.

"F(ab')₂" fragments contain two Fab' fragments joined, near the hinge region, by disulfide bonds. F(ab')₂ fragments may be generated, for example, by recombinant methods or by pepsin digestion of an intact antibody. The F(ab') fragments can be dissociated, for example, by treatment with β-mercaptoethanol.

"Fv" fragments comprise a non-covalently-linked dimer of one heavy chain variable domain and one light chain variable domain.

The "Single-chain Fv" or "scFv" includes the VH and VL domains of an antibody, wherein these domains are present in a single polypeptide chain. In one embodiment, the Fv polypeptide further comprises a polypeptide linker between the VH and VL domains which enables the scFv to form the desired structure for antigen-binding. For a review of scFv see Pluckthun in *The Pharmacology of Monoclonal Antibodies,* vol. 113, Rosenburg and Moore eds., Springer-Verlag, New York, pp. 269-315 (1994). HER2 antibody scFv fragments are described in WO93/16185; U.S. Pat. Nos. 5,571,894; and 5,587,458.

"scFv-Fc" fragments comprise an scFv attached to an Fc domain. For example, an Fc domain may be attached to the C-terminal of the scFv. The Fc domain may follow the VH or $V_L$, depending on the orientation of the variable domains in the scFv (i.e., $V_H$-$V_L$ or $V_L$-$V_H$). Any suitable Fc domain known in the art or described herein may be used. In some cases, the Fc domain comprises an IgG4 Fc domain.

The term "single domain antibody" or "sdAb" refers to a molecule in which one variable domain of an antibody specifically binds to an antigen without the presence of the other variable domain. Single domain antibodies, and fragments thereof, are described in Arabi Ghahroudi et al., *FEBS Letters,* 1998, 414:521-526 and Muyldermans et al., *Trends in Biochem. Sci.,* 2001, 26:230-245, each of which is incorporated by reference in its entirety. Single domain antibodies are also known as sdAbs or nanobodies. Sdabs are fairly stable and easy to express as fusion partner with the Fc chain of an antibody (Harmsen M M, De Haard H J (2007). "Properties, production, and applications of camelid single-domain antibody fragments". Appl. Microbiol Biotechnol. 77(1): 13-22).

The terms "full length antibody," "intact antibody," and "whole antibody" are used herein interchangeably to refer to an antibody having a structure substantially similar to a naturally occurring antibody structure and having heavy chains that comprise an Fc region. For example, when used to refer to an IgG molecule, a "full length antibody" is an antibody that comprises two heavy chains and two light chains.

The term "epitope" means a portion of an antigen that specifically binds to an antibody. Epitopes frequently consist of surface-accessible amino acid residues and/or sugar side chains and may have specific three dimensional structural characteristics, as well as specific charge characteristics. Conformational and non-conformational epitopes are distinguished in that the binding to the former but not the latter may be lost in the presence of denaturing solvents. An epitope may comprise amino acid residues that are directly involved in the binding, and other amino acid residues, which are not directly involved in the binding. The epitope to which an antibody binds can be determined using known techniques for epitope determination such as, for example, testing for antibody binding to AMHR2 variants with different point-mutations, or to chimeric AMHR2 variants.

A "multispecific antibody" is an antibody that comprises two or more different antigen-binding domains that collectively specifically bind two or more different epitopes. The two or more different epitopes may be epitopes on the same antigen (e.g., a single AMHR2 molecule expressed by a cell) or on different antigens (e.g., different AMHR2 molecules expressed by the same cell, or a AMHR2 molecule and a non-AMHR2 molecule). In some aspects, a multi-specific antibody binds two different epitopes (i.e., a "bispecific antibody"). In some aspects, a multi-specific antibody binds three different epitopes (i.e., a "trispecific antibody").

A "monospecific antibody" is an antibody that comprises one or more binding sites that specifically bind to a single epitope. An example of a monospecific antibody is a naturally occurring IgG molecule which, while divalent (i.e., having two antigen-binding domains), recognizes the same epitope at each of the two antigen-binding domains. The binding specificity may be present in any suitable valency.

The term "monoclonal antibody" refers to an antibody from a population of substantially homogeneous antibodies. A population of substantially homogeneous antibodies comprises antibodies that are substantially similar and that bind the same epitope(s), except for variants that may normally arise during production of the monoclonal antibody. Such variants are generally present in only minor amounts. A monoclonal antibody is typically obtained by a process that includes the selection of a single antibody from a plurality of antibodies. For example, the selection process can be the selection of a unique clone from a plurality of clones, such as a pool of hybridoma clones, phage clones, yeast clones, bacterial clones, or other recombinant DNA clones. The selected antibody can be further altered, for example, to improve affinity for the target ("affinity maturation"), to humanize the antibody, to improve its production in cell culture, and/or to reduce its immunogenicity in a subject.

"Effector functions" refer to those biological activities mediated by the Fc region of an antibody, which activities may vary depending on the antibody isotype. Examples of antibody effector functions include C1q binding to activate complement dependent cytotoxicity (CDC), Fc receptor binding to activate antibody-dependent cellular cytotoxicity (ADCC), and antibody dependent cellular phagocytosis (ADCP), receptor ligand blocking, agonism, or antagonism.

An "AMHR2 antibody," "anti-AMHR2 antibody," or "AMHR2-specific antibody" is an antibody, as provided herein, which specifically binds to the antigen AMHR2. In some embodiments, the antibody binds the extracellular domain of AMHR2. In certain embodiments, a AMHR2 antibody provided herein binds to an epitope of AMHR2 that is conserved between or among AMHR2 proteins from different species.

The term "chimeric antibody" refers to an antibody in which a portion of the heavy and/or light chain is derived from a particular source or species, while the remainder of the heavy and/or light chain is derived from a different source or species.

"Humanized" forms of non-human antibodies are chimeric antibodies that contain minimal sequence derived from the non-human antibody. A humanized antibody is generally a human antibody (recipient antibody) in which residues from one or more CDRs are replaced by residues from one or more CDRs of a non-human antibody (donor antibody). The donor antibody can be any suitable non-human antibody, such as a mouse, rat, rabbit, chicken, or non-human primate antibody having a desired specificity, affinity, or biological effect. The humanized antibody is less likely to induce an immune response, and/or induces a less severe immune response, as compared to the non-human species antibody, when it is administered to a human subject. In some instances, selected framework region residues of the recipient antibody are replaced by the corresponding framework region residues from the donor antibody. Humanized antibodies may also comprise residues that are not found in either the recipient antibody or the donor antibody. Such modifications may be made to further refine antibody function. Examples of how to make humanized antibodies can be found in U.S. Pat. Nos. 6,054,297, 5,886,152 and 5,877,293, each of which is incorporated by reference in its entirety. For further details, see Jones et al., *Nature,* 1986, 321:522-525; Riechmann et al., *Nature,* 1988, 332:323-329; and Presta, *Curr. Op. Struct. Biol.,* 1992, 2:593-596, each of which is incorporated by reference in its entirety.

In one embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen.

A "human antibody" is one which possesses an amino acid sequence corresponding to that of an antibody produced by a human or a human cell, or derived from a non-human source that utilizes a human antibody repertoire or human antibody-encoding sequences (e.g., obtained from human sources or designed de novo). Human antibodies specifically exclude humanized antibodies. In one embodiment, all of the variable and constant domains are derived from human immunoglobulin sequences (a fully human antibody). These antibodies may be prepared in a variety of ways including through the immunization with an antigen of interest of a mouse that is genetically modified to express antibodies derived from human heavy and/or light chain-encoding genes.

Methods for reducing or eliminating the antigenicity of antibodies and antibody fragments are known in the art. When the antibodies are to be administered to a human, the antibodies preferably are "humanized" to reduce or eliminate antigenicity in humans. Preferably, each humanized antibody has the same or substantially the same affinity for the antigen as the non-humanized mouse antibody from which it was derived.

In one humanization approach, chimeric proteins are created in which mouse immunoglobulin constant regions are replaced with human immunoglobulin constant regions. See, e.g., Morrison et al., 1984, PROC. NAT. ACAD. SCI. 81:6851-6855, Neuberger et al., 1984, NATURE 312:604-608; U.S. Pat. No. 6,893,625 (Robinson); U.S. Pat. No. 5,500,362 (Robinson); and U.S. Pat. No. 4,816,567 (Cabilly).

In an approach known as CDR grafting, the CDRs of the light and heavy chain variable regions are grafted into frameworks from another species. For example, murine CDRs can be grafted into human FRs. In some embodiments, the CDRs of the light and heavy chain variable regions of an antibody are grafted into human FRs or consensus human FRs. To create consensus human FRs, FRs from several human heavy chain or light chain amino acid sequences are aligned to identify a consensus amino acid sequence. CDR grafting is described in U.S. Pat. No. 7,022,500 (Queen); U.S. Pat. No. 6,982,321 (Winter); U.S. Pat. No. 6,180,370 (Queen); U.S. Pat. No. 6,054,297 (Carter); U.S. Pat. No. 5,693,762 (Queen); U.S. Pat. No. 5,859,205 (Adair); U.S. Pat. No. 5,693,761 (Queen); U.S. Pat. No. 5,565,332 (Hoogenboom); U.S. Pat. No. 5,585,089 (Queen); U.S. Pat. No. 5,530,101 (Queen); Jones et al. (1986) NATURE 321: 522-525; Riechmann et al. (1988) NATURE 332: 323-327; Verhoeyen et al. (1988) SCIENCE 239: 1534-1536; and Winter (1998) FEBS LETT 430: 92-94.

In an approach called "SUPERHUMANIZATION™," human CDR sequences are chosen from human germline genes, based on the structural similarity of the human CDRs to those of the mouse antibody to be humanized. See, e.g., U.S. Pat. No. 6,881,557 (Foote); and Tan et al., 2002, J. IMMUNOL. 169:1119-1125.

Other methods to reduce immunogenicity include "reshaping," "hyperchimerization," and "veneering/resurfacing." See, e.g., Vaswami et al., 1998, ANNALS OF ALLERGY, ASTHMA, & IMMUNOL. 81:105; Roguska et al., 1996, PROT.

ENGINEER 9:895-904; and U.S. Pat. No. 6,072,035 (Hardman). In the veneering/resurfacing approach, the surface accessible amino acid residues in the murine antibody are replaced by amino acid residues more frequently found at the same positions in a human antibody. This type of antibody resurfacing is described, e.g., in U.S. Pat. No. 5,639,641 (Pedersen).

Another approach for converting a mouse antibody into a form suitable for medical use in humans is known as ACTIVMAB™ technology (Vaccinex, Inc., Rochester, NY), which involves a vaccinia virus-based vector to express antibodies in mammalian cells. High levels of combinatorial diversity of IgG heavy and light chains can be produced. See, e.g., U.S. Pat. No. 6,706,477 (Zauderer); U.S. Pat. No. 6,800,442 (Zauderer); and U.S. Pat. No. 6,872,518 (Zauderer). Another approach for converting a mouse antibody into a form suitable for use in humans is technology practiced commercially by KaloBios Pharmaceuticals, Inc. (Palo Alto, CA). This technology involves the use of a proprietary human "acceptor" library to produce an "epitope focused" library for antibody selection. Another approach for modifying a mouse antibody into a form suitable for medical use in humans is HUMAN ENGINEERING™ technology, which is practiced commercially by XOMA (US) LLC. See, e.g., International (PCT) Publication No. WO 93/11794 and U.S. Pat. No. 5,766,886 (Studnicka); U.S. Pat. No. 5,770,196 (Studnicka); U.S. Pat. No. 5,821,123 (Studnicka); and U.S. Pat. No. 5,869,619 (Studnicka).

Any suitable approach, including any of the above approaches, can be used to reduce or eliminate human immunogenicity of an antibody.

In addition, it is possible to create fully human antibodies in mice. Fully human mAbs lacking any non-human sequences can be prepared from human immunoglobulin transgenic mice by techniques referenced in, e.g., Lonberg et al., NATURE 368:856-859, 1994; Fishwild et al., NATURE BIOTECHNOLOGY 14:845-851, 1996; and Mendez et al., NATURE GENETICS 15:146-156, 1997. Fully human monoclonal antibodies can also be prepared and optimized from phage display libraries by techniques referenced in, e.g., Knappik et al., J. MOL. BIOL. 296:57-86, 2000; and Krebs et al., J. IMMUNOL. METH. 254:67-84 2001).

In some embodiments, the antibodies provided herein comprise an antibody fragment. In some embodiments, the antibodies provided herein consist of an antibody fragment. In some embodiments, the antibodies provided herein consist essentially of an antibody fragment. In some embodiments, the antibody fragment is an Fv fragment. In some embodiments, the antibody fragment is a Fab fragment. In some embodiments, the antibody fragment is a F(ab')₂ fragment. In some embodiments, the antibody fragment is a Fab' fragment. In some embodiments, the antibody fragment is an scFv (sFv) fragment. In some embodiments, the antibody fragment is an scFv-Fc fragment. In some embodiments, the antibody fragment is a fragment of a single domain antibody.

Also included in the invention are polynucleotides encoding disclosed polypeptides or antibodies. Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)).

"Conservatively modified variants" applies to both amino acid and nucleic acid sequences. With respect to particular nucleic acid sequences, "conservatively modified variants" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of ordinary skill in the art will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of ordinary skill in the art will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the deletion of an amino acid, addition of an amino acid, or substitution of an amino acid with a chemically similar amino acid. Conservative substitution tables providing functionally similar amino acids are known to those of ordinary skill in the art. Such conservatively modified variants are in addition to and do not exclude polymorphic variants, interspecies homologs, and alleles described herein.

Conservative substitution tables providing functionally similar amino acids are known to those of ordinary skill in the art. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and [0139] 8) Cysteine (C), Methionine (M) (see, e.g., Creighton, Proteins: Structures and Molecular Properties (W H Freeman & Co.; 2nd edition (December 1993)

VH Domains

In some embodiments, an antibody provided herein comprises a VH chain comprising the sequence of SEQ ID NO:7. In some embodiments, an antibody provided herein comprises a VH chain consisting of the sequence of SEQ ID NO:7.

In some embodiments, an antibody provided herein comprises a VH chain comprising a sequence having at least about 50%, 60%, 70%, 80%, 90%, 95%, or 99% identity to an illustrative VH sequence provided in SEQ ID NO: 7. In some embodiments, an antibody provided herein comprises a VH sequence provided in SEQ ID NO: 7, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

VL Domains

In some embodiments, an antibody provided herein comprises a VL chain comprising a sequence of SEQ ID NO: 8.

In some embodiments, an antibody provided herein comprises a VL chain comprising a sequence having at least about 50%, 60%, 70%, 80%, 90%, 95%, or 99% identity to an illustrative VL sequence provided in SEQ ID NO: 8. In some embodiments, an antibody provided herein comprises a VL sequence provided in SEQ ID NO: 8, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

VH-VL Combinations

In some embodiments, an antibody provided herein comprises a VH chain comprising a sequence of SEQ ID NO: 7 and a VL chain comprising a sequence of SEQ ID NO: 8. In some embodiments, an antibody provided herein comprises a VH chain comprising a sequence provided in SEQ ID NO: 7, with up to 1, 2, 3, 4, 5, 6, 7, 8, 9, 10, 11, 12, 13, 14, 15, 16, 17, 18, 19, 20, 21, 22, 23, 24, or 25 amino acid substitutions, and a VL chain comprising a sequence provided in SEQ ID NO: 8, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

CDRs

In some embodiments, an antibody provided herein comprises one to three CDRs of a VH domain selected from SEQ ID NO: 7. In some embodiments, an antibody provided herein comprises two to three CDRs of a VH domain selected from SEQ ID NO: 7. In some embodiments, an antibody provided herein comprises three CDRs of a VH domain selected from SEQ ID NO: 7.

In some embodiments, the CDRs are CDRs having at least about 50%, 75%, 80%, 85%, 90%, or 95% identity with a CDR-H1, CDR-H2, or CDR-H3 of SEQ ID NO: 7. In some embodiments, the CDR-H1 is a CDR-H1 of a VH domain selected from SEQ ID NO: 7, with up to 1, 2, 3, 4, or 5 amino acid substitutions. In some embodiments, the CDR-H2 is a CDR-H2 of a VH domain selected from SEQ ID NO: 7, with up to 1, 2, 3, 4, 5, 6, 7, or 8 amino acid substitutions. In some embodiments, the CDR-H3 is a CDR-H3 of a VH domain selected from SEQ ID NO: 7, with up to 1, 2, 3, 4, 5, 6, 7, or 8 amino acid substitutions. In some embodiments, the CDRs are CDRs having at least about 50%, 75%, 80%, 85%, 90%, or 95% identity with a CDR-L1, CDR-L 2, or CDR-L 3 of SEQ ID NO: 8. In some embodiments, the CDR-L1 is a CDR-L1 of a VH domain selected from SEQ ID NO: 7, with up to 1, 2, 3, 4, or 5 amino acid substitutions. In some embodiments, the CDR-L2 is a CDR-L2 of a VH domain selected from SEQ ID NO: 8, with up to 1, 2, 3, 4, 5, 6, 7, or 8 amino acid substitutions. In some embodiments, the CDR-L3 is a CDR-L3 of a VL domain selected from SEQ ID NO: 8, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 selected of SEQ ID NO: 3. In some aspects, the CDR-H3 has at least about 50%, 75%, 80%, 85%, 90%, or 95% identity with a CDR-H3 of SEQ ID NO: 3. In some embodiments, the CDR-H3 is a CDR-H3 selected of SEQ ID NO: 3, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H2 of SEQ ID NO: 2. In some aspects, the CDR-H2 has at least about 50%, 75%, 80%, 85%, 90%, or 95% identity with a CDR-H2 of SEQ ID NO: 2. In some embodiments, the CDR-H2 is a CDR-H2 of SEQ ID NO: 2, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H1 of SEQ ID NO: 1. In some aspects, the CDR-H1 has at least about 50%, 75%, 80%, 85%, 90%, or 95% identity with a CDR-H1 of SEQ ID NO: 1. In some embodiments, the CDR-H1 is a CDR-H1 of SEQ ID NO: 1, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 of SEQ ID NO: 3 and a CDR-H2 of SEQ ID NO: 2. In some embodiments, an antibody provided herein comprises a CDR-H3 of SEQ ID NO: 3, a CDR-H2 of SEQ ID NO: 2, and a CDR-H1 of SEQ ID NO: 1. In some embodiments, the CDR-H3 has at least about 50%, 75%, 80%, 85%, 90%, or 95% identity with a CDR-H3 of SEQ ID NO: 3, the CDR-H2 has at least about 50%, 75%, 80%, 85%, 90%, or 95% identity with a CDR-H2 of SEQ ID NO: 2, and the CDR-H1 has at least about 50%, 75%, 80%, 85%, 90%, or 95% identity with a CDR-H1 of SEQ ID NO: 1. In some embodiments, the CDR-H3 is a CDR-H3 of SEQ ID NO: 3, with up to 1, 2, 3, 4, 5, 6, 7, or 8 amino acid substitutions; the CDR-H2 is a CDR-H2 of SEQ ID NO: 2, with up to 1, 2, 3, 4, 5, 6, 7, or 8 amino acid substitutions; and the CDR-H1 is a CDR-H1 of SEQ ID NO: 1, with up to 1, 2, 3, 4, or 5 amino acid substitutions. In some aspects, the amino acid substitutions are conservative amino acid substitutions. In some embodiments, the antibody described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-L3 of SEQ ID NO: 6. In some aspects, the CDR-L3 has at least about 50%, 75%, 80%, 85%, 90%, or 95% identity with a CDR-L3 of SEQ ID NO: 6. In some embodiments, the CDR-L3 is a CDR-L3 of SEQ ID NO: 6, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-L2 of SEQ ID NO: 5. In some aspects, the CDR-L2 has at least about 50%, 75%, 80%, 85%, 90%, or 95% identity with a CDR-L2 of SEQ ID NO: 5. In some embodiments, the CDR-L2 is a CDR-L2 of SEQ ID NO: 5, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-L1 of SEQ ID NO: 4. In some aspects, the CDR-L1 has at least about 50%, 75%, 80%, 85%, 90%, or 95% identity with a CDR-L1 of SEQ ID NO: 4. In some embodiments, the CDR-L1 is a CDR-L1 of SEQ ID NO: 4, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-L3 of SEQ ID NO: 6 and a CDR-L2 of SEQ ID NO: 5. In some embodiments, an antibody provided herein comprises a CDR-L3 of SEQ ID NO: 6, a CDR-L2 of SEQ ID NO: 5, and a CDR-L1 of SEQ ID NO: 4. In some embodiments, the CDR-L3 has at least about 50%, 75%, 80%, 85%, 90%, or 95% identity with a CDR-L3 of SEQ ID NO: 6, the CDR-L2 has at least about 50%, 75%, 80%, 85%, 90%, or 95% identity with a CDR-L2 of SEQ ID NO: 5, and the CDR-L1 has at least about 50%, 75%, 80%, 85%, 90%, or 95% identity with a CDR-L1 of SEQ ID NO: 4. In some embodiments, the CDR-L3 is a CDR-L3 of SEQ ID NO: 6, with up to 1, 2, 3, 4, or 5 amino acid substitutions; the CDR-L2 is a CDR-L2 of SEQ ID NO: 5, with up to 1, 2, 3, or 4 amino acid substitutions; and the CDR-L1 is a CDR-L1 of SEQ ID NO: 4, with up to 1, 2, 3, 4, 5, or 6 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 of SEQ ID NO: 3, a CDR-H2 of SEQ ID NO: 2, a CDR-H1 of SEQ ID NO: 1, a CDR-L3 of SEQ ID NO: 6, a CDR-L2 of SEQ ID NO: 5, and a CDR-L1 of SEQ ID NO: 4. In some embodiments, the CDR-H3 has at least about 50%, 75%, 80%, 85%, 90%, or 95% identity with a CDR-H3 of SEQ ID NO: 3, the CDR-H2 has at least about 50%, 75%, 80%, 85%, 90%, or 95% identity with a CDR-H2 of SEQ ID NO: 2, the CDR-H1 has at least about 50%, 75%, 80%, 85%, 90%, or 95% identity with a CDR-H1 of SEQ ID NO: 1, the CDR-L3 has at least about 50%, 75%, 80%, 85%, 90%, or 95% identity with a CDR-L3 of SEQ ID NO: 6, the CDR-L2 has at least about 50%, 75%, 80%, 85%, 90%, or 95% identity with a CDR-L2 of SEQ ID NO: 5, and the CDR-L1 has at least about 50%, 75%, 80%, 85%, 90%, or 95% identity with a CDR-L1 of SEQ ID NO: 4. In some embodiments, the CDR-H3 is a CDR-H3 of SEQ ID NO: 3, with up to 1, 2, 3, 4, 5, 6, 7, or 8 amino acid substitutions; the CDR-H2 is a CDR-H2 of SEQ ID NO: 2, with up to 1, 2, 3, 4, 5, 6, 7, or 8 amino acid substitutions; the CDR-H1 is a CDR-H1 of SEQ ID NO: 1, with up to 1, 2, 3, 4, or 5 amino acid substitutions; the CDR-L3 is a CDR-L3 of SEQ ID NO: 6, with up to 1, 2, 3, 4, or 5 amino acid substitutions; the CDR-L2 is a CDR-L2 of SEQ ID NO: 5, with up to 1, 2, 3, or 4 amino acid substitutions; and the CDR-L1 is a CDR-L1 of SEQ ID NO: 4, with up to 1, 2, 3, 4, 5, or 6 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H1 of SEQ ID NO: 1, a CDR-H2 of SEQ ID NO: 2, a CDR-H3 of SEQ ID NO: 3, a CDR-L1 of SEQ ID NO: 4, a CDR-L2 of SEQ ID NO: 5, and a CDR-L1 of SEQ ID NO: 6.

Fc Region

The term "Fc domain" or "Fc region" herein is used to define a C-terminal region of an immunoglobulin heavy chain that contains at least a portion of the constant region. The term includes native sequence Fc regions and variant Fc regions. Unless otherwise specified herein, numbering of amino acid residues in the Fc region or constant region is according to the EU numbering system, also called the EU index, as described in Kabat et al, Sequences of Proteins of Immunological Interest, 5th Ed. Public Health Service, National Institutes of Health, Bethesda, MD, 1991. An "Fc polypeptide" of a dimeric Fc as used herein refers to one of the two polypeptides forming the dimeric Fc domain, i.e. a polypeptide comprising C-terminal constant regions of an immunoglobulin heavy chain, capable of stable self-association. For example, an Fc polypeptide of a dimeric IgG Fc comprises an IgG CH2 and an IgG CH3 constant domain sequence. An Fc can be of the class IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$.

The terms "Fc receptor" and "FcR" are used to describe a receptor that binds to the Fc region of an antibody. For example, an FcR can be a native sequence human FcR. Generally, an FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Immunoglobulins of other isotypes can also be bound by certain FcRs (see, e.g., Janeway et al., Immuno Biology: the immune system in health and disease, (Elsevier Science Ltd., NY) (4th ed., 1999)). Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (reviewed in Daeron, Annu. Rev. Immunol. 15:203-234 (1997)). FcRs are reviewed in Ravetch and Kinet, Annu.

Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976); and Kim et al., J. Immunol. 24:249 (1994)).

In some embodiments, an antibody is an IgG1 antibody. In some embodiments, an antibody is an IgG3 antibody. In some embodiments, an antibody is an IgG2 antibody. In some embodiments, an antibody is an IgG4 antibody.

Modifications in the CH2 domain can affect the binding of FcRs to the Fc. A number of amino acid modifications in the Fc region are known in the art for selectively altering the affinity of the Fc for different Fc-gamma (Fcγ) receptors. In one embodiment, the Fc comprises one or more modifications to promote selective binding of Fc-gamma receptors.

Exemplary mutations that alter the binding of FcRs to the Fc are listed below:

S298A/E333A/K334A, S298A/E333A/K334A/K326A (Lu Y, Vernes J M, Chiang N, et al. J Immunol Methods. 2011 Feb. 28; 365(1-2):132-41);

F243L/R292P/Y300L/V305I/P396L, F243L/R292P/Y300L/L235V/P396L (Stavenhagen J B, Gorlatov S, Tuaillon N, et al. Cancer Res. 2007 Sep. 15; 67(18): 8882-90; Nordstrom J L, Gorlatov S, Zhang W, et al. Breast Cancer Res. 2011 Nov. 30; 13(6):R123);

F243L (Stewart R, Thom G, Levens M, et al. Protein Eng Des Sel. 2011 September; 24(9):671-8.), S298A/E333A/K334A (Shields R L, Namenuk A K, Hong K, et al. J Biol Chem. 2001 Mar. 2; 276(9):6591-604);

S239D/I332E/A330L, S239D/I332E (Lazar G A, Dang W, Karki S, et al. Proc Natl Acad Sci USA. 2006 Mar. 14; 103(11):4005-10);

S239D/S267E, S267E/L328F (Chu S Y, Vostiar I, Karki S, et al. Mol Immunol. 2008 September; 45(15):3926-33);

S239D/D265S/S298A/I332E, S239E/S298A/K326A/A327H, G237F/S298A/A330L/I 332E, S239D/I332E/S298A, S239D/K326E/A330L/I332E/S298A, G236A/S239D/D270L/I3 32E, S239E/S267E/H268D, L234F/S267E/N325L, G237F/V266L/S267D and other mutations listed in WO2011/120134 and WO2011/120135, herein incorporated by reference. *Therapeutic Antibody Engineering* (by William R. Strohl and Lila M. Strohl, Woodhead Publishing series in Biomedicine No 11, ISBN 1 907568 37 9, October 2012) lists mutations on page 283.

In some embodiments an antibody described herein includes modifications to improve its ability to mediate effector function. Such modifications are known in the art and include afucosylation, or engineering of the affinity of the Fc towards an activating receptor, mainly FCGR3a for ADCC, and towards C1q for CDC. The Table B, below, summarizes various designs reported in the literature for effector function engineering.

In certain embodiments, an antibody provided herein comprises an Fc region with one or more amino acid substitutions which improve ADCC, such as a substitution at one or more of positions 298, 333, and 334 of the Fc region. In some embodiments, an antibody provided herein comprises an Fc region with one or more amino acid substitutions at positions 239, 332, and 330, as described in Lazar et al., Proc. Natl. Acad. Sci. USA, 2006, 103:4005-4010, incorporated by reference in its entirety.

In some embodiments, an antibody provided herein comprises one or more alterations that improves or diminishes C1q binding and/or CDC. See U.S. Pat. No. 6,194,551; WO 99/51642; and Idusogie et al., *J. Immunol.*, 2000, 164:4178-4184; each of which is incorporated by reference in its entirety.

Thus, in one embodiment, an antibody described herein can include a dimeric Fc that comprises one or more amino acid modifications as noted in Table B that confer improved effector function. In another embodiment, the antibody can be afucosylated to improve effector function.

TABLE B

| Table B: CH2 domains and effector function engineering | | |
|---|---|---|
| Reference | Mutations | Effect |
| Lu, 2011, Ferrara 2011, Mizushima 2011 | Afucosylated | Increased ADCC |
| Lu, 2011 | S298A/E333A/K334A | Increased ADCC |
| Lu, 2011 | S298A/E333A/K334A/K326A | Increased ADCC |
| Stavenhagen, 2007 | F243L/R292P/Y300L/V305I/P396L | Increased ADCC |
| Nordstrom, 2011 | F243L/R292P/Y300L/L235V/P396L | Increased ADCC |
| Stewart, 2011 | F243L | Increased ADCC |
| Shields, 2001 | S298A/E333A/K334A | Increased ADCC |
| Lazar, 2006 | S239D/I332E/A330L | Increased ADCC |
| Lazar, 2006 | S239D/I332E | Increased ADCC |
| Bowles, 2006 | AME-D, not specified mutations | Increased ADCC |
| Heider, 2011 | 37.1, mutations not disclosed | Increased ADCC |
| Moore, 2010 | S267E/H268F/S324T | Increased CDC |

Methods of producing antibodies with little or no fucose on the Fe glycosylation site (Asn 297 EU numbering) without altering the amino acid sequence are well known in the art. The GlymaxX® technology (ProBioGen AG) is based on the introduction of a gene for an enzyme which deflects the cellular pathway of fucose biosynthesis into cells used for antibody production. This prevents the addition of the sugar "fucose" to the N-linked antibody carbohydrate part by antibody-producing cells. (von Horsten et al. (2010) Glycobiology. 2010 December; 20 (12):1607-18.) Examples of cell lines capable of producing defucosylated antibody include CHO-DG44 with stable overexpression of the bacterial oxidoreductase GDP-6-deoxy-D-lyxo-4-hexylose reductase (RMD) (see Henning von Horsten et al., Glycobiol 2010, 20:1607-1618) or Lec13 CHO cells, which are deficient in protein fucosylation (see Ripka et al., Arch. Biochem. Biophys., 1986, 249:533-545; U.S. Pat. Pub. No. 2003/0157108; WO 2004/056312; each of which is incorporated by reference in its entirety), and knockout cell lines, such as alpha-1,6-fucosyltransferase gene or FUT8 knockout CHO cells (see Yamane-Ohnuki et al., Biotech. Bioeng., 2004, 87: 614-622; Kanda et al., Biotechnol. Bioeng., 2006, 94:680-688; and WO 2003/085107; each of which is incorporated by reference in its entirety). Another approach to obtaining antibodies with lowered levels of fucosylation can be found in U.S. Pat. No. 8,409,572, which teaches selecting cell lines for antibody production for their ability to yield lower levels of fucosylation on antibodies Antibodies can be fully afucosylated (meaning they contain no detectable fucose) or they can be partially afucosylated, meaning that the isolated antibody contains less than 95%, less than 85%, less than 75%, less than 65%, less than 55%, less than 45%, less than 35%, less than 25%, less than 15% or less than 5% of the amount of fucose normally detected for a similar antibody produced by a mammalian expression system.

In some aspects, an antibody provided herein comprises an IgG1 domain with reduced fucose content at position Asn 297 compared to a naturally occurring IgG1 domain. Such Fc domains are known to have improved ADCC. See Shields et al., J. Biol. Chem., 2002, 277:26733-26740, incorporated by reference in its entirety. In some aspects, such antibodies do not comprise any fucose at position Asn 297. The amount of fucose may be determined using any suitable method, for example as described in WO 2008/077546, incorporated by reference in its entirety.

In some embodiments, an antibody provided herein comprises a bisected oligosaccharide, such as a biantennary oligosaccharide attached to the Fc region of the antibody that is bisected by GlcNAc. Such antibody variants may have reduced fucosylation and/or improved ADCC function. Examples of such antibody variants are described, for example, in WO 2003/011878; U.S. Pat. No. 6,602,684; and U.S. Pat. Pub. No. 2005/0123546; each of which is incorporated by reference in its entirety.

Other illustrative glycosylation variants which may be incorporated into the antibodies provided herein are described, for example, in U.S. Pat. Pub. Nos. 2003/0157108, 2004/0093621, 2003/0157108, 2003/0115614, 2002/0164328, 2004/0093621, 2004/0132140, 2004/0110704, 2004/0110282, 2004/0109865; International Pat. Pub. Nos. 2000/61739, 2001/29246, 2003/085119, 2003/084570, 2005/035586, 2005/035778; 2005/053742, 2002/031140; Okazaki et al., J. Mol. Biol., 2004, 336:1239-1249; and Yamane-Ohnuki et al., Biotech. Bioeng., 2004, 87: 614-622; each of which is incorporated by reference in its entirety.

In some embodiments, an antibody provided herein comprises an Fc region with at least one galactose residue in the oligosaccharide attached to the Fc region. Such antibody variants may have improved CDC function. Examples of such antibody variants are described, for example, in WO 1997/30087; WO 1998/58964; and WO 1999/22764; each of which his incorporated by reference in its entirety.

Examples of cell lines capable of producing defucosylated antibodies include CHO-DG44 with stable overexpression of the bacterial oxidoreductase GDP-6-deoxy-D-lyxo-4-hexylose reductase (RMD) (see Henning von Horsten et al., Glycobiol 2010, 20:1607-1618) or Lec13 CHO cells, which are deficient in protein fucosylation (see Ripka et al., Arch. Biochem. Biophys., 1986, 249:533-545; U.S. Pat. Pub. No. 2003/0157108; WO 2004/056312; each of which is incorporated by reference in its entirety), and knockout cell lines, such as alpha-1,6-fucosyltransferase gene or FUT8 knockout CHO cells (see Yamane-Ohnuki et al., Biotech. Bioeng., 2004, 87: 614-622; Kanda et al., Biotechnol. Bioeng., 2006, 94:680-688; and WO 2003/085107; each of which is incorporated by reference in its entirety).

In some embodiments, an antibody has antibody-dependent cellular phagocytosis (ADCP) activity. ADCP can occur when antibodies bind to antigens on the surface of pathogenic or tumorigenic target-cells. Phagocytic cells bearing Fc receptors on their cell surface, including monocytes and macrophages, recognize and bind the Fc region of antibodies bound to target-cells. Upon binding of the Fc receptor to the antibody-bound target cell, phagocytosis of the target cell can be initiated. ADCP can be considered a form of ADCC.

In some embodiments, the antibodies are capable of forming an immune complex. For example, an immune complex can be a tumor cell covered by antibodies.

In some embodiments the antibodies are monoclonal antibodies.

In some embodiments the antibodies are polyclonal antibodies.

In some embodiments the antibodies are produced by hybridomas. In other embodiments, the antibodies are produced by recombinant cells engineered to express the desired variable and constant domains.

In some embodiments the antibodies may be single chain antibodies or other antibody derivatives retaining the antigen specificity and the lower hinge region or a variant thereof.

In some embodiments the antibodies may be polyfunctional antibodies, recombinant antibodies, human antibodies, humanized antibodies, fragments or variants thereof. In particular embodiments, the antibody fragment or a derivative thereof is selected from a Fab fragment, a Fab'2 fragment, a CDR and ScFv.

In some embodiments, antibodies are specific for surface antigens, such as AMHR2 protein. In some embodiments, therapeutic antibodies are specific for tumor antigens (e.g., molecules specifically expressed by tumor cells). In particular embodiments, the therapeutic antibodies may have human or non-human primate IgG1 or IgG3 Fc portions.

Binding

With regard to the binding of an antibody to a target molecule, the terms "bind," "specific binding," "specifically binds to," "specific for," "selectively binds," and "selective for" a particular antigen (e.g., a polypeptide target) or an epitope on a particular antigen mean binding that is measurably different from a non-specific or non-selective interaction (e.g., with a non-target molecule). Specific binding can be measured, for example, by measuring binding to a target molecule and comparing it to binding to a non-target molecule. Specific binding can also be determined by competition with a control molecule that mimics the epitope recognized on the target molecule. In that case, specific binding is indicated if the binding of the antibody to the target molecule is competitively inhibited by the control molecule.

"Affinity" refers to the strength of the sum total of non-covalent interactions between a single binding site of a molecule (e.g., an antibody) and its binding partner (e.g., an antigen or epitope). Unless indicated otherwise, as used herein, "affinity" refers to intrinsic binding affinity, which reflects a 1:1 interaction between members of a binding pair (e.g., antibody and antigen or epitope). The affinity of a molecule X for its partner Y can be represented by the dissociation equilibrium constant ($K_D$). The kinetic components that contribute to the dissociation equilibrium constant are described in more detail below. Affinity can be measured by common methods known in the art, including those described herein, such as surface plasmon resonance (SPR) technology (e.g., BIACORE®) or biolayer interferometry (e.g., FORTEBIO®).

The term "$k_d$" ($sec^{-1}$), as used herein, refers to the dissociation rate constant of a particular antibody-antigen interaction. This value is also referred to as the $k_{off}$ value.

The term "$k_a$" ($M^{-1} \times sec^{-1}$), as used herein, refers to the association rate constant of a particular antibody-antigen interaction. This value is also referred to as the $k_{on}$ value.

The term "$K_D$" (M), as used herein, refers to the dissociation equilibrium constant of a particular antibody-antigen interaction. $K_D=k_d/k_a$. In some embodiments, the affinity of an antibody is described in terms of the $K_D$ for an interaction between such antibody and its antigen. For clarity, as known in the art, a smaller $K_D$ value indicates a higher affinity interaction, while a larger $K_D$ value indicates a lower affinity interaction.

The term "$K_A$" ($M^{-1}$), as used herein, refers to the association equilibrium constant of a particular antibody-antigen interaction. $K_A=k_a/k_d$.

In some embodiments, an antibody provided herein binds human AMHR2 with a $K_D$ of less than or equal to about 0.001, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 1.95, 2, 3, 4, 5, 6, 7, 8, 9, or $10 \times 10^{-9}$ M, as measured by Biacore assay. In some embodiments, the $K_D$ of the antibody provided herein is between about 0.001-0.01, 0.01-0.1, 0.01-0.05, 0.05-0.1, 0.1-0.5, 0.5-1, 0.25-0.75, 0.25-0.5, 0.5-0.75, 0.75-1, 0.75-2, 1.1-1.2, 1.2-1.3, 1.3-1.4, 1.4-1.5, 1.5-1.6, 1.6-1.7, 1.7-1.8, 1.8-1.9, 1.9-2, 1-2, 1-5, 2-7, 3-8, 3-5, 4-6, 5-7, 6-8, 7-9, 7-10, or $5-10 \times 10^{-9}$ M, as measured by Biacore assay.

In some embodiments, the antibody provided herein binds human AMHR2 with a $K_D$ of less than or equal to about 2, 1.98, 1.95, 1.9, 1.85, 1.8, 1.75, 1.7, 1.65, 1.6, 1.55, 1.50, 1.45, or $1.4 \times 10^{-9}$ M, or less, as measured by Biacore assay. In some embodiments, the antibody provided herein binds human AMHR2 with a $K_D$ between 1.9-1.8, 1.8-1.7, 1.7-1.6, 1.6-1.5, or $1.9-1.5 \times 10^{-9}$ M as measured by Biacore assay. In some embodiments, the antibody provided herein binds human AMHR2 with a $K_a$ of less than or equal to about 10, 9.56, 9.5, 9.0, 8.88, 8.84, 8.5, 8, 7.5, 7.32, 7, 6.5, 6, 5.5, 5, 4.5, 4, 3.5, 3, 2.5, 2, 1.5, or $1 \times 10^{-4}$ (1/s), or less, as measured by Biacore assay. In some embodiments, the antibody provided herein binds human AMHR2 with a $K_d$ between 7-10, 7-8, 8-9, 9-10, 7-7.5, 7.5-8, 8.-8.5, 8.5-9, 9-9.5, or $9.5-10 \times 10^{-4}$ (1/s) as measured by Biacore assay. In some embodiments, the antibody provided herein binds human AMHR2 with a $K_a$ of greater than or equal to about 4, 4.1, 4.2, 4.3, 4.4, 4.5, 4.6, 4.7, 4.8, 4.9, 45, 5.1, 5.2, 5.3, 5.4, 5.5, 5.6, 5.7, 5.8, 5.9, 6, 7, 8, 9, or $10 \times 10^5$ (1/Ms), or more, as measured by Biacore assay. In some embodiments, the antibody provided herein binds human AMHR2 with a $K_a$ between 4-7, 4-4.5, 4.5-5, 5-5.5, 5.5-6, 6-6.5, or 6.5-7, 7-8, 8-9, or $9-10 \times 10^5$ (1/Ms) as measured by Biacore assay.

To screen for antibodies which bind to an epitope on a target antigen bound by an antibody of interest (e.g., AMHR2), a routine cross-blocking assay such as that described in *Antibodies, A Laboratory Manual*, Cold Spring Harbor Laboratory, Ed Harlow and David Lane (1988), can be performed. Alternatively, or additionally, epitope mapping can be performed by methods known in the art.

When used herein in the context of two or more antibodies, the term "competes with" or "cross-competes with" indicates that the two or more antibodies compete for binding to an antigen (e.g., AMHR2). In one exemplary assay, AMHR2 or AMHR2-extracellular domain (AMHR2-ED) is coated on a surface and contacted with a first AMHR2 antibody, after which a second AMHR2 antibody is added. In another exemplary assay, a first AMHR2 antibody is coated on a surface and contacted with AMHR2 or AMHR2-ED, and then a second AMHR2 antibody is added. If the presence of the first AMHR2 antibody reduces binding of the second AMHR2 antibody, in either assay, then the antibodies compete with each other. The term "competes with" also includes combinations of antibodies where one antibody reduces binding of another antibody, but where no competition is observed when the antibodies are added in the reverse order. However, in some embodiments, the first and second antibodies inhibit binding of each other, regardless of the order in which they are added. In some embodiments, one antibody reduces binding of another antibody to its antigen by at least 25%, at least 50%, at least 60%, at least 70%, at least 80%, at least 85%, at least 90%, or at least 95%. A skilled artisan can select the concentrations of the antibodies used in the competition assays based on the affinities of the antibodies for AMHR2 and the valency of the antibodies. The assays described in this definition are illustrative, and a skilled artisan can utilize any suitable assay to determine if antibodies compete with each other. Suitable assays are described, for example, in Cox et al., "Immunoassay Methods," in *Assay Guidance Manual* [*Internet*], Updated Dec. 24, 2014 (www.ncbi.nlm.nih.gov/books/NBK92434/; accessed Sep. 29, 2015); Silman et al., *Cytometry,* 2001, 44:30-37; and Finco et al., *J. Pharm. Biomed. Anal.,* 2011, 54:351-358; each of which is incorporated by reference in its entirety.

Competition between antibodies can be determined by an assay in which an antibody under test inhibits or blocks specific binding of a reference antibody to a common antigen (see, e.g., Junghans et al., Cancer Res. 50:1495, 1990; Fendly et al. Cancer Research 50: 1550-1558; U.S. Pat. No. 6,949,245). A test antibody competes with a reference antibody if an excess of a test antibody (e.g., at least 2×, 5×, 10×, 20×, or 100×) inhibits or blocks binding of the reference antibody by, e.g., at least 50%, 60%, 70%, 75%, 80%, 85%, 90%, 95%, or 99% as measured in a competitive binding assay. Antibodies identified by competition assay (competing antibody) include antibodies binding to the same epitope as the reference antibody and antibodies binding to an adjacent epitope sufficiently proximal to the epitope bound by the reference antibody for steric hindrance to occur. For example, a second, competing antibody can be identified that competes for binding to AMHR2 with a first antibody described herein. In certain instances, the second antibody can block or inhibit binding of the first antibody by, e.g., at least 50%, 60%, 70%, 75%, 80%, 85%, 90%, 95%, or 99% as measured in a competitive binding assay. In certain instances, the second antibody can displace the first antibody by greater than 50%, 60%, 70%, 75%, 80%, 85%, 90%, 95%, or 99%.

Function

In some embodiments, the antibody induces programmed cell death. In some embodiments, the programmed cell death is apoptosis. In some embodiments, the programmed cell death is mediated by caspase-3. In some embodiments, the apoptosis is mediated by caspase-3. In some embodiments, the antibody induces cleavage of PARP-1 in the cell. In some embodiments, the antibody is internalized by the cell.

Programmed cell death is the death of a cell and is mediated by an intracellular program. Apoptosis and autophagy are forms of programmed cell death initiated by the cell. Necrosis is a form of cell death caused by external factors, such as trauma or infection. Apoptosis is initiated via caspase-dependent pathways via either the intrinsic pathway or the extrinsic pathway. Intrinsic apoptosis is typically initiated by perturbation of the extracellular or intracellular microenvironment. Extrinsic apoptosis is typically initiated by perturbation of the extracellular microenvironment via receptor-based detection. Both pathways are precipitated by caspase-3 (CASP3). An overview of cell death, including programmed cell death, is provided in Galluzzi L et al., *Cell Death & Differentiation* volume 25, pages 486-541(2018) which is incorporated by reference in its entirety.

In some embodiments, the antibody has antibody-dependent cellular cytotoxicity (ADCC) activity. ADCC can occur when antibodies bind to antigens on the surface of pathogenic or tumorigenic target-cells. Effector cells bearing Fc gamma receptors (FcγR or FCGR) on their cell surface, including cytotoxic T-cells, natural killer (NK) cells, macrophages, neutrophils, eosinophils, dendritic cells, or monocytes, recognize and bind the Fc region of antibodies bound to the target-cells. Such binding can trigger the activation of intracellular signaling pathways leading to cell death. In particular embodiments, the antibody's immunoglobulin Fc region subtypes (isotypes) include human IgG1 and IgG3. As used herein, ADCC refers to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al., *Proc. Natl. Acad. Sci.* (*USA*) 95:652-656 (1998).

In some embodiments, the antibody has complement-dependent cytotoxicity (CDC) activity. Antibody-induced CDC is mediated through the proteins of the classical complement cascade and is triggered by binding of the complement protein C1q to the antibody. Antibody Fc region binding to C1q can induce activation of the complement cascade. In particular embodiments, the antibody's immunoglobulin Fc region subtypes (isotypes) include human IgG1 and IgG3. As used herein, CDC refers to the ability of a molecule to lyse a target in the presence of complement. The complement activation pathway is initiated by the binding of the first component of the complement system (C1q) to a molecule (e.g. polypeptide (e.g., an antibody)) complexed with a cognate antigen. To assess complement activation, a CDC assay, e.g. as described in Gazzano-Santoro et al., *J. Immunol. Methods* 202:163 (1996), may be performed.

In some embodiments an antibody is a depleting antibody. A depleting antibody is one that would kill an AMHR2-expressing cancer cell upon contact through the antibody's interaction with other immune cells of molecules. For example, antibodies, when bound to cells bearing AMHR2 proteins, could engage complement proteins and induce complement-dependent cell lysis. Antibodies, when bound to cells bearing AMHR2 proteins, could also trigger neighboring cells bearing Fc receptors to kill them by antibody-dependent cellular cytotoxicity (ADCC).

In some embodiments, an antibody is an agonistic antibody. An agonistic antibody can induce (e.g., increase) one or more activities or functions of AMHR2-expressing cells after the antibody binds a AMHR2 protein expressed on the cell. The agonistic antibody may bind to and activate AMHR2-expressing cells, causing changes in proliferation of the cell or modifying antigen presentation capabilities.

The agonistic antibody may bind to and activate AMHR2-expressing cells, triggering intracellular signaling pathways that lead to modified cell growth or apoptosis. In some embodiments, binding of an anti-AMHR2 antibody to AMHR2 may induce cell cycle arrest and programmed cell death.

In some embodiments, an antibody is an antagonistic antibody. An antagonistic antibody can block (e.g. decrease) one or more activities or functions of AMHR2-expressing cells after the antibody binds a TREM2 protein expressed on the cell. For example, the antagonist antibody may bind to and block ligand binding to one or more AMHR2-expressing cell proteins, preventing differentiation and proliferation of the cell or modifying antigen presentation capabilities. The antagonist antibody may bind to and prevent activation of a AMHR2 protein by its ligand, modifying intracellular signaling pathways that contribute to cell growth and survival.

In some embodiments, an anti-AMHR2 antibody is a receptor ligand blocking antibody. A receptor blocking antibody binds to the extracellular domain of AMHR2 and blocks binding of the cognate AMHR2 ligand AMH. In some embodiments, blocking of the ligand binding can prevent activation of the AMHR2 signaling pathway.

In one embodiment an anti-AMHR2 antibody bound to its target is responsible for causing the in vivo depletion of cancer cells to which it is bound. In some embodiments, effector proteins induced by clustered antibodies can trigger a variety of responses, including release of inflammatory cytokines, regulation of antigen production, endocytosis, or cell killing. In one embodiment the antibody is capable of recruiting and activating complement (CDC) or mediating antibody-dependent cellular cytotoxicity (ADCC) in vivo, or mediating phagocytosis (ADCP) by binding Fc receptors in vivo. The antibody may also deplete AMHR2+ cancer cells by inducing apoptosis or necrosis of the AMHR2+ cancer cell upon binding.

III. Vaccines, Adjuvants and Formulations

In another aspect, provided herein are compositions, for example, compositions comprising an AMHR2 extracellular domain polypeptide, that induce immune responses comprising both type-1 and type-17 T cells while inducing limited or no toxicity.

T cells that mediate adaptive immune responses are divided into subsets according to their cytokine profiles. Type-1 proinflammatory T cells produce IFNγ and mediate immunity against viral and bacterial infections, whereas type-2 regulatory T cells produce Interleukin (IL)-4, IL-5, and IL-13 and mediate humoral immunity against parasitic infections. Recent studies established type-17 proinflammatory T cells which produce IL-17, as a distinct subtype that also plays a prominent role in inflammation. Both type-1 and type-17 T-cell lineages are needed to induce optimized tissue damage against self-proteins (Steinman et al., (2007) Nat Med 13:139-145; Luger et al., (2008) J Exp Med 205:799-810).

Anti-cancer vaccines are designed to stimulate the immune system to attack cancer cells. These vaccines typically include an antigen preferentially expressed by cancer cells ("tumor-associated antigens"). Most current clinical vaccine formulations induce pro-inflammatory type-1 immunity but little, if any, type-17 immunity. The present invention encompasses the insight that many current clinical vaccine formulations are not effective because they do not elicit both type-1 and type-17 immune responses. In accordance with the present invention, provided compositions induce immune responses comprising both type-1 and type-17 proinflammatory T cells. Moreover, presently disclosed compositions induce limited or no toxicity when injected into animal models, suggesting their suitability for human clinical use.

The present invention encompasses vaccine formulations that induce an adaptive immune response effective to inhibit and/or prevent cancer growth. In some embodiments, the cancer is ovarian cancer. Presently disclosed compositions comprise an AMHR2 extracellular domain polypeptide antigen and adjuvant components as described further herein. In some embodiments, the composition further comprises an anti-AMHR2 antibody. Therefore, the presently disclosed vaccine formulations, compositions, and methods, may be useful in treating and/or preventing the ovarian cancers.

As described herein, the present disclosure involves an immunogen/adjuvant combination that induces an adaptive immune response (e.g., type-1 and type-17 T cells) for inhibiting cancer, such as ovarian cancer, growth. In some aspects, the compositions comprise an AMHR2 extracellular domain polypeptide and zymosan. In some aspects, the compositions comprise an AMHR2 extracellular domain polypeptide and MONTANIDE™. In some aspects, the compositions comprise an AMHR2 extracellular domain polypeptide, zymosan, and MONTANIDE™. The AMHR2 extracellular domain in combination with zymosan and/or MONTANIDE™ of the present disclosure induce high frequencies of Type-1/Type-17 T cells associated with effective tumor immunity without inducing unresolved granulomas associated with vaccination with CFA, the "gold standard" adjuvant. Thus, vaccination with AMHR2 extracellular domain combined with zymosan and/or MONTANIDE™ provide a unique way to provide safe and effective immunity against growth of human ovarian cancer. In some embodiments, the metabolizable oil comprises a biodegradable oil. For example, the biodegradable oil may be isopropyl myristate, squalene oil, squalane oil, a vegetable oil, or a combination thereof. In some embodiments, the biodegradable oil is a vegetable oil, such as, for example, a vegetable oil selected from the group consisting of almond oil, castor oil, chaulmoogra oil, coconut oil, corn oil, cottonseed oil, olive oil, peanut oil, persic oil, safflower oil, and soya bean oil.

In some embodiments, the metabolizable oil is a pharmaceutical grade oil.

In some embodiments, the composition further comprises a surfactant, for example, mannide monooleate, isomannide monooleate, or a combination thereof. In some embodiments, the surfactant comprises mannide monooleate. For example, the composition may comprise MONTANIDE™, such as MONTANIDE™ ISA 51 VG.

In some embodiments, the composition is an emulsion of water and oil, for example, a water-in-oil emulsion.

In some embodiments, the antigen comprises a polypeptide antigen. In some embodiments, the polypeptide antigen is a retired self-antigen. In some embodiments, the antigen comprises an AMHR2 extracellular domain polypeptide. Carbohydrates In some embodiments, the carbohydrate comprises a polysaccharide, for example, a polysaccharide selected from the group consisting of chitin, dextran, glucan, lentanan, mannan, and combinations thereof.

In some embodiments, the composition comprises a mixture of polysaccharides, for example, a mixture comprising at least three polysaccharides.

In some embodiments, the polysaccharide each polysaccharide in the mixture is selected from the group consisting of chitin, dextran, glucan, lentanan, mannan, and combinations thereof.

In some embodiments, the polysaccharide or mixture of polysaccharides comprises a glucan, e.g., a β-glucan, such as, but not limited to 1-3 β-glucan. In some embodiments, at least 50% of the carbohydrates in the composition are β-glucans.

In some embodiments, the mixture of polysaccharides comprises a mixture of chitins, glucans, and mannans.

In some embodiments, the carbohydrate binds to a pattern recognition receptor, e.g., a TLR2 and/or dectin-1.

For example, in some embodiments, the composition comprises zymosan. Zymosan is a crude cell-wall component mixture of the baker's yeast extracts from *Saccharomyces cerevisiae*, composed mainly of 3-glucans (50-57%), mannans, and chitins. The US Food and Drug Administration (FDA) has given these β-glucans derived from yeast extract a GRAS ("Generally Recognized as Safe") rating. Yeast zymosan serves as a rich source of R (1,3) glucan. Yeast-derived β (1,3) glucan appears to stimulate the immune system, in part, by activating the innate immune system as part of the body's basic defense against fungal infection (Huang et al., (2013) Clin Vaccine Immunol 20:1585-1591). Yeast β (1,3) glucan is a polysaccharide composed primarily of β (1-3)-linked glucose molecules with periodic β (1-3) branches linked via β (1-6) linkages and is more formally known as poly-(1-6)-β-glucopyranosyl-(1-3)-β-D-glucopyranose.

Metabolizable Oils

As used herein, the phrase "metabolizable oil" means an oil that, when introduced into an organism, (1) can be broken down by or eliminated from the organism to a greater extent; (2) can be broken down by or eliminated from the organism more rapidly; and/or (3) results in reduced granuloma formation as compared to Incomplete Freund's Adjuvant. Thus, a "metabolizable oil," as that phrase is used herein, need not be completely metabolizable. "Reduced granuloma formation" may be characterized, for example, by one or more of: fewer granulomas formed, granulomas of reduced severity, and granulomas that resolve more quickly.

In some embodiments, the metabolizable oil comprises mineral oil.

In some embodiments, the metabolizable oil comprises a purified oil, e.g., purified mineral oil (such as, but not limited to DRAKEOL™ 6 VR).

In some embodiments, the metabolizable oil comprises a biodegradable oil. Non-limiting examples of biodegradable oils include isopropyl myristate, squalene oil (e.g., MF59), squalane oil, a vegetable oil, or a combination thereof. In some embodiments, the biodegradable oil is a vegetable oil, such as, for example, almond oil, castor oil, chaulmoogra oil, coconut oil, corn oil, cottonseed oil, olive oil, peanut oil, persic oil, safflower oil, soya bean oil, or a combination thereof.

In some embodiments, the metabolizable oil comprises fish oil.

In certain embodiments, the metabolizable oil is a pharmaceutical grade oil.

Surfactants/Emulsions

In some embodiments, a provided composition comprises one or more surfactants. Non-limiting examples of suitable surfactants include mannide monooleate, isomannide monooleate, and combinations thereof. In some embodiments, the composition comprises mannide monooleate.

In some embodiments, provided compositions comprise MONTANIDE™, e.g., a MONTANIDE™ ISA series adjuvant, that comprises a metabolizable oil.

MONTANIDE™ ISA (ISA=Incomplete Seppic Adjuvant) adjuvants (Seppic SA, Paris, France) are a group of oil/surfactant-based adjuvants in which different surfactants are combined with a non-metabolizable mineral oil, a metabolizable oil, or a mixture of the two. They are typically prepared for use as an emulsion with an aqueous antigen solution. The various MONTANIDE™ ISA group of adjuvants are used as water-in-oil emulsions, oil-in-water emulsions, or water-in-oil-in-water emulsions.

In some embodiments, the composition comprises MONTANIDE™ ISA 51, MONTANIDE™ ISA 51 VG, or any bioequivalent adjuvant derived therefrom (for example, by replacing the oleic acid isolated from olives by that isolated from another source or a synthetic one). MONTANIDE™ ISA 51 is a mixture of a highly purified mineral oil (DRAKEOL™ 6VR) and a surfactant (mannide monooleate). MONTANIDE™ ISA 51 VG is a similar composition in which the oleic acid is obtained from olives rather than from an animal source In some embodiments, provided compositions are emulsions of water and oil, e.g., water-in-oil emulsions. Methods of creating water-in-oil (w/o) emulsions are well known in the art. A water-in-oil emulsion can be obtained by any of a variety of protocols, such as protocols using any of a variety of devices such as high shear mixers, vortex mixers, and syringes with or without connectors (e.g., T- or I-connectors). In some embodiments, provided compositions comprise adjuvant (such as a MONTANIDE™ adjuvant) that creates a depot effect, that is, an adjuvant that causes an antigen in the same composition to be slowly released in the body, thus prolonging the exposure of immune cells to the antigen.

Antigens

Generally, any molecule or portion of a molecule against which an immune response is desired may be used as an antigen. Antigens may comprise any one of, but are not limited to, peptides, polypeptides, proteins, cells (or component thereof), live-attenuated pathogens (or component thereof), and heat-killed pathogens (or component thereof).

In some embodiments, antigens are non-self antigens, that is, they are foreign to the organism to which a composition comprising an antigen is intended to be administered.

In some embodiments, antigens are self-antigens in that they are or were expressed in at least some cells in the organism to which organism to which a composition comprising an antigen is intended to be administered. In some embodiments, antigens are retired self-proteins in that they were once expressed in an organism but no longer expressed at autoimmunogenic levels in non-malignant mature cells.

In some embodiments, antigens are tumor-associated antigens.

In some embodiments, provided compositions or formulations comprise a mixture of different antigens.

Antigens may comprise one or more modifications. For example, one or more modifications that affect processing, cellular uptake, immunogenicity, and/or stability (e.g., within a peptide/MHC complex) of an antigen or fragment thereof may be used.

In some embodiments, antigens comprise polypeptide antigens. Polypeptide antigens may be any of a variety of lengths, and their sequences may or may not correspond to sequences of naturally occurring proteins. For example, in some embodiments, a full-length or nearly full-length protein may be used as a polypeptide antigen. In some embodiments, antigens or antigen mixtures comprise one or more fragments or variants of a protein.

Anti-Müllerian Hormone Receptor 2 Polypeptides

In some embodiments, the antigen comprises an Anti-Müllerian Hormone Receptor 2 extracellular domain (AMHR2-ED) or an immunogenic fragment thereof. In some embodiments, the antigen comprises multiple (e.g., at least 2, 3, 4, 5, 6, 7, 8, 9, or 10) different AMHR2-ED polypeptides or fragments. In some embodiments, provided compositions comprise a nucleic acid encoding an AMHR2-ED polypeptide instead of or in addition to the AMHR2-ED polypeptide.

In adult women, the longest AMHR2 transcript codes for a 573 amino acid protein expressed exclusively in the ovary and including the ovarian-specific 127 amino acid AMHR2-ED ligand binding domain, along with a 26 amino acid transmembrane domain, and a 403 amino acid cytoplasmic kinase domain (AMHR2-CD) both of which show extra-ovarian expression. The term "anti-Müllerian Hormone Receptor 2 polypeptide," "AMHR2 polypeptide," "anti-Müllerian Hormone Receptor 2 extracellular domain poly-peptide," or "AMHR2-ED polypeptide" is intended to include fragments, variants (e.g., allelic variants), and derivatives thereof. Representative human AMHR2 cDNA and human AMHR2 protein sequences are well known in the art and are publicly available from the National Center for Biotechnology Information (NCBI). For example, at least three human AMHR2 isoforms are known. Human AMHR2 isoform 1 (NP_065434.1 and UNIPROT Q16671-1) is encodable by the transcript variant (NM_020547.3). Nucleic acid and polypeptide sequences of AMHR2 orthologs in organisms other than humans are well known and include, for example, chimpanzee AMHR2 (XM_016923338.1 and XP_016778827.1), rhesus monkey AMHR2 (XM_028829519.1 and XP_028685352.1), dog AMHR2 (XM_543632.6 and XP_543632.4), mouse AMHR2 (NM_144547.2 and NP_653130.2), and rat AMHR2 (NM_030998.1 and NP_112260.1). Each of the above mRNA and protein sequences are hereby incorporated by reference.

In some embodiments, provided herein are AMHR2 poly-peptides and/or nucleic acids encoding AMHR2 polypep-tides. AMHR2 polypeptides are polypeptides that include an amino acid sequence that have sufficient sequence identity with the amino acid sequence of AMHR2 or a portion thereof to elicit an AMHR2-specific immune response.

In certain embodiments, the AMHR2 polypeptide has an amino acid sequence that comprises at least 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, or 140 consecutive amino acids of an AMHR2 amino acid sequence set forth SEQ ID NO: 11 or 9. In some embodiments, the consecutive amino acids are identical to an AMHR2 amino acid sequence set forth SEQ ID NO: 11 or 9.

In certain embodiments, the AMHR2 polypeptide has an amino acid sequence that consists essentially of at least 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, or 140 consecutive amino acids of an AMHR2 amino acid sequence set forth SEQ ID NO: 11 or 9. In some embodiments, the consecutive amino acids are identical to an amino acid sequence of an AMHR2 amino acid sequence set forth SEQ ID NO: 11 or 9.

In certain embodiments, the AMHR2 polypeptide has an amino acid sequence that consists of at least 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, or 140 consecutive amino acids of an AMHR2 amino acid sequence. In some embodi-ments, the consecutive amino acids are identical to an AMHR2 amino acid sequence set forth SEQ ID NO: 11 or 9.

In some embodiments, the AMHR2 polypeptide has an amino acid sequence that comprises 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, or 140 consecutive amino acids that are at least 70%, 75%, 80%, 85%, 90%, 91%, 92%, 93%, 94%, 95%, 96%, 97%, 98% or 99% identical to an AMHR2 amino acid sequence set forth SEQ ID NO: 11 or 9. In some embodiments, the consecutive amino acids are identical to an AMHR2 amino acid sequence set forth SEQ ID NO: 11 or 9.

In some embodiments, the AMHR2 polypeptide has an amino acid sequence that comprises at least 8 consecutive amino acids of SEQ ID NO: 11 or 9.

In some embodiments, the AMHR2 polypeptide has an amino acid sequence that consists essentially of 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, or 140 consecutive amino acids that are at least 70%, 75%, 80%, 85%, 90%, 91%, 92%, 93%, 94%, 95%, 96%, 97%, 98% or 99% identical to an AMHR2 amino acid sequence set forth SEQ ID NO: 11 or 9. In some embodiments, the consecutive amino acids are identical to an AMHR2 amino acid sequence set forth SEQ ID NO: 11 or 9.

In some embodiments, the AMHR2 polypeptide has an amino acid sequence that consists of 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, or 140 consecutive amino acids that are at least 70%, 75%, 80%, 85%, 90%, 91%, 92%, 93%, 94%, 95%, 96%, 97%, 98% or 99% identical to an AMHR2 amino acid sequence set forth SEQ ID NO: 11 or 9. In some embodiments, the consecutive amino acids are identical to an AMHR2 amino acid sequence set forth SEQ ID NO: 11 or 9.

As is well known to those skilled in the art, polypeptides having substantial sequence similarities can cause identical or very similar immune reactions in a host organism. Accordingly, in some embodiments, an AMHR2 polypep-tide that is a derivative, equivalent, variant, fragment, or mutant of AMHR2 can also be suitable for use in the methods and compositions provided herein.

In some embodiments, provided AMHR2 polypeptides are functional equivalents in that they have an amino acid sequence that is altered relative to the sequence of AMHR2 polypeptide (for example, by conservative substitution), yet still elicit immune responses. As used herein, the term "conservative substitution" denotes the replacement of an amino acid residue by another, biologically similar residue. It is well known in the art that the amino acids within the same conservative group can typically substitute for one another without substantially affecting the function or immunogenicity of a protein.

In some embodiments, provided herein are nucleic acids, such as DNA molecules, encoding AMHR2 polypeptides described herein. In some embodiments, provided are com-positions comprising an expression vector comprising an open reading frame encoding an AMHR2 polypeptide. In some embodiments, the AMHR2 nucleic acid includes regulatory elements that facilitate expression of the open reading frame. Such elements can include, for example, one or more of a promoter, an initiation codon, a stop codon, and a polyadenylation signal. In addition, one or more enhancers can be included. These elements can be operably linked to a sequence that encodes the AMHR2 polypeptide.

Examples of promoters include, but are not limited to, promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, Cytomegalovirus (CMV) such as the CMV immediate early promoter, Epstein Barr Virus (EBV), Rous Sarcoma Virus (RSV) as well as promoters from human genes such as human actin, human myosin, human hemoglobin, human muscle creatine, and human metallothionein. Examples of suitable polyadenylation signals include, but are not limited to, SV40 polyadenylation signals and LTR polyadenylation signals.

Non-limiting examples of enhancers or enhancers/promoters include, for example, enhancers from human actin, human myosin, human hemoglobin, human muscle creatine, and viral enhancers, such as those from CMV, RSV and EBV.

In some embodiments, provided nucleic acids are incorporated in a carrier or delivery vector. Useful delivery vectors include but are not limited to biodegradable microcapsules, immuno-stimulating complexes (ISCOMs), liposomes, and genetically engineered attenuated live carriers such as viruses or bacteria.

In some embodiments, the vector is a viral vector, non-limiting examples of which include lentiviruses, retroviruses, herpes viruses, adenoviruses, adeno-associated viruses, vaccinia viruses, baculoviruses, Fowl pox viruses, AV-pox viruses, modified vaccinia Ankara (MVA) viruses, and other recombinant viruses. For example, a vaccinia virus vector can be used to infect dendritic cells.

Formulations

In some embodiments, the antigen and the carbohydrate are present in a ratio of from about 10:1 to about 1:10 (w/w), for example, from about 5:1 to about 1:5 (w/w), from about 4:1 to 1:4 (w/w), from about 3:1 to about 1:3 (w/w), or from about 1:2 to about 2:1 (w/w). In some embodiments, the antigen and the carbohydrate are present in a ratio of about 1:1 (w/w).

In some embodiments, provided compositions comprise an antigen, zymosan, and MONTANIDE™. In some such embodiments, the antigen is a polypeptide antigen.

For example, compositions that may be suitable for treatment and/or prevention of breast cancer may comprise an AMHR2 polypeptide, zymosan, and MONTANIDE™ wherein the AMHR2 polypeptide comprises an amino acid sequence that is at least 80%, 85%, 90%, or 95% identical to the amino acid sequence of SEQ ID NO: 11. In some embodiments, the AMHR2 polypeptide comprises an amino acid sequence that is 100% identical to the amino acid sequence of SEQ ID NO: 11.

In some embodiments, provided compositions are formulated as an emulsion of water and oil, e.g., a water-in-oil emulsion.

In some embodiments, provided are formulations comprising a water-in-oil emulsion of an antigen, zymosan, and MONTANIDE™. In some such embodiments, the antigen is a polypeptide antigen.

For example, in some embodiments, the formulation comprises a water-in-oil emulsion of α-lactalbumin polypeptide, zymosan, and MONTANIDE™, wherein the AMHR2 polypeptide and zymosan are present in the formulation at a ratio of between about 1:5 (w/w) and 5:1 (w/w), and wherein the AMHR2 polypeptide comprises an amino acid sequence that is at least 80%, 85%, 90%, or 95% identical to the amino acid sequence of SEQ ID NO: 11. In some such embodiments, the AMHR2 polypeptide comprises an amino acid sequence that is 100% identical to the amino acid sequence of SEQ ID NO: 11.

In some aspects, provided herein are pharmaceutical compositions (e.g., vaccine compositions). For example, in some embodiments, provided compositions further comprise a pharmaceutically acceptable carrier.

In some embodiments, compositions further comprise an antibiotic.

In some embodiments, an additional physiologically acceptable adjuvant is employed. Such a an additional adjuvant may be used or included in any of a number of ways, including, but not limited to, (i) admixed to other components in a pharmaceutical composition as provided herein after reconstitution of antigens (e.g., polypeptide antigens) and optional emulsification with a metabolizable oil as defined above, (ii) part of a reconstituted antigen-containing composition as provided herein, (iii) physically linked to antigen(s) to be reconstituted; and (iv) administered separately to the subject. The additional adjuvant can, for example, slow release of antigen (e.g., the additional adjuvant can be a liposome) and/or it can be an adjuvant that is immunogenic in its own right, thereby functioning synergistically with antigens (i.e., antigens present in a provided composition).

For example, the additional adjuvant can be a known adjuvant or other substance that promotes antigen uptake, recruits immune system cells to the site of administration, and/or facilitates the immune activation of responding lymphoid cells. Examples of suitable additional adjuvants include, but are not limited to, immunomodulatory molecules (e.g., cytokines), oil and water emulsions, aluminum hydroxide, glucan, dextran sulfate, iron oxide, sodium alginate, Bacto-Adjuvant, synthetic polymers such as poly amino acids and co-polymers of amino acids, saponin, paraffin oil, and muramyl dipeptide. In some embodiments, the additional adjuvant is Adjuvant 65, α-GalCer, aluminum phosphate, aluminum hydroxide, calcium phosphate, β-Glucan Peptide, CpG DNA, GM-CSF, GPI-0100, IFA, IFN-γ, IL-17, lipid A, lipopolysaccharide, Lipovant, MONTA-NIDE™, N-acetyl-muramyl-L-alanyl-D-isoglutamine, Pam3CSK4, quil A, trehalose dimycolate, or zymosan. In some embodiments, the additional adjuvant induces a mixed type 1/type 17 immune response.

In some embodiments, the additional adjuvant is an immunomodulatory molecule that enhances immune responses. For example, the immunomodulatory molecule can be a cytokine, chemokine, or immunostimulatory agent, recombinant versions of any of the foregoing, or nucleic acids encoding any of the foregoing.

Examples of immunomodulatory cytokines include, but are not limited to, interferons (e.g., IFNα, IFNβ and IFNγ), interleukins (e.g., IL-1, IL-2, IL-3, IL-4, IL-5, IL-6, IL-7, IL-8, IL-9, IL-10, IL-12, IL-17 and IL-20), tumor necrosis factors (e.g., TNFα and TNFβ), erythropoietin (EPO), FLT-3 ligand, gIp10, TCA-3, MCP-1, MIF, MIP-1α, MIP-1β, Rantes, macrophage colony stimulating factor (M-CSF), granulocyte colony stimulating factor (G-CSF), and granulocyte-macrophage colony stimulating factor (GM-CSF), as well as functional fragments of any of the foregoing.

In some embodiments, provided compositions comprise an immunomodulatory chemokine that binds to a chemokine receptor, e.g., a CXC, CC, C, or CX3C chemokine receptor.

Examples of chemokines include, but are not limited to, Mip1α, Mip-1β, Mip-3α (Larc), Mip-3β, Rantes, Hcc-1, Mpif-1, Mpif-2, Mcp-1, Mcp-2, Mcp-3, Mcp-4, Mcp-5, Eotaxin, Tarc, Elc, 1309, IL-8, Gcp-2 Gro-α, Gro-β, Gro-γ, Nap-2, Ena-78, Gcp-2, Ip-10, Mig, I-Tac, Sdf-1, and Bca-1 (Blc), as well as functional fragments of any of the foregoing.

Nucleic Acids

In some embodiments, the composition comprises a nucleic acid (e.g., a DNA or RNA molecule) encoding an AMHR2 polypeptide antigen or anti-AMHR2 antibody described herein. In such embodiments, the composition can comprise the nucleic acid instead of or in addition to an antigen and/or antibody. In some embodiments the composition comprises an expression vector comprising an open reading frame encoding a polypeptide, e.g., an AMHR2 polypeptide and/or antibody.

When taken up by a cell (e.g., muscle cell, an antigen-presenting cell (APC) such as a dendritic cell, macrophage, etc.), a DNA molecule can be present in the cell as an extrachromosomal molecule and/or can integrate into the chromosome. DNA can be introduced into cells in the form of a plasmid which can remain as separate genetic material. Alternatively, linear DNAs that can integrate into the chromosome can be introduced into the cell. Optionally, when introducing DNA into a cell, reagents which promote DNA integration into chromosomes can be added.

IV. Methods

Methods of Killing, Depleting, or Disabling AMHR2-Expressing Cells

In one aspect, provided herein are methods of contacting AMHR2-expressing cancer cells with an anti-Anti-Müllerian Hormone Receptor 2 (AMHR2) antibody, such as a humanized, human, or chimeric antibody, which results in the killing, disabling, or depletion of the AMHR2-expressing cancer cells.

In some embodiments, the present application provides methods of disabling AMHR2-expressing cancer cells, comprising contacting the AMHR2-expressing cancer cells with a AMHR2 antibody, thereby killing the AMHR2-expressing cancer cells. Disabling refers to rendering a cell partially or completely non-functional. In some embodiments, the disabling of the AMHR2-expressing cancer cells leads to inducing growth arrest in the cancer cells. In some embodiments, the disabling of the AMHR2-expressing cancer cells leads to apoptosis in the cancer cells. In some embodiments, the disabling of the AMHR2-expressing cancer leads to lysis of the cells, as for example by complement dependent cytotoxicity (CDC) or antibody-dependent cell cytotoxicity (ADCC). In some embodiments, the disabling of the AMHR2-expressing cancer cells leads to necrosis in the cells. In some embodiments, the disabling of the AMHR2-expressing cancer cells leads to inducing growth arrest in the cells. In some embodiments, the disabling of the AMHR2-expressing cancer cells leads to inactivating the cells. In some embodiments, the disabling of the AMHR2-expressing cancer cells leads to neutralizing the activity of a AMHR2 protein in the cells. In some embodiments, the disabling of the AMHR2-expressing cancer cells leads to reduction in proliferation of the cells. In some embodiments, the disabling of the AMHR2-expressing cancer cells leads to an altered temporal expression of the cells within tumor tissue or tumor microenvironment (TME). In some embodiments, the method further comprises removing the AMHR2-expressing cancer cells.

In any and all aspects of disabling AMHR2-expressing cancer cells as described herein, any increase or decrease or alteration of an aspect of characteristic(s) or function(s) is as compared to a cell not contacted with an anti-AMHR2 antibody.

In some embodiments, the present application provides methods of killing (also referred to as inducing cell death) AMHR2-expressing cancer cells, comprising contacting the AMHR2-expressing cancer cells with an anti-TREM2 antibody, thereby killing the AMHR2-expressing cancer cells. In some embodiments the killing is increased relative to AMHR2-expressing cancer cells that have not been contacted with an anti-TREM2 antibody. In some embodiments, the contacting induces programmed cell death in the AMHR2-expressing cancer cells. In some embodiments, the contacting induces apoptosis in the AMHR2-expressing cancer cells. In some embodiments, the programmed cell death is mediated by caspase-3. In some embodiments, the apoptosis is mediated by caspase-3. In some embodiments, 10%-100% of the AMHR2-expressing cancer cells are killed. In some embodiments, at least 10%, 20%, 30%, 40%, 50%, 60%, 70%, 80%, 90, or 100% of the AMHR2-expressing cancer cells are killed.

Methods of Treating Cancer

In another aspect, provided herein are methods of treating cancer by administering an anti-Anti-Müllerian Hormone Receptor 2 (AMHR2) antibody.

In some embodiments, the AMHR2-expressing cancer cells are reduced in number. In some embodiments, the AMHR2-expressing cancer cells are killed, for example by necrosis, or apoptosis. In some embodiments, the AMHR2-expressing cancer cells are induced to undergo growth arrest. In some embodiments the AMHR2-expressing cancer cells no longer proliferate.

In some embodiments, the contacting is in vitro. In some embodiments, the contacting is in vivo. In some particular embodiments, the contacting is in vivo in a human. In some embodiments, the contacting is effected by administering an anti-AMHR2 antibody. In some embodiments, the individual receiving the antibody (such as a human) has cancer.

In another aspect, the invention provides methods of treating an immune-related condition (e.g., cancer) in an individual comprising administering to the individual an effective amount of a composition comprising an anti-AMHR2 antibody. In another aspect, the invention provides methods of enhancing an immune response in an individual comprising administering to the individual an effective amount of a composition comprising an anti-AMHR2 antibody. An immune response can be an adaptive immune response or an innate immune response. Exemplary immune responses include humoral immune responses (e.g. production of antigen-specific antibodies (neutralizing or otherwise)) and cell-mediated immune responses (e.g. lymphocyte proliferation). Type-1 proinflammatory immune responses are characterized by the production of IFNγ. Type-2 regulatory immune responses are characterized by expression of IL-4 or IL-5. Type-17 proinflammatory immune responses are characterized by expression of IL-17. In some instances, a mixed immune response can be generated. For example, in some instances a mixed Type-1/Type-17 inflammatory immune response is generated that is characterized by the expression of both IFNγ and IL-17.

In some embodiments, the methods provided herein (such as methods of effecting the disabling of AMHR2-expressing cells) are useful for the treatment of cancer and as such an individual receiving an anti-AMHR2 antibody or an anti-AMHR2 antibody has cancer.

Any suitable cancer may be treated with the antibodies provided herein. Examples of cancers include solid tumors, soft tissue tumors, hematopoietic tumors and metastatic lesions. Examples of hematopoietic tumors include, leukemia, acute leukemia, acute lymphoblastic leukemia (ALL), B-cell, T-cell or FAB ALL, acute myeloid leukemia (AML), chronic myelocytic leukemia (CML), chronic lymphocytic leukemia (CLL), e.g., transformed CLL, diffuse large B-cell lymphomas (DLBCL), follicular lymphoma, hairy cell leukemia, myelodyplastic syndrome (MDS), a lymphoma, Hodgkin's disease, a malignant lymphoma, non-Hodgkin's lymphoma, Burkitt's lymphoma, multiple myeloma, or Richter's Syndrome (Richter's Transformation). Examples of solid tumors include malignancies, e.g., sarcomas, adenocarcinomas, and carcinomas, of the various organ systems, such as those affecting head and neck (including pharynx), thyroid, lung (small cell or non-small cell lung carcinoma (NSCLC)), breast, lymphoid, gastrointestinal (e.g., oral, esophageal, stomach, liver, pancreas, small intestine, colon and rectum, anal canal), genitals and genitourinary tract (e.g., renal, urothelial, bladder, ovarian, uterine, cervical, endometrial, prostate, testicular), CNS (e.g., neural or glial cells, e.g., neuroblastoma or glioma), or skin (e.g., melanoma).

In some embodiments, the cancer is an AMHR2-expressing cancer, such as ovarian cancer, known in the medical field. In some embodiments, the cancer is a solid cancer. In some embodiments, the cancer is immunoevasive. In some embodiments, the cancer is immunoresponsive. In some embodiments, the cancer is ovarian cancer.

In some embodiments, the ovarian cancer is stage I, stage IA, stage IB, stage IC, stage II, stage IIA, stage IIB, stage III, stage IIIA1, stage IIIA2, stage IIIB, stage IIIC, stage IV, stage IVA, or stage IVB ovarian cancer. Two systems for determining cancer stages are widely used, the FIGO (International Federation of Gynecology and Obstetrics) system and the AJCC (American Joint Committee on Cancer) TNM staging system. However, the factors and assigned stages of ovarian cancer in both systems are largely the same. Thus, a stage II2B ovarian cancer under FIGO staging is the same as a stage II2B ovarian cancer under AJCC staging. In some embodiments, the cancer is a metastatic ovarian cancer In some embodiments, the cancer is refractory to at least one treatment. In some embodiments, the cancer is refractory to more than one treatment. In some embodiments, the cancer is refractory to at least two treatment, three treatments, or four treatments. Refractory or resistant cancers are cancers that do not respond to treatment. A refractory cancer may be resistant at the beginning of treatment or gain resistance over the course of treatment.

In some embodiments, the antibody treatment enhances an immune response in the subject. In some embodiments, the enhanced immune response is an adaptive immune response. In some embodiments, the enhanced immune response is an innate immune response.

In some embodiments, the antibody induces a durable immune response. A durable immune response is a long lasting immune response. In some embodiments, a durable immune response is an immune response that lasts longer than 6 months. In some embodiments, a durable immune response lasts longer than 12 months. A durable immune response can last longer than 6 months, 8 months, 10 months, 12 months, 14 months, 16 months, 18 months, 20 months, 24 months, 26 months, 28 months, 30 months, 32 months, 34 months, or 36 months or longer.

In some embodiments, the method further comprises determining the expression level of AMHR2 protein in a biological sample from the individual. In some embodiments the biological sample includes, but is not limited to a body fluid, a tissue sample, an organ sample, urine, feces, blood, saliva, CSF and any combination thereof. In some embodiments the biological sample is derived from a tumor tissue. In some embodiments, the expression level comprises the mRNA expression level of mRNA encoding AMHR2 protein. In In some embodiments the expression level of AMHR2 protein is detected in the sample using a method selected from the group consisting of FACS, Western blot, ELISA, immunoprecipitation, immunohistochemistry, immunofluorescence, radioimmunoassay, dot blotting, immunodetection methods, HPLC, surface plasmon resonance, optical spectroscopy, mass spectrometry, HPLC, qPCR, RT-qPCR, multiplex qPCR or RT-qPCR, RNA-seq, microarray analysis, SAGE, MassARRAY technique, and FISH, and combinations thereof.

Combination Therapies

In certain embodiments, methods provided herein further comprise administering, or compositions provided herein further comprise, one or more additional agents such as, but not limited to, anti-cancer agents (e.g., chemotherapeutics), immunotherapeutic, immunomodulatory and/or anti-angiogenic agents.

In some embodiments, compositions comprise an additional anti-cancer agent. In some embodiments, the anti-cancer agent is selected from the group consisting of bevacizumab, bleomycin, carboplatin, cisplatin, cyclophosphamide, docetaxel, doxorubicin, etoposide, gemcitabine, letrozole, olaparib, tamoxifen, topotecan, trabectedin, a CTLA4 antibody, a PD-1 antibody, a PD-L1 antibody, and a TGFβ antibody.

In some embodiments, the additional agent is a naturally occurring or synthetic anti-cancer agent, for example, an anti-cancer agent as described in "Cancer Chemotherapeutic Agents," American Chemical Society, 1995, W. O. Foye Ed.

In some embodiments, the anti-cancer agent comprises a small molecule.

In some embodiments, the anti-cancer agent is a receptor antagonist or blocker. In some embodiments, the chemotherapeutic agent is selected from the group consisting of VEGF receptor antagonists (such as, for example, vatalanib (PTK-787/ZK222584), SU-5416, SU-6668, SU-11248, SU-14813, AZD-6474, AZD-2171, CP-547632, CEP-7055, AG-013736, IM-842 or GW-786034), VEGFtrap, EGFR and/or HER2 antagonists (such as, for example, gefitinib, erlotinib, CI-1033, GW-2016, herceptin, iressa (ZD-1839), tarceva (OSI-774), PKI-166, EKB-569, or HKI-272), integrin receptor antagonists, and protein kinase receptor antagonists (e.g., atrasentan). In some embodiments, the chemotherapeutic agent inhibits expression of HER2.

In some embodiments, the anti-cancer agent comprises an antagonist of a protein kinase, for example, an antagonist of mitogen-activated protein kinase (e.g., BAY-43-9006 or BAY-57-9006) or imatinib.

In some embodiments, the anti-cancer agent comprises a tubulin-binding agent.

In some embodiments, the anti-cancer agent comprises an antibody. For example, chemotherapeutic antibodies include, but are not limited to, antibodies directed against cytokines (e.g., TGFβ), antibodies targeting surface molecules of cancer cells, and antibodies targeting growth factors or their receptors. Non-limiting examples of antibody chemotherapeutics include alemtuzumab, apolizumab, bevacizumab, daclizumab, cetuximab, ibritumomab, mitumomab, matuzumab, oregovomab, rituximab, vitaxin (a vitronectic receptor antibody), DC101 (a VEGFR2 antibody), ID09C3 (an MHC class II monoclonal antibody), and IMC-1C11 (a kinase insert domain receptor antibody).

In some embodiments, the anti-cancer agent comprises a cell cycle inhibitor.

In some embodiments, the anti-cancer agent comprises a cytokine inhibitor.

In some embodiments, the anti-cancer agent comprises a hypoxia-selective cytotoxin.

In some embodiments, the anti-cancer agent comprises a TNFα inhibitor, e.g., etanercept.

In some embodiments, the anti-cancer agent comprises an interferon, e.g., interferon β.

In some embodiments, the anti-cancer agent comprises an interleukin, e.g., IL-10 or IL-12.

In some embodiments, the anti-cancer agent comprises an immunomodulator, e.g., lenalidomide or thalidomide.

In some embodiments, the anti-cancer agent comprises an immune checkpoint inhibitor. In some embodiments, the immune checkpoint inhibitor is an inhibitor of CTLA4, such as a CTLA4 antibody (e.g., ipilimumab (BMS), tremelimumab (AstraZeneca) and/or KAHR-102 (Kahr Medical)). In some embodiments, the immune checkpoint inhibitor is an inhibitor of PD-1, such as a PD-1 antibody (e.g., nivolumab (BMS), pembrolizumab/lambrolizumab (Merck), pidilizumab (Curetech), AMP-224 (GSK), AMP-514 (AstraZeneca), STI-A1110 (Sorrento) and/or TSR-042 (Tesaro)). In some embodiments, the immune checkpoint inhibitor is an inhibitor of PD-L1 and/or PD-L2, such as a PD-L1 and/or a PD-L2 antibody (e.g., RG-7446 (Roche), BMS-936559 (BMS), MEDI-4736 (AstraZeneca), MSB-0020718C (Merck), AUR-012 (Pierre Fabre Med), STI-A1010 (Sorrento)). In some embodiments, the anti-cancer agent comprises a leukotriene antagonist.

In some embodiments, the anti-cancer agent comprises a DNA alkylating agent, such as, for example, a nitrogen mustard or derivative thereof (e.g., bendamustine, chlorambucil, chlormethine (mechlorethamine), oxazaphosphorines (e.g., cyclophosphamide, ifosfamide, and trofosfamide), melphalan, nitromin, uramustine), a nitrosourea (e.g., carmustine, lomustine, or streptozocin), an alkylsulfonate (e.g., busulfan), an ethyleneimine (aziridine) (e.g., thiotepa or hexamethylmelamine), a metal salt (e.g., carboplatin, cisplatin, or oxaliplatin), or a hydrazine (e.g., altretamine, procarbazine, dacarbazine, or temozolomide).

In some embodiments, the anti-cancer agent comprises a platinum compound such as, for example, cisplatin, oxaliplatin, carboplatin, satraplatin, tetraplatin, or iproplatin.

In some embodiments, the anti-cancer agent comprises a DNA intercalator, e.g., an anthracycline such as, for example, daunorubicin, doxorubicin (adriamycin), liposomal doxorubicin (doxil), epirubicin, or idarubicin.

In some embodiments, the anti-cancer agent comprises a DNA minor-groove binding compound.

In some embodiments, the anti-cancer agent comprises a DNA cross-linking agent.

In some embodiments, the anti-cancer agent comprises an antimetabolite such as, for example, a pyrimidine or purine analogue or antagonist, or a nucleoside diphosphate reductase inhibitor. Non-limiting examples of antimetabolites include cytarabine, 5-fluorouracile (5-FU), pemetrexed, tegafur/uracil, uracil mustard, floxuridine, fludarabine, gemcitabine, capecitabine, mercaptopurine, cladribine, thioguanine, methotrexate, pentostatin, or hydroxyurea.

In some embodiments, the anti-cancer agent comprises an inhibitor of DNA transcription, RNA translation, or protein expression. Non-limiting examples of DNA transcription inhibitors include topoisomerase I or II inhibitors (e.g., camptothecin, irinotecan, topotecan, epipodophyllotoxin, etoposide, teniposide, or tricyclic carboxmide-based agents) and inhibitors of transcription factor complexes (such as, for example, inhibitors of the ESX/DRIP130/Sur-2 complex).

In some embodiments, the anti-cancer agent comprises a proteasome inhibitor such as, for example, bortezomib.

In some embodiments, the anti-cancer agent comprises an enzyme, e.g., asparaginase or pegylated asparaginase (pegaspargase).

In some embodiments, the anti-cancer agent comprises an oligonucleotide or polynucleotide.

In some embodiments, the anti-cancer c agent comprises an histone deacetylase inhibitor such as, for example, SAHA, MD-275, trichostatin A, CBHA, LAQ824, or valproic acid.

In some embodiments, the chemotherapeutic agent comprises a chemical radiation sensitizers or protector.

In some embodiments, the anti-cancer agent comprises an inhibitor of an oncogene, e.g., a P53 or Rb inhibitor.

In some embodiments, the anti-cancer agent comprises a plant-derived agent such as a taxane (e.g., paclitaxel or docetaxel), a vinca alkaloid (e.g., navelbine, vinblastin, vincristin, vindesine or vinorelbine), or a tropical alkaloid (e.g., colchicine or a derivative thereof).

In some embodiments, the anti-cancer agent comprises quinazoline or a derivative thereof, such as, for example, afatanib, erlotinib, gefitinib, or lapatinib.

In some embodiments, the anti-cancer agent comprises an antimitotic agent, for example, antimitotic peptides (e.g., phomopsin and dolastatin), antimitotic carbamate derivatives (e.g., combretastatin (A4) or amphetinile).

In some embodiments, the anti-cancer agent comprises a steganacin.

In some embodiments, the anti-cancer agent comprises a hormone blocker, e.g., anti-androgens, anti-estrogens, gonadotropin-releasing hormone (GNrH) antagonists (e.g., abarelix), GNrH analogues, and aromatase inhibitors. Non-limiting examples of such anti-androgens include anandron, bicalutamide, casodex, cyproterone acetate, flutamide, mitotane, and nilutamide. Non-limiting examples of anti-estrogens include droloxifene, raloxifene, tamoxifen, trioxifene, and zindoxifene. Non-limiting examples of GNrH analogues include leuprorelin (leuprolide), buserelin, goserelin and triptorelin. Non-limiting examples of aromatase inhibitors include aminogluthetimide, anastrozole, fadrozole, formestane or letrozole, and testalactone. Additional examples of hormone blockers include finasteride.

In some embodiments, the anti-cancer agent is a hormone or a derivative thereof, e.g., an estrogen (e.g., estramustine (T-66), 17-β-estra-diol (including derivatives ICI 164,384 or ICI 182,780), a gestagen, or a progestin (e.g., megestrol).

In some embodiments, the anti-cancer agent comprises a piperazine derivative, e.g., piprobroman.

In some embodiments, the anti-cancer agent comprises a glutathione analog, e.g., TLK-286.

In some embodiments, the anti-cancer agent comprises a biological response modifier, e.g., aldesleukin or denileukin diftitox.

In some embodiments, the anti-cancer agent comprises a matrix metalloprotease inhibitor, e.g., marimastat, TIMP-1, or TIMP-2.

In some embodiments, the anti-cancer agent comprises a complex of rare earth elements, e.g., lanthanide complexes.

In some embodiments, the anti-cancer agent comprises a metal having anti-cancer effects, e.g., zinc.

In some embodiments, the anti-cancer agent comprises a photo-chemically activated drug, e.g., porfimer, photofrin, a benzoporphyrin derivative, a pheophorbide derivative, merocyanine 540 (MC-540) or tin etioporpurin.

In some embodiments, the anti-cancer agent comprises an agent used in photo-chemotherapeutic therapy, e.g., psoralens, which are used with ultraviolet therapy.

In some embodiments, the anti-cancer agent comprises a nitroaromatic compound, e.g., RSU-1069, RB-6145, or CB-1954. In some embodiments, the chemotherapeutic agent comprises a nitroxyl or N-oxide, e.g., such as SR-4233.

In some embodiments, the anti-cancer agent comprises an anti-sense RNA or DNA, e.g., oblimersen.

In some embodiments, the anti-cancer agent comprises an halogenated pyrimidine analogue, e.g., bromodeoxyuridine or iododeoxyuridine.

In some embodiments, the additional agent comprises an angiogenesis inhibitor such as, for example, DC-101, neovastat, tetrathiomolybdate, a thymidine-phosphorylase inhibitor, or TNP-470.

In some embodiments, the additional agent comprises an antibiotic (including macrolides), antifungal, or antiparasitic agent, which may or may not have an anti-cancer effect. Non-limiting examples of antibiotics that may be used as additional agents include acridine, actinomycin, amsacrine, ansamitocin, anthramycin, bleomycin, chloromycin, dactinomycin, distamycin, duocarmycin, geldanamycin, ketoconazole, liblomycin, maytansine, mithramycin, mitomycin, mitoxantone, netropsin, a nitroimidazole (e.g., benznidazole, metronidazole, misonidazole, nimorazole, NLA-1, NLP-1), a nitroacridine, a nitroquinoline, a nitropyrazoloacridine, olivomycin, phleomycin, a phthalanilide (e.g., propamidine or stilbamidine), pibenzimol, plicamycin, rifamycin, rhizoxin, squalamine, tanespimycin (17-allylaminogeldanamycin), or a derivative or salt of any of the foregoing.

In some embodiments, the additional agent comprises an aziridoquinone (e.g., mitomycin C, BMY-42355, AZQ or EO-9).

In some embodiments, the additional agent comprises a 2-nitroimidazole such as misonidazole, NLP-1 or NLA-1, a nitroacridine, a nitroquinoline, a nitropyrazoloacridine, a In some embodiments, the additional agent comprises an anti-inflammatory agent such as, for example, a steroid or a non-steroidal anti-inflammatory drug. Non-limiting examples of steroids include prednisone, prednisolone, methylprednisolone, dexamethasone, budenoside, fluocortolone or triamcinolone. Non-limiting examples of additional anti-inflammatory agents include acetylsalicyclic acid, mesalazin, ibuprofen, naproxen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen, indomethacin, sulindac, tolmetin, zomepirac, nabumetone, diclofenac, fenclofenac, alclofenac, bromfenac, ibufenac, aceclofenac, acemetacin, fentiazac, clidanac, etodolac, oxpinac, mefenamic acid, meclofenamic acid, flufenamic acid, nifluminic acid, tolfenamic acid, diflunisal, flufenisal, piroxicam, tenoxicam, lomoxicam, nimesulide, meloxicam, celecoxib, and rofecoxib.

In some embodiments, the additional agent comprises a biphosphonate or derivative thereof, such as, for example, minodronic acid or its derivatives (YM-529, Ono-5920, YH-529), zoledronic acid monohydrate, ibandronate sodium hydrate or clodronate disodium.

In some embodiments, the additional agent is in the form of a pharmaceutically acceptable salt, hydrate and/or solvate. In some embodiments, the chemotherapeutic agent is in the form of an individual optical isomer, a mixture of individual enantiomers, or a racemate thereof.

The additional therapeutic agent can be administered by any suitable means. In some embodiments, an antibody provided herein and the additional therapeutic agent are included in the same pharmaceutical composition. In some embodiments, an antibody provided herein and the additional therapeutic agent are included in different pharmaceutical compositions.

In embodiments where an antibody provided herein and the additional therapeutic agent are included in different pharmaceutical compositions, administration of the antibody can occur prior to, simultaneously, and/or following, administration of the additional therapeutic agent. In some embodiments, administration of an antibody provided herein and the additional therapeutic agent occur within about one month of each other. In some embodiments, administration of an antibody provided herein and the additional therapeutic agent occur within about one week of each other. In some embodiments, administration of an antibody provided herein and the additional therapeutic agent occur within about one day of each other. In some embodiments, administration of an antibody provided herein and the additional therapeutic agent occur within about twelve hours of each other. In some embodiments, administration of an antibody provided herein and the additional therapeutic agent occur within about one hour of each other.

Dosages

In some embodiments, for in vivo administration of the anti-AMHR2 antibodies described herein, normal dosage amounts may vary from about 10 ng/kg up to about 100 mg/kg of an individual's body weight or more per day, preferably about 1 mg/kg/day to 10 mg/kg/day, depending upon the route of administration. For repeated administrations over several days or longer, depending on the severity of the disease or disorder to be treated, the treatment is sustained until a desired suppression of symptoms is achieved. An exemplary dosing regimen comprises administering an initial dose of an anti-AMHR2 antibody of about 2 mg/kg, followed by a weekly maintenance dose of about 1 mg/kg every other week. Other dosage regimens may be useful, depending on the pattern of pharmacokinetic decay that the physician wishes to achieve. For example, dosing an individual from one to twenty-one times a week is contemplated herein. In certain embodiments, dosing ranging from about 3 µg/kg to about 2 mg/kg (such as about 3 µg/kg, about 10 µg/kg, about 30 µg/kg, about 100 µg/kg, about 300 µg/kg, about 1 mg/kg, and about 2/mg/kg) may be used. In certain embodiments, dosing frequency is three times per day, twice per day, once per day, once every other day, once weekly, once every two weeks, once every four weeks, once every five weeks, once every six weeks, once every seven weeks, once every eight weeks, once every nine weeks, once every ten weeks, or once monthly, once every two months, once every three months, or longer. Progress of the therapy is easily monitored by conventional techniques and assays. The dosing regimen, including the anti-AMHR2 antibody administered, can vary over time independently of the dose used.

In certain embodiments, the therapeutically effective amount comprises more than one dose, e.g., at least two doses or at least three doses. In some embodiments, the therapeutically effective amount comprises no more than three doses, e.g., exactly three doses. In some embodiments, each dose is administered one or more weeks apart, e.g., at least two or more weeks apart, at least three or more weeks apart, or at least four weeks apart. In some embodiments, each dose is administered about four weeks apart.

In some embodiments, each dose contains approximately the same amount of antigen. In some embodiments, each dose contains approximately the same amount of antigen and the same amount of carbohydrate.

In some embodiments, an initial dose is administered, and the subject is monitored for an immunological and/or clinical response. Suitable means of immunological monitoring include using patient's peripheral blood mononuclear cells (PBMC) as responders and neoplastic cells or the antigen as stimulators for determining memory or recall responses. An immunological reaction also can be determined by presence of a delayed inflammatory response at the site of administration. One or more doses subsequent to the initial dose can be given as appropriate, for example, on a monthly, semi-monthly, or weekly basis, until the desired effect is achieved. Thereafter, additional booster or maintenance doses can be given as required, particularly when immunological or clinical benefits appear to subside.

An appropriate dosage may be determined, e.g., by reference to resulting plasma concentrations in subjects who are administered the dose. For example, the maximum plasma concentration (Cmax) and the area under the plasma concentration-time curve from time 0 to infinity (AUC (0-4)) may be used. Dosages include those that produce certain desired values for Cmax and AUC (0-4).

Dosages may depend upon a variety of factors such as, for example, activity of the particular antigen or composition; route of administration; time of administration; rate of excretion or metabolism of components in a particular composition being employed; duration of treatment; other drugs, compounds and/or materials used in combination with the particular antigen composition; the age, sex, weight, condition, general health and prior medical history of the subject; and like factors well known in the medical arts.

In general, a "therapeutically effective amount" of a composition described herein will be that amount which is the lowest amount effective to produce a desired immuno-logic, prophylactic, or therapeutic effect. For example, in some embodiments, a therapeutically effective amount is an amount that is able to induce an effective humoral or cellular T cell response in the subject to be treated, or in some embodiments, an effective systemic immune response. Such an effective amount will generally depend upon certain factors such as those described above.

In some embodiments, each dose contains between about 1 μg to about 20 mg, e.g., between about 1 μg to about 5 mg, between about 50 μg to about 2 mg of antigen, or between about 100 μg to about 1 mg of antigen. For example, in some embodiments, each dose contains about 1 μg, about 2 μg, about 3 μg, about 4 μg, about 5 μg, about 10 μg, about 15 μg, about 20 μg, about 30 μg, about 40 μg, about 50 μg, about 60 μg, about 70 μg, about 80 μg, about 90 μg, about 100 μg, about 150 μg, about 200 μg, about 250 μg, about 300 μg, about 350 μg, about 400 μg, about 450 μg, about 500 μg, about 550 μg, about 600 μg, about 650 μg, about 700 μg, about 750 μg, about 800 μg, about 850 μg, about 900 μg, about 950 μg, about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, about 10 mg, about 15 mg, about 20 mg, or any value in between of antigen.

In some embodiments, each dose contains between about 1 μg to about 20 mg, e.g., between about 10 μg to about 10 mg, from about 50 μg to about 5 mg, from about 100 μg to about 2 mg, or from about 100 μg to about 1 mg of carbohydrate. For example, in some embodiments, each dose contains about 1 μg, about 2 μg, about 3 μg, about 4 μg, about 5 μg, about 10 μg, about 15 μg, about 20 μg, about 30 μg, about 40 μg, about 50 μg, about 60 μg, about 70 μg, about 80 μg, about 90 μg, about 100 μg, about 150 μg, about 200 μg, about 250 μg, about 300 μg, about 350 μg, about 400 μg, about 450 μg, about 500 μg, about 550 μg, about 600 μg, about 650 μg, about 700 μg, about 750 μg, about 800 μg, about 850 μg, about 900 μg, about 950 μg, about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, about 10 mg, about 15 mg or about 20 mg or any value in between of carbo-hydrate.

In some embodiments, an antibody is administered intra-venously, intramuscularly, subcutaneously, topically, orally, transdermally, intraperitoneally, intraorbitally, by implanta-tion, by inhalation, intrathecally, intraventricularly, or intra-nasally. An effective amount of an anti-TREM2 antibody may be administered for the treatment of cancer. The appro-priate dosage of the anti-TREM2 antibody may be deter-mined based on the type of cancer to be treated, the type of the anti-TREM2 antibody, the severity and course of the cancer, the clinical condition of the individual, the individu-al's clinical history and response to the treatment, and the discretion of the attending physician.

Compositions (including pharmaceutical compositions) disclosed herein may be administered by any suitable route of administration, including orally, parenterally, and other routes of administration discussed in the "Pharmaceutical Compositions" section. In some embodiments, a therapeu-tically effective amount of the composition is administered by a systemic route of administration (e.g., via oral or parenteral administration). In some embodiments, a thera-peutically effective amount of the composition is adminis-tered locally. In some embodiments, a therapeutically effec-tive amount of the composition is administered by subcutaneous, intradermal, subdermal, or intramuscular injection.

Subjects

The methods described herein can be used to treat any subject in need thereof.

Generally, subjects to which presently disclosed compo-sitions or formulations are administered have an adaptive immune system. In some embodiments, subjects are mam-mals. Examples of subjects include, without limitation, humans, livestock, dogs, cats, mice, rats, and transgenic species thereof. In some embodiments, subjects are humans.

In some embodiments, the subject has cancer or is at risk of developing cancer. For example, the subject may have been diagnosed with cancer. The cancer may be a primary cancer or a metastatic cancer. Subjects may have any stage of cancer, e.g., stage I, stage II, stage III, or stage IV with or without lymph node involvement and with or without metas-tases. Provided compositions may prevent or reduce further growth of the cancer and/or otherwise ameliorate the cancer (e.g., prevent or reduce metastases).

In some embodiments, the subject does not have cancer but has been determined to be at risk of developing cancer, e.g., because of the presence of one or more risk factors such as environmental exposure, presence of one or more genetic mutations or variants, family history, etc.

In some embodiments, the subject has not been diagnosed with cancer. For example, provided compositions and formulations may be used as a preventative vaccine, e.g., in individuals identified as a being at risk, in one or more subpopulations in which prevention may be particularly effective, etc. For example, in the context of vaccines against breast cancer, the subject may be, e.g., a non-lactating female.

In some embodiments, the cancer is ovarian cancer (e.g., a primary ovarian cancer, a metastatic ovarian cancer). In some embodiments the breast cancer is positive for or comprises cells that are positive for AMHR2.

In some embodiments, the subject has undergone surgery to remove at least part of a ovarian tumor. In some embodiments, the subject is genetically predisposed to developing ovarian cancer due to having mutations associated with such risk, e.g., mutations in the BRCA1 or BRCA2 gene. In some embodiments, the subject has a family history of ovarian cancer.

In some embodiments, the cancer expresses or overexpresses a polypeptide that is used as an antigen, or a polypeptide whose fragment(s) and/or variants(s) are used as an antigen, in a provided composition or formulation. For example, in some embodiments, the cancer (e.g., a breast cancer) expresses or overexpresses AMHR2.

In some embodiments, the subject has been administered, will be administered, or is simultaneously administered an additional therapy. The additional therapy may comprise, e.g., surgical resection, radiotherapy, chemotherapy, and/or other modes of immunotherapy. In some embodiments, the additional therapy comprises an additional agent as described herein.

For example, in some embodiments, the subject has been administered, will be administered, or is simultaneously administered an anti-cancer therapy comprising an anti-cancer agent as described herein.

In some embodiments, administration is timed relative to the additional therapy in a manner so as to avoid interfering with the immunogenicity of a composition as described herein.

In some embodiments, the subject has been administered an additional therapy, and, as a result of the additional therapy, the subject presents no clinical symptoms of the disease for which the subject is being treated, e.g., no clinically measurable tumor. However, in some embodiments, the subject is determined to be at risk for recurrence or progression of the disease. For example, when the disease is cancer, the subject may, in some embodiments, be determined to be at risk for recurrence or progression of cancer, e.g., near the original tumor site and/or at metastatic sites. Such subjects can be further categorized as high-risk and low-risk subjects. Categorization can be made on the basis of, e.g., features observed before and/or after treatment with the additional therapy. These features are known in the clinical arts and may be defined for each type of cancer. Features typical of high-risk subgroups include invasion of neighboring tissues, and/or involvement of lymph nodes. Thus, for example, a pharmaceutical composition described herein can be administered to the subject to elicit an anti-cancer response to prevent recurrence or progression of cancer.

Responses

In some embodiments, administering the composition induces an immune response.

Generally, the immune response can include a humoral immune response, a cell-mediated immune response, or both.

A humoral response can be determined, for example, by a standard immunoassay for antibody levels in a serum sample from the subject receiving the pharmaceutical composition.

A cellular immune response is a response that typically involves T cells and can be determined in vitro or in vivo. For example, a general cellular immune response can be determined as the T cell proliferative activity in cells (e.g., peripheral blood leukocytes (PBLs)) sampled from the subject at a suitable time following the administering of a pharmaceutically acceptable composition. For example, after incubation of PBMCs with a stimulator for an appropriate period, [3H]thymidine incorporation can be determined. The percentage of proliferating T cells can be determined using flow cytometry. Another way to measure cellular immunity involves measuring circulating frequencies of T cells secreting proinflammatory Type-1 and/or Type-17 cytokines in response to the antigen.

In some embodiments, the immune response comprises an antigen-specific T cell immune response, which can comprise, for example, CD4+ T cells, CD8+ T cells, or both. In some embodiments, the T cell immune response comprises a type-1 or a type-17 proinflammatory T cell response. In some embodiments, the T cell immune response comprises both a type-1 and a type-17 proinflammatory T cell response.

When the antigen is expressed on a cell, administering the composition may elicit an immune response to that cell. For example, when the antigen is a tumor associated antigen, administering the composition may elicit an immune response to tumor cells that express the antigen.

In some embodiments, administering causes reduced granuloma formation in the subject relative to a reference level. For example, the reference level may be the level of granuloma formation observed in a subject administered a composition comprising Complete Freund's Adjuvant. In some embodiments, the reference level is the level of granuloma formation observed in a subject administered a composition comprising Incomplete Freund's Adjuvant. "Reduced granuloma formation" may be characterized, for example, by one or more of: fewer granulomas formed, granulomas of reduced severity, granulomas whose severity decreases more rapidly, and granulomas that resolve (partially or completely) more quickly.

Cell Therapy

In some embodiments, provided are methods comprising administering to a subject cells (e.g., antigen-presenting cells or precursors thereof) that have been contacted in vitro with a composition as disclosed herein, or cells that have been generated from such cells, such as antigen-primed antigen-presenting cells or antigen-specific lymphocytes.

Methods of Preparation

Antibodies described herein can be produced using recombinant methods and compositions, e.g., as described in U.S. Pat. No. 4,816,567.

In one embodiment, isolated nucleic acid encoding an antibody described herein is provided. Such nucleic acid may encode an amino acid sequence comprising the VL and/or an amino acid sequence comprising the VH of the antibody (e.g., the light and/or heavy chains of the antibody) or an amino acid sequence comprising the VHH of a single domain antibody. In a further embodiment, one or more vectors (e.g., expression vectors) comprising such nucleic acid are provided. In one embodiment, the nucleic acid is provided in a multicistronic vector. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antigen-binding polypeptide construct, or (2) a first vector comprising a nucleic acid that encodes an amino acid sequence comprising the VL of the antigen-binding poly- peptide construct and a second vector comprising a nucleic acid that encodes an amino acid sequence comprising the VH of the antigen-binding polypeptide construct. In one embodiment, the host cell is eukaryotic, e.g. a Chinese Hamster Ovary (CHO) cell, or human embryonic kidney (HEK) cell, or lymphoid cell (e.g., Y0, NS0, Sp20 cell). In one embodiment, a method of making an antibody is pro- vided, wherein the method comprises culturing a host cell comprising nucleic acid encoding the antibody, as provided above, under conditions suitable for expression of the anti- body, and optionally recovering the antibody from the host cell (or host cell culture medium).

For recombinant production of the antibody, nucleic acid encoding an antibody, e.g., as described above, is isolated and inserted into one or more vectors for further cloning and/or expression in a host cell. Such nucleic acid may be readily isolated and sequenced using conventional proce- dures (e.g., by using oligonucleotide probes that are capable of binding specifically to genes encoding the heavy and light chains of the antibody).

The term "substantially purified" refers to a construct described herein, or variant thereof that may be substantially or essentially free of components that normally accompany or interact with the protein as found in its naturally occurring environment, i.e. a native cell, or host cell in the case of recombinantly produced antibody that in certain embodi- ments, is substantially free of cellular material includes preparations of protein having less than about 30%, less than about 25%, less than about 20%, less than about 15%, less than about 10%, less than about 5%, less than about 4%, less than about 3%, less than about 2%, or less than about 1% (by dry weight) of contaminating protein. When the antibody or variant thereof is recombinantly produced by the host cells, the protein in certain embodiments is present at about 30%, about 25%, about 20%, about 15%, about 10%, about 5%, about 4%, about 3%, about 2%, or about 1% or less of the dry weight of the cells. When the antibody or variant thereof is recombinantly produced by the host cells, the protein, in certain embodiments, is present in the culture medium at about 5 g/L, about 4 g/L, about 3 g/L, about 2 g/L, about 1 g/L, about 750 mg/L, about 500 mg/L, about 250 mg/L, about 100 mg/L, about 50 mg/L, about 10 mg/L, or about 1 mg/L or less of the dry weight of the cells. In certain embodiments, "substantially purified" antibody produced by the methods described herein, has a purity level of at least about 30%, at least about 35%, at least about 40%, at least about 45%, at least about 50%, at least about 55%, at least about 60%, at least about 65%, at least about 70%, specifi- cally, a purity level of at least about 75%, 80%, 85%, and more specifically, a purity level of at least about 90%, a purity level of at least about 95%, a purity level of at least about 99% or greater as determined by appropriate methods such as SDS/PAGE analysis, RP-HPLC, SEC, and capillary electrophoresis.

Suitable host cells for cloning or expression of antibody- encoding vectors include prokaryotic or eukaryotic cells described herein.

A "recombinant host cell" or "host cell" refers to a cell that includes an exogenous polynucleotide, regardless of the method used for insertion, for example, direct uptake, trans- duction, f-mating, or other methods known in the art to create recombinant host cells. The exogenous polynucleotide may be maintained as a nonintegrated vector, for example, a plasmid, or alternatively, may be integrated into the host genome. Host cells can include CHO, derivatives of CHO, NS0, Sp20, CV-1, VERO-76, HeLa, HepG2, Per.C6, or BHK.

As used herein, the term "eukaryote" refers to organisms belonging to the phylogenetic domain Eucarya such as animals (including but not limited to, mammals, insects, reptiles, birds, etc.), ciliates, plants (including but not lim- ited to, monocots, dicots, algae, etc.), fungi, yeasts, flagel- lates, microsporidia, protists, etc.

As used herein, the term "prokaryote" refers to prokary- otic organisms. For example, a non-eukaryotic organism can belong to the Eubacteria (including but not limited to, *Escherichia coli, Thermus thermophilus, Bacillus stearo- thermophilus, Pseudomonas fluorescens, Pseudomonas aeruginosa, Pseudomonas putida*, etc.) phylogenetic domain, or the Archaea (including but not limited to, *Metha- nococcus jannaschii, Methanobacterium thermoautotrophi- cum, Halobacterium* such as *Haloferax volcanii* and *Halo- bacterium* species NRC-1, *Archaeoglobus fulgidus, Pyrococcus furiosus, Pyrococcus horikoshii, Aeuropyrum pernix*, etc.) phylogenetic domain.

For example, antibody may be produced in bacteria, in particular when glycosylation and Fc effector function are not needed. For expression of antibody fragments and poly- peptides in bacteria, see, e.g., U.S. Pat. Nos. 5,648,237, 5,789,199, and 5,840,523. (See also Charlton, *Methods in Molecular Biology, Vol.* 248 (B. K. C. Lo, ed., Humana Press, Totowa, N.J., 2003), pp. 245-254, describing expres- sion of antibody fragments in *E. coli.*) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gemgross, *Nat. Biotech.* 22:1409-1414 (2004), and Li et al., *Nat. Biotech.* 24:210-215 (2006).

Suitable host cells for the expression of glycosylated antibodies are also derived from multicellular organisms (invertebrates and vertebrates). Examples of invertebrate cells include plant and insect cells. Numerous baculoviral strains have been identified which may be used in conjunc- tion with insect cells, particularly for transfection of *Spo- doptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CVI line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

In one embodiment, the antibodies described herein are produced in stable mammalian cells, by a method comprising: transfecting at least one stable mammalian cell with: nucleic acid encoding the antibody, in a predetermined ratio; and expressing the nucleic acid in the at least one mammalian cell. In some embodiments, the predetermined ratio of nucleic acid is determined in transient transfection experiments to determine the relative ratio of input nucleic acids that results in the highest percentage of the antibody in the expressed product.

In some embodiments is the method of producing an antibody in stable mammalian cells as described herein wherein the expression product of the at least one stable mammalian cell comprises a larger percentage of the desired antibody as compared to the monomeric heavy or light chain polypeptides, or other antibodies.

In some embodiments is the method of producing a antibody in stable mammalian cells described herein, said method comprising identifying and purifying the desired antibody. In some embodiments, the said identification is by one or both of liquid chromatography and mass spectrometry.

If required, the antibodies can be purified or isolated after expression. Proteins may be isolated or purified in a variety of ways known to those skilled in the art. Standard purification methods include chromatographic techniques, including ion exchange, hydrophobic interaction, affinity, sizing or gel filtration, and reversed-phase, carried out at atmospheric pressure or at high pressure using systems such as FPLC and HPLC. Purification methods also include electrophoretic, immunological, precipitation, dialysis, and chromatofocusing techniques. Ultrafiltration and diafiltration techniques, in conjunction with protein concentration, are also useful. As is well known in the art, a variety of natural proteins bind Fc and antibodies, and these proteins can find use in the present invention for purification of antibodies. For example, the bacterial proteins A and G bind to the Fc region. Likewise, the bacterial protein L binds to the Fab region of some antibodies. Purification can often be enabled by a particular fusion partner. For example, antibodies may be purified using glutathione resin if a GST fusion is employed, $Ni^{+2}$ affinity chromatography if a His-tag is employed or immobilized anti-flag antibody if a flag-tag is used. For general guidance in suitable purification techniques, see, e.g. incorporated entirely by reference Protein Purification: Principles and Practice, $3^{rd}$ Ed., Scopes, Springer-Verlag, NY, 1994, incorporated entirely by reference. The degree of purification necessary will vary depending on the use of the antibodies. In some instances no purification is necessary.

In certain embodiments the antibodies are purified using Anion Exchange Chromatography including, but not limited to, chromatography on Q-sepharose, DEAE sepharose, poros HQ, poros DEAF, Toyopearl Q, Toyopearl QAE, Toyopearl DEAE, Resource/Source Q and DEAE, Fractogel Q and DEAE columns.

In specific embodiments the proteins described herein are purified using Cation Exchange Chromatography including, but not limited to, SP-sepharose, CM sepharose, poros HS, poros CM, Toyopearl SP, Toyopearl CM, Resource/Source S and CM, Fractogel S and CM columns and their equivalents and comparables.

In addition, antibodies described herein can be chemically synthesized using techniques known in the art (e.g., see Creighton, 1983, Proteins: Structures and Molecular Principles, W. H. Freeman & Co., N.Y and Hunkapiller et al., Nature, 310:105-111 (1984)). For example, a polypeptide corresponding to a fragment of a polypeptide can be synthesized by use of a peptide synthesizer. Furthermore, if desired, nonclassical amino acids or chemical amino acid analogs can be introduced as a substitution or addition into the polypeptide sequence. Non-classical amino acids include, but are not limited to, to the D-isomers of the common amino acids, 2,4diaminobutyric acid, alpha-amino isobutyric acid, 4aminobutyric acid, Abu, 2-amino butyric acid, g-Abu, e-Ahx, 6amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, alanine, fluoro-amino acids, designer amino acids such as methyl amino acids, C-methyl amino acids, N-methyl amino acids, and amino acid analogs in general. Furthermore, the amino acid can be D (dextrorotary) or L (levorotary).

V. Pharmaceutical Compositions

Provided herein are pharmaceutical compositions comprising an anti-Anti-Müllerian Hormone Receptor 2 (AMHR2) antibody and a pharmaceutically acceptable carrier or excipient. The present application provides compositions comprising the antibodies including pharmaceutical compositions comprising any one or more of the antibodies described herein with one or more pharmaceutically acceptable excipients. In some embodiments the composition is sterile. The pharmaceutical compositions generally comprise an effective amount of an antibody.

These compositions can comprise, in addition to one or more of the antibodies disclosed herein, a pharmaceutically acceptable excipient, carrier, buffer, stabilizer or other materials well known to those skilled in the art. Such materials should be non-toxic and should not interfere with the efficacy of the active ingredient. The precise nature of the carrier or other material can depend on the route of administration, e.g. oral, intravenous, cutaneous or subcutaneous, nasal, intramuscular, intraperitoneal routes.

Pharmaceutical compositions disclosed herein may be specially formulated for administration in solid or liquid form, including those adapted for the following: (1) oral administration, for example, drenches (aqueous or non-aqueous solutions or suspensions), tablets (e.g., those targeted for buccal, sublingual, or systemic absorption), boluses, powders, granules, or pastes (e.g., for application to the tongue); or (2) parenteral administration, for example, by subcutaneous, intramuscular, intravenous, or epidural injection. Non-limiting examples of formulations suitable for parenteral administration include sterile solutions, sterile suspensions, and sustained-release formulations.

Pharmaceutical compositions for oral administration can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

Pharmaceutical compositions suitable for parenteral administration may be provided as pharmaceutically acceptable sterile isotonic aqueous or nonaqueous solutions, dispersions, suspensions or emulsions. Alternatively or additionally, pharmaceutical compositions for parenteral administration may be provided as sterile powders, which may be reconstituted into sterile injectable solutions or dispersions just prior to use. Such injectable solutions may contain one or more agents that render the formulation isotonic with the blood of the intended recipient, one or more suspending agents, and/or one or more thickening agents. For example, injectable solutions may comprise one or more of sugars, alcohols, antioxidants, buffers, bacteriostats, and solutes.

Examples of suitable aqueous and nonaqueous pharmaceutically acceptable carriers include, but are not limited to, water, ethanol, polyols (such as glycerol, propylene glycol, polyethylene glycol, and the like), and suitable mixtures thereof; vegetable oils, such as olive oil; and injectable organic esters, such as ethyl oleate. Proper fluidity can be maintained, for example, by the use of coating materials (such as lecithin), by the maintenance of the required particle size in the case of dispersions, and by the use of surfactants.

Pharmaceutical compositions disclosed herein may be formulated as emulsions. For examples, provided are vaccine compositions formulated as emulsions, which provide an alternative to aluminum-based vaccines. Emulsion formulations may be prepared by emulsifying antigens dissolved in an aqueous buffer with an oil, such as any metabolizable oil, as further described herein. Emulsion formulations may form a short-lived depot to facilitate vaccine phagocytosis by innate immune cells, which results in an immune response (Leenaars, Koedam et al. 1998). The oils used in such emulsions can impart unique immune stimulation and result in stronger immune responses than can vaccines comprising alum adjuvants (De Gregorio, Caproni et al. 2013).

In some embodiments, the present disclosure provides a pharmaceutical composition comprising an emulsion, e.g., a water-in-oil emulsion, comprising an antigen and a metabolizable oil, as described herein. For example, in some embodiments, the present disclosure provides a pharmaceutical composition comprising α-lactalbumin polypeptides, zymosan, and a metabolizable oil.

In certain embodiments, the present disclosure provides a pharmaceutical composition comprising about 40-60% v/v of aqueous phase antigen emulsified with about 40-60% v/v of a metabolizable oil (optionally in which a carbohydrate, as described further herein, is mixed). For example, the pharmaceutical composition may comprise about 0.1-25 mg/mL (e.g., 0.5-5 mg/mL) antigen in about 50% v/v of a metabolizable oil/carbohydrate composition.

In some embodiments, an emulsion of the pharmaceutical composition disclosed herein is formed by mixing aqueous phase antigen with a metabolizable oil at a ratio of from about 1.5:1 to about 1:1.5, such as about 1.5:1, about 1.4:1, about 1.3:1, about 1.2:1, about 1.1:1, about 1:1, about 1:1.1, about 1:1.2, about 1:1.3, about 1:1.4, or about 1:1.5, or any value in between. In some embodiments, a carbohydrate is suspended in the metabolizable oil before forming emulsions. In some embodiments, zymosan is suspended in the metabolizable oil before forming emulsions.

Pharmaceutical compositions disclosed herein may be formulated into pharmaceutically acceptable dosage forms by conventional methods known to those of skill in the art.

Metabolizable oils and/or the carbohydrates in provided pharmaceutical compositions may, in some embodiments, act as an adjuvant that increases the immunogenicity of the pharmaceutical composition.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives can be included, as required.

A composition can be administered alone or in combination with other treatments, either simultaneously or sequentially dependent upon the condition to be treated.

Methods of preparing these formulations or compositions may include a step of bringing into association an antigen with the carbohydrate, metabolizable oil, pharmaceutically acceptable carrier, and, optionally, one or more accessory ingredients. In general, formulations may be prepared by uniformly and intimately bringing into association one or more composition components described herein with liquid pharmaceutically acceptable carriers, finely divided solid pharmaceutically acceptable carriers, or both, and then, if necessary, shaping the product.

Whether it is a polypeptide, antibody (e.g., anti-AMHR2 antibody), nucleic acid, small molecule or other pharmaceutically useful compound that is to be given to an individual, administration is preferably in a "therapeutically effective amount" or "prophylactically effective amount" (as the case can be, although prophylaxis can be considered therapy), this being sufficient to show benefit to the individual. The actual amount administered, and rate and time-course of administration, will depend on the nature and severity of protein aggregation disease being treated. Prescription of treatment, e.g. decisions on dosage etc., is within the responsibility of general practitioners and other medical doctors, and typically takes account of the disorder to be treated, the condition of the individual subject, the site of delivery, the method of administration and other factors known to practitioners. Examples of the techniques and protocols mentioned above can be found in Remington's Pharmaceutical Sciences, 16th edition, Osol, A. (ed), 1980.

VI. Kits and Articles of Manufacture

The present application provides kits comprising any one or more of the antibody and/or vaccine compositions described herein. In some embodiments, the kits further contain a component selected from any of secondary antibodies, reagents for immunohistochemistry analysis, pharmaceutically acceptable excipient and instruction manual and any combination thereof. In one specific embodiment, the kit comprises a pharmaceutical composition comprising any one or more of the antibody compositions described herein, with one or more pharmaceutically acceptable excipients.

The present application also provides articles of manufacture comprising any one of the antibody compositions or kits described herein. Examples of an article of manufacture include vials (including sealed vials).

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

Example 1: Generation of Human AMHR2-ED Antibody

Materials and Methods
Generation of Recombinant Human AMHR2-ED

Figure 2:
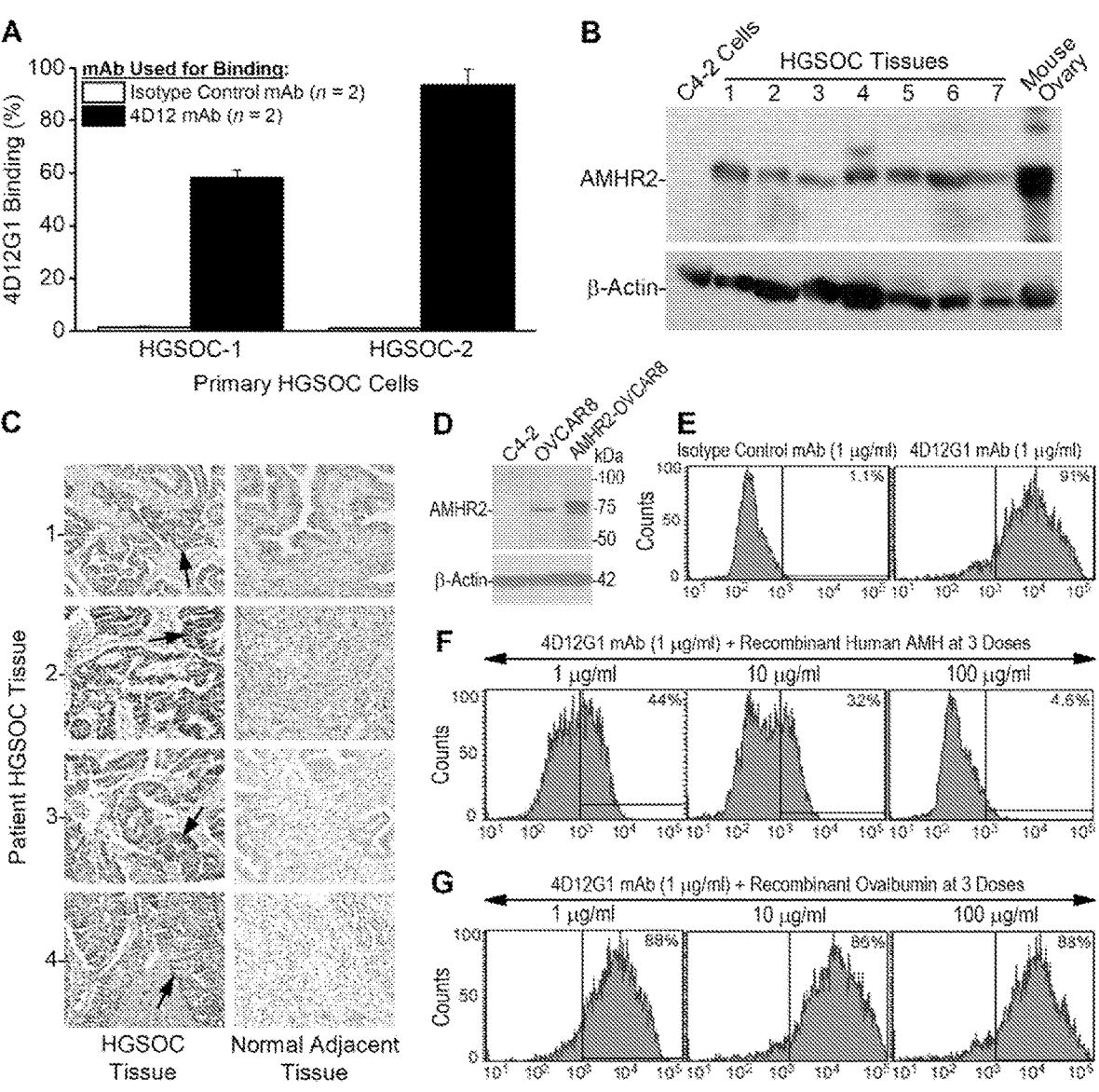
FIG. 2 shows that the 4D12G1 mAb recognizes AMHR2-ED in human EOC and competes with AMH for binding to AMHR2-ED. (A) Flow cytometry analysis showing that the 4D12G1 mAb binds to the majority of cells generated from two primary HGSOC tissues examined. Error bars indicate ±SD. (B) The 4D12G1 mAb was used in Western blots of seven different HGSOC tissue lysates (25 μg protein/lane) with a positive control lysate generated from a young C57BL/6 ovary and a negative control lysate generated from C4-2 human prostate cancer cells. Immunostaining with a 0-actin antibody was used to confirm normalized lysate loading. The Western blots shown are representative of three experiments that provided similar results. (C) The 4D12G1 mAb was used in immunohistochemical staining (20×) of tissue sections from four HGSOC patients (left column) and their normal adjacent fallopian tube tissues (right column). Arrows indicate staining of the tumor parenchyma. The stromal areas of the EOC tumors were not immunostained nor were all areas of the normal adjacent fallopian tube tissues. All experiments were performed three times yielding similar results. (D) Western blot analysis of lysates from OVCAR8 cells and AMHR2-OVCAR8 cells with lysates from C4-2 prostate cancer cells used as controls and immunostaining with a 0-actin antibody was used to confirm normalized lysate loading. Flow cytometry analysis showed that: (E) the 4D12G1 mAb binds to 91% of AMHR2-OVCAR8 cells; (F) the AMH cognate ligand for AMHR2-ED effectively competes in a dose-dependent manner with the 4D12G1 mAb for binding to AMHR2-OVCAR8 cells; and (G) recombinant ovalbumin failed to compete with the 4D12G1 mAb for binding to AMHR2-OVCAR8 cells. Data are representative of three independent experiments yielding similar results.

The recombinant extracellular domain of human AMHR2 (rhAMHR2-ED; NCBI reference sequence: NG_015981.1; Uniprot Q16671) was generated and purified as an endo-toxin-free C-terminal hexahistidine- (6×His-) tagged fusion protein as previously described in Mazumder et al. (2017) Cancer Prev Res (Phila) 10:612-24. The extracellular domain of human AMHR2 used in the recombinant fusion protein is depicted herein in SEQ ID NO: 11.
Immunization and Generation of Hybridomas Female BALB/cJ mice were purchased from Jackson Laboratory (stock #000651; Bar Harbor, ME) and immunized at 7-8 weeks of age with an emulsion of 100 µg rhAMHR2-ED in 100 µl USP grade water and 100 µl of Sigma Adjuvant System® (#S6322; Sigma-Aldrich, St. Louis, MO). Each mouse received four identical immunizations performed at 2-3-week intervals with the first immunization administered subcutaneously (s.c.) and the three remaining booster immunizations administered intraperitoneally. Three days after the final immunization, spleen cells from immunized mice were fused with the mouse myeloma cell line, Sp2/O-Ag14 (#CRL-1581; American Type Culture Collection (ATCC), Manassas, VA) using polyethylene glycol (PEG; Sigma-Aldrich). The fused hybridoma cells were cultured in DMEM-20/HEPES/pyruvate medium supplemented with hypoxanthine-aminopterin-thymidine (HAT; Thermo Fisher, Waltham, MA) in humidified air at 37° C. with 5% CO2. On day 15, when cells were ~25% confluent, hybridoma supernatants were tested by ELISA as described below for antigen-specific binding to rhAMHR2-ED using recombinant mouse β-casein as the specificity control. Antigen-specific hybridomas were subsequently subcloned by limiting dilution, their supernatants were purified as described above, and the subcloned monoclonal antibodies (mAbs) were isotyped using the Mouse Typer® Isotyping Panel (Bio-Rad, Hercules, CA). Hybridoma clones were grown in DMEM with 10% fetal bovine serum (FBS) or ultra-low IgG FBS (HyClone, Logan, UT) until reaching log phase growth. The mAbs were purified from hybridoma supernatants by protein G chromatography (Genscript Biotech, Piscataway, NJ) using Pierce Protein G IgG Binding Buffer (Thermo Fisher) followed by elution using Pierce IgG Elution Buffer (Thermo Fisher). The mAbs were collected in 1M Tris-HCl at pH 9.0. All collected fractions were concentrated, reconstituted with saline at 1 mg/ml, passed through a 0.22 µm filter, and stored at −20° C. until needed.
Competitive ELISA The specificity of the mAbs was determined by competitive ELISA. Briefly, mAbs were incubated with increasing concentrations of rhAMHR2-ED in liquid phase PBS containing 0.02% Tween-20 (Bio-Rad) for 24 hours at 4° C. The antigen-antibody mixtures were added to the 96-well Maxisorp microtiter plates (Corning Life Sciences, Tewksbury, MA) pre-coated with 4 µg/ml rhAMHR2-ED followed by blocking with 1% BSA (Sigma-Aldrich). Recombinant mouse β-casein was used as the specificity control. Wells were then incubated with a secondary anti-mouse IgG conjugated with horseradish peroxidase (HRP; MilliporeSigma, Burlington, MA) followed by addition of 2,2'-Azino-bis(3-ethylbenzothiazoline-6-sulfonic acid) diammonium salt (ABTS) substrate (Sigma-Aldrich). Optical density was determined by absorbance at 405 nm.
Human EOC Cell Lines The human ovarian carcinoma 8 (OVCAR8) EOC cell line was obtained commercially (ATCC #CVCL-1629) and authenticated by Genetica DNA Laboratories (Burlington, NC). OVCAR8 cells were grown in DMEM supplemented with 10% human sera from postmenopausal women (AMH low/free; BioIVT, Westbury, NY), 5% HEPES buffer (Sigma-Aldrich), 2 mM L-glutamine (Thermo Fisher), and 1% penicillin/streptomycin (Invitrogen, Carlsbad, CA). OVCAR8 cells were periodically tested for Mycoplasma, and their passage number did not exceed 10. The AMHR2-OVCAR8 cell line was generated by cloning transcript variant 1 of human AMHR2 (Accession #NM_020547; Origene, Rockville, MD) into pEZ-M68 vector (GeneCopoeia, Rockville, MD) and using this expression vector to transfect OVCAR8 cells using Lipofectamine™ 3000 (Thermo Fisher). AMHR2-OVCAR8 cells were grown as describe above for the parental OVCAR8 cells.
Generation of EOC Cell Lysates and Western Blotting Lysates from cell lines, tissues, or from fresh human high grade serous ovarian carcinomas (HGSOCs) were prepared by mincing and crushing in DMEM followed by treatment with collagenase (Sigma-Aldrich) and DNase (Invitrogen). The suspension was centrifuged to remove debris, the lysates were washed in PBS, and 25 µg of protein from each lysate was loaded into each lane of denaturing SDS-PAGE gels (Bio-Rad). Gels were transferred onto polyvinylidene difluoride (PVDF) membranes (Bio-Rad) and treated with the 4D12G1 mAb at 0.001 µg/ml as primary antibody. In FIG. 2D, a commercially available AMHR2-ED mAb (#sc-377413; Santa Cruz Biotechnology, Dallas, TX) at 1.0 µg/ml was used instead of the 4D12G1 mAb as the primary antibody for detecting AMHR2-ED. Western blots of lysates were used to detect capase-3-mediated cleavage of poly (ADP-ribose) polymerase-1 (PARP-1) in AMHR2-OVCAR8 cells treated with increasing concentrations of 4D12G1 mAb (1.0-10 µg/ml) by using a primary rabbit antibody for detection of the intact 116 kDa PARP-1 and its 89 kDa cleaved variant associated with apoptosis (Cell Signaling Technology, Danvers, MA). Secondary detection antibodies included treatment with a 1:10,000 dilution of an HRP-conjugated rabbit anti-mouse IgG (MilliporeSigma) or a 1:5,000 dilution of an HRP-conjugated goat anti-rabbit antibody (MilliporeSigma). In all cases, lysate loading was normalized using a primary mAb against β-actin (Sigma-Aldrich), negative control lysates were generated from the human prostate cancer cell line C4-2 (ATTC® #CRL-3314), and blots were developed using the HyGLO™ chemiluminescence system (Thomas Scientific, Swedesboro, NJ).
Immunohistochemistry Immunostaining of human HGSOC and normal adjacent tissues was performed on formalin-fixed, paraffin-embedded, 5 µm sections. Primary antibodies included 0.005 µg/ml of purified 4D12G1 mAb for visualizing AMHR2-ED distribution followed by detection with an HRP-conjugated anti-mouse IgG (Abcam, Cambridge, UK), and rabbit poly-clonal caspase-3 antibody (R&D Systems, Minneapolis, MN) for detecting apoptotic cells followed by an HRP-conjugated anti-rabbit IgG (Abcam).

Flow Cytometry

Harvested cells were treated with Fc-receptor block (BD Biosciences, San Jose, CA) and incubated with either puri-fied mAbs generated against rhAMHR2-ED or with isotype control mouse IgG. Cells were then treated with FITC-labeled goat anti-mouse IgG (BD Biosciences) and analyzed for antigen-specificity by flow cytometry using a FACSAria II flow cytometer and BDFacsDiva software (BD Biosci-ences). Positive control staining was performed using a commercially available mAb against AMHR2-ED (Abcam), whereas mouse IgG1 isotype antibodies (Thermo Fisher) with irrelevant specificities were used as negative controls. Recombinant human AMH (LSBio, Seattle, WA) and recombinant ovalbumin (Sigma-Aldrich) were used in com-petitive binding assays.

Identification of the AMHR2-ED Sequence Recognized by the 4D12G1 mAb

Competitive ELISAs were used to determine the AMHR2-ED sequence recognized by the 4D12G1 mAb. A set of overlapping 16-mer peptides spanning the entire 132 amino acid sequence of human AMHR2-ED was generated. Each peptide shifted by one amino acid and all cysteine residues were replaced by serine to avoid disulfide bond formation (Thermo Fisher). Individual 16-mer peptides were plated in solid phase in microtiter wells, increasing concen-trations of each 16-mer peptide were incubated with the 4D12G1 mAb in liquid phase, and ELISAs were performed as described above. The binding site of the 4D12G1 mAb was confirmed by competitive ELISA using overlapping peptides containing alanine substitutions for each amino acid spanning the immunoreactive region of AMHR2-ED. The substituted peptides were used in liquid phase with the 4D12G1 mAb to determine binding inhibition to rhAMHR2-ED in solid phase. The AMHR2-ED binding sequence of the 4D12G1 mAb and the critical AMHR2-ED residues for such binding were confirmed by SPOT peptide arrays. Peptides spanning the AMHR2-ED 9-40 immunore-active region and ranging from 4-16-mers in length were synthesized >90% pure on cellulose membranes (JPT Pep-tide Technologies, Berlin, Germany), treated overnight with blocking buffer (Thermo Fisher), followed by treatment with the 4D12G1 mAb at 1.0 µg/ml for 3 hours at room tem-perature, followed by three washes with PBS containing 0.01% Tween-20 (Bio-Rad). The membranes were then treated with a 1:10,000 dilution of an HRP-conjugated rabbit anti-mouse IgG (MilliporeSigma) followed by three washes with PBS containing 0.01% Tween-20 (Bio-Rad). Bound antibody was detected using the HyGLO chemilumines-cence system (Thomas Scientific).

Surface Plasmon Resonance (SPR)

The equilibrium dissociation constant ($K_D$) between the 4D12G1 mAb and rhAMHR2-ED was determined by high sensitivity binding in real-time by SPR measured at 25° C. using a Biacore 3000 instrument (GE Healthcare Bio-Sci-ences, Piscataway, NJ). Briefly, the 4D12G1 mAb at 300 nM was diluted in sodium acetate at pH 5.0 and covalently immobilized on carboxymethylated dextran over a gold surface using an aqueous solution of N-ethyl-N'-(3-dimeth-ylaminopropyl)carbodiimide (EDC) and N-hydroxysuccin-imide (NHS; Sigma-Aldrich). The rhAMHR2-ED receptor analyte at different concentrations (10-1-103 nM) in a run-ning buffer containing 10 mM HEPES at pH 7.4, 150 mM NaCl, 3 mM EDTA, and 0.005% P20 detergent was captured with a 30 ml/minute flow over the immobilized 4D12G1 ligand. Regeneration of flow cells was performed using 10 mM glycine (Sigma-Aldrich) at pH 1.7. All sensorgrams were corrected by subtracting the low signal of the control flow cell and the dissociation curve of the 4D12G1 mAb. The $K_D$ values, taking into account affinity and avidity, were calculated using a Langmuir 1:1 fitting model and BIAe-valuation 3.2 software (GE Healthcare Bio-Sciences).

Molecular Modeling of Human AMHR2-ED

Molecular modeling of AMHR2-ED was performed using Phyre2 and 3DLigandSite tools. Four templates were chosen for modeling AMHR2-ED based on heuristics to maximize confidence, percentage identity, and alignment coverage. These templates included: 1) 1bte for the extracellular domain of the activin type 2 receptor (ACVR2); 2) 4fao for activin receptor-like kinase 1 (ALK1); 3) 2hlq for bone morphogenetic protein receptor type 2 (BMPR2); and 4) 2h62 for the ternary ligand-receptor complex of bone mor-phogenetic protein 2 (BMP2). The structure modeling with 100% confidence was chosen for subsequent analysis. The AMHR2-ED protein fragment was visualized using the PyMOL Molecular Graphics System, version 1.5.0.5.

Real-Time Imaging of Programmed Cell Death

AMHR2-OVCAR8 cells were incubated with the green fluorescent dye IncuCyte Cytotox (Essen BioScience, Ann Arbor, MI) for 16 hours in complement-free DMEM at 37° C. with 10 µg/ml of either the 4D12G1 mAb or an IgG1 isotype control mAb. Cell death was imaged in real-time using the IncuCyte S3 live-cell analysis.

Detection of PARP-1 Cleavage

PARP-1 is a 116 kDa nuclear protein that serves as one of the main cleavage targets of caspase-3 resulting in genera-tion of an 89 kDa fragment that can be detected as a signature of programmed cell death. AMHR2-OVCAR8 cells were treated with different concentrations of the 4D12G1 mAb for 24 hours, and cell lysates were examined by Western blots for the presence of intact PARP-1 and its 89 kDa cleaved variant using an antibody that recognizes both the intact PARP-1 and the cleaved PARP-1 (Cell Signaling Technology, Danvers, MA; PARP 46D11 rabbit mAb #9532). Lysates from untreated cells were used as controls, and lysate loading was normalized using a primary mAb against βaActin (Sigma-Aldrich). Blots were devel-oped using the HyGLO™ chemiluminescence system (Thomas Scientific).

Internalization of the 4D12G1 mAb

Internalization of the 4D12G1 mAb following binding to AMHR2-ED in AMHR2-OVCAR8 cells was examined by immunofluorescence. AMHR2-OVCAR8 cells in log-phase growth were treated with 4D12G1 mAb at 5 µg/ml in PBS containing 0.1% BSA (Sigma-Aldrich) for different times at either 37° C. or 4° C. After several washes, cells were fixed with 3.7% formaldehyde and permeabilized with PBS con-taining 0.4% Triton-X100 (Sigma-Aldrich). After washing, cells were incubated with an Alexa Fluor 488-conjugated anti-mouse IgG (Abcam) for 1 hour at room temperature. Nuclei were stained with 4',6-diamidino-2-phenylindole (DAPI; Sigma-Aldrich) for 30 minutes at room temperature, coverslips were mounted on slides using Vectashield Anti-fade Mounting Media (Vector Laboratories, Burlingame, CA), and the cells were visualized by fluorescent micros-copy.

Complement-Dependent Cytotoxicity (CDC) Assay

AMHR2-OVCAR8 cells were washed and treated with different concentrations of the 4D12G1 mAb or an isotype control mAb. The cells were then incubated in 96-well flat-bottom plates (Corning Life Sciences) with either 10% normal human sera or 10% heat-inactivated normal human sera. After 4 hours, supernatant samples were removed and the cultures were treated with lysis buffer. Extracellular and total lactate dehydrogenase (LDH) activities were quantified using the CyQUANT LDH Cytotoxicity Assay kit (Thermo Fisher) that measures LDH catalyzed conversion of lactate to pyruvate and subsequent reduction of a tetrazolium salt to a red formazan product measured at 490 nm. The level of formazan formation is directly proportional to the amount of LDH activity released into the medium and the percent of LDH released was determined by the measured total LDH activity detected in the cultured cells.

Antibody-Dependent Cellular Phagocytosis (ADCP) Assay

Target AMHR2-OVCAR8 cells were labeled with Cell-Tracker Green CMFDA Dye (Thermo Fisher) and incubated with varying concentrations of the 4D12G1 mAb or an isotype control mAb in DMEM supplemented with 10% FBS. After 30 minutes, differentiated macrophages derived from C57BL/6 bone marrow (Sciencell Research Laboratories, Carlsbad, CA) were added as effector cells at an effector to target cell ration of 10:1. After 3 days, ADCP was determined by flow cytometry determination of the percentage of live target cells.

OVCAR8 and Patient-Derived Xenografts (PDXs)

Female athymic nude mice (NU/J, JAX stock #002019) were purchased at 6-8 weeks of age (Jackson Laboratory) for use as recipients of OVCAR8 xenografts. Female NOD-scid IL2Rgamma$^{null}$ (NSG) immunodeficient mice were purchased at 6-8 weeks of age from the Cleveland Clinic Biological Resources Unit (Cleveland, OH). $5 \times 10^6$ OVCAR8 cells were injected s.c. into the flank of (A) NSG mice and (B) athymic nude mice aged 6-8 weeks. When tumors became palpable at about 50 mm$^3$, mice were injected intraperitoneally (i.p.) with 200 μg of 4D12G1 mAb or isotype control mAb once a week for 5 continuous weeks. Experiments were terminated when the tumor reached 3 cm3. PDXs were generated by implanting HGSOCs from patients into female NSG mice aged 6-8 weeks. Freshly excised tumors were cut into approximately 2 mm$^3$ sized fragments and implanted s.c. into the flank area followed by a drop of Matrigel chilled at 4° C. (Corning Life Sciences). Mice implanted directly with patient tumor samples were designated as P1. Tumor growth was accessed periodically using a Vernier caliper. P1 endpoint tumors were dissected and implanted into new female NSG mice as described above. Passages ≥P2 were used to study the efficacy of i.p. injection of 200 μg of the 4D12G1 mAb or an isotype control mAb once a week for 5 continuous weeks starting when the tumor became palpable.

Quantification of AMHR2 Receptor Density on the Surface of EOC Cells

AMHR2 receptor density was measured on tumor cells obtained from OVCAR8 xenografts and PDXs using the QIFIKIT® series of 6 bead populations coated with different but well-defined quantities of a mouse mAb (Agilent Technologies, Carpinteria, CA). The specimen cells were labelled at a saturating concentration with the 4D12G1 mAb as the primary antibody so that the number of bound 4D12G1 mAb antibody molecules corresponded to the number of antigenic sites. The cells were then incubated in parallel with the QIFIKIT® beads, with a FITC-conjugated polyclonal goat anti-mouse immunoglobulin, and with a goat F(ab')2 at saturating concentration. A calibration curve was constructed by plotting the mean fluorescence intensity (MFI) of the individual bead populations against the number of mAb molecules on the beads. The number of antigenic sites on the specimen cells were then determined by interpolation and expressed as the number of AMHR2 receptors/cell.

Biostatistical Analysis

Differences in tumor sizes, CDC assays, and competitive ELISA analysis of epitope mapping were compared using two-way analysis of variance (ANOVA). Differences in ADCP assays and binding of monoclonal antibodies to human cells by flow cytometry were compared using the one sample student t-test. All differences were considered statistically significant when P≤0.05 (95% confidence interval). All experiments were repeated 3 times independently.

Results

Generation of mAbs Specific for rhAMHR2-ED

Approximately 300 hybridoma supernatants were screened by ELISA for specificity against rhAMHR2-ED using recombinant mouse β-casein as the specificity control. Twelve hybridomas showed high-titer AMHR2-ED-specific responses (FIG. 1A). Based on flow cytometry binding analysis to OVCAR8 cells (data not shown), the 4D12 parental hybridoma was selected for subcloning by limiting dilution. The subcloning of 4D12 produced the three subclones, 4D12C6, 4D12C7, and 4D12G1 each of which expressed the IgG1/κ-chain isotype (FIG. 1B) and showed antigen-specificity in competitive ELISA (FIG. 1C) and in flow cytometry analysis of OVCAR8 cells (FIG. 1D). The 4D12G1 mAb was examined further.

The 4D12G1 mAb included a VH sequence depicted in SEQ ID NO: 7 (including a CDR-H1 depicted in SEQ ID NO: 1, a CDR-H2 depicted in SEQ ID NO: 2, and a CDR-H3 depicted in SEQ ID NO: 3), and a VL sequence depicted in SEQ ID NO: 8 (including a CDR-L1 depicted in SEQ ID NO: 4, a CDR-L2 depicted in SEQ ID NO: 5, and a CDR-L3 depicted in SEQ ID NO: 6).

The 4D12G1 mAb Recognizes AMHR2 in Human EOC

The 4D12G1 mAb was used to detect AMHR2 in primary cultures of human EOC cells derived from fresh HGSOC tissues. Flow cytometry analysis showed that 4D12G1 detected AMHR2 in 58.2% of the primary HGSOC-1 cells and in 93.7% of the primary HGSOC-2 cells with isotype control mAb binding to only 1.5% and 1.1% of cultured cells, respectively (FIG. 2A). By Western blot analysis, the 4D12G1 mAb immunostained seven different primary HGSOC tissue lysates as well as a positive control lysate derived from an ovary taken from a normal young C57BL/6 female mouse, thereby indicating the cross-reactive features of the 4D12G1 mAb in recognizing both human and mouse AMHR2-ED (FIG. 2B). The 4D12G1 mAb did not immunostain a negative control lysate derived from the C4-2 human prostate cancer cell line. Immunostaining with a 0-actin antibody (Sigma-Aldrich) was used to confirm normalized lysate loading. The 4D12G1 mAb was used in immunohistochemical staining of 13 primary HGSOC tissues from women with a mean age 60.2 years, range 38-76 years (Table 1) and in the normal fallopian tube tissues adjacent to the EOC tumors. Provided are the results obtained from patients 1-4 with a mean age 64 years, range 59-70 years. Arrows indicate staining of the four HGSOC tumor parenchymas (FIG. 2C, left column) with no staining of the stromal areas and no staining of any areas of the normal adjacent fallopian tube tissues (FIG. 2C, right column). The four normal adjacent fallopian tube tissues that did not stain with the 4D12G1 mAb were from 59-70 year-old postmenopausal women, and therefore would not be expected to express AMHR2-ED, a protein domain 'retired' from expression in postmenopausal ovaries.

TABLE 1

| Details of EOC patients and their examined tumors | | | | |
|---|---|---|---|---|
| HGSOC Sample | Diagnosis[1] | Age[2] | Disease Stage | Immunohistochemical Intensity of AMHR2 Expression |
| 1 | HGSOC | 61 | Primary | ++ |
| 2 | HGSOC | 59 | Primary | +++ |
| 3 | HGSOC | 66 | Primary | +++ |
| 4 | HGSOC | 70 | Primary | ++ |
| 5 | HGSOC | 58 | Primary | +++ |
| 6 | HGSOC | 38 | Primary | +++ |
| 7 | HGSOC | 43 | Primary | +++ |
| 8 | HGSOC | 76 | Primary | +++ |
| 9 | HGSOC | 65 | Primary | +++ |
| 10 | HGSOC | 65 | Primary | +++ |
| 11 | HGSOC | 55 | Primary | ++ |
| 12 | HGSOC | 59 | Primary | +++ |
| 13 | HGSOC | 68 | Primary | ++ |

[1]All examined tissues came from patients diagnosed with high grade serous ovarian carcinoma (HGSOC)
[2]Mean age of EOC patients = 60.2 years (range, 38-76)

The 4D12G1 mAb Competes with AMH for Binding to AMHR2

Unlike primary human HGSOC tissues, human EOC cell lines typically show low expression levels of AMHR2. Thus, we transfected OVCAR8 cells with the full sequence of human AMHR2 to have a useful reagent for further analysis of the features of the 4D12G1 mAb. Western blot analysis of lysates from the stably transfected AMHR2-OVCAR8 cell line showed high level detection of AMHR2 protein compared to parental OVCAR8 cells with no detectable AMHR2 in lysates from the human prostate cancer cell line, C4-2 (FIG. 2D). Flow cytometry analysis showed that the 4D12G1 mAb binds to 91% of AMHR2-OVCAR8 cells (FIG. 2E), and competitive binding studies showed that the cognate recombinant AMH ligand for AMHR2 was able to compete effectively in a dose-dependent manner with the 4D12G1 mAb for binding to AMHR2-OVCAR8 cells (FIG. 2F). This binding by the 4D12G1 mAb to the AMHR2-OVCAR8 cells was unaffected by dose-response treatment with recombinant ovalbumin thereby indicating the specificity of AMH for competing with the binding of the 4D12G1 mAb (FIG. 2G).

Identification of the AMHR2-ED Binding Site for the 4D12G1 mAb

Figure 3:
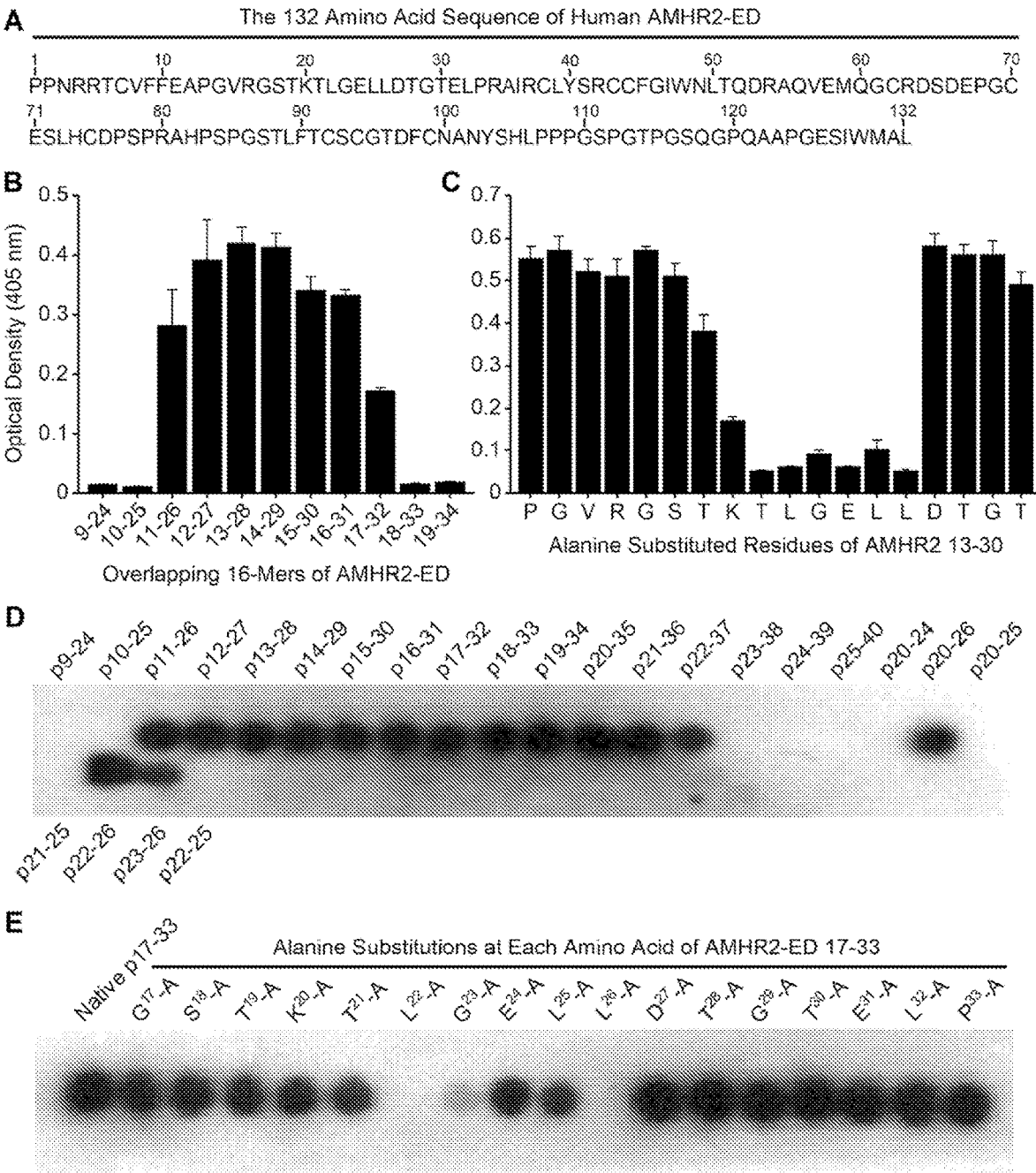
FIG. 3 shows identification of the AMHR2-ED binding site for the 4D12G1 mAb. (A) The entire 132 amino acid sequence of human AMHR2-ED is shown. (B) An overlapping series of 16-mer peptides spanning the entire sequence of human AMHR2-ED with one amino acid shifts were plated for direct ELISA testing using the 4D12G1 mAb as the primary antibody. The 4D12G1 mAb recognized residues AMHR2-ED 11-32. (C) Overlapping peptides spanning AMHR2-ED 13-30 were synthesized with alanine substitutions at each N-terminal residue or with glycine substitutions for any native N-terminal alanine residues. Competitive ELISA results showed that alanine substitutions at residues spanning AMHR2-ED 20-26 ([20]KTLGELL[26]) (SEQ ID NO: 13) decreased binding of the 4D12G1 mAb to AMHR2-ED. (D) SPOT peptide arrays using 4-16-mer peptides spanning AMHR2-ED 9-40 were immobilized on cellulose membranes, treated with the 4D12G1 mAb, and the bound antibody was detected by chemiluminescence. The results showed that the AMHR2-ED 22-26 5-mer sequence ([22]LGELL[26])(SEQ ID NO: 14) represents the minimal sequence for binding of the 4D12G1 mAb. (E) SPOT peptide arrays were made using membrane bound 17-mer peptides spanning the AMHR2-ED 17-33 domain and containing alanine substitutions at each sequential amino acid. Alanine replacement of Leu22, Gly23, and Leu26 completely abolished binding by the 4D12G1 mAb. All error bars indicate ±SD, and all experiments are representative of three experiments yielding similar data.

An overlapping series of 16-mer peptides spanning the entire 132 amino acid sequence of human AMHR2-ED (FIG. 3A) with moving single amino acid shifts were plated for direct ELISA testing using the 4D12G1 mAb as primary antibody. The ELISA binding results showed that the 4D12G1 mAb recognized peptides spanning residues 11-32 [11]EAPGVRGSTKTLGELLDTGTEL[32] (SEQ ID NO: 12) of AMHR2-ED (FIG. 3B). To determine amino acids recognized by the 4D12G1 mAb, an overlapping series of peptides spanning the immunoreactive sequence comprising AMHR2-ED 13-30 were synthesized with alanine substitutions at each N-terminal residue or with glycine substitutions for any native N-terminal alanine. These peptides were used in competitive ELISAs to determine which residues inhibit binding of the 4D12G1 mAb with solid phase rhAMHR2-ED. The results showed that alanine substitutions spanning AMHR2-ED 20-26 [20]KTLGELL[26] (SEQ ID NO: 13) dramatically decreased binding of the 4D12G1 mAb to AMHR2-ED (FIG. 3C). To determine the minimal AMHR2-ED sequence involved in the binding of the 4D12G1 mAb, SPOT peptide arrays were generated spanning the immunoreactive region of AMHR2-ED. Peptides ranging from 4-16-mers in length were immobilized on cellulose membranes and treated with the 4D12G1 mAb. Bound antibody was detected by chemiluminescence. The results showed that AMHR2-ED 22-26 [22]LGELL[26] (SEQ ID NO: 14) represents the minimal sequence needed for binding of the 4D12G1 mAb (FIG. 3D). Additional binding details were obtained using SPOT arrays with membrane bound 17-mer peptides spanning the immunoreactive region and containing alanine substitutions at each N-terminal residue. The results showed that alanine replacement of Leu22, Gly23, and Leu26 residues of the [20]KTLGELL[26] (SEQ ID NO: 13) sequence completely abolished binding by the 4D12G1 mAb (FIG. 3E). Thus, L22, G23, and L26 represent essential residues for binding of the 4D12G1 mAb. Finally, we used surface plasmon resonance (SPR) to measure the equilibrium dissociation constant ($K_D$) between the 4D12G1 mAb and AMHR2-ED at 119 pM (data not shown).

Molecular Modeling of Human AMHR2-ED

Figure 4:
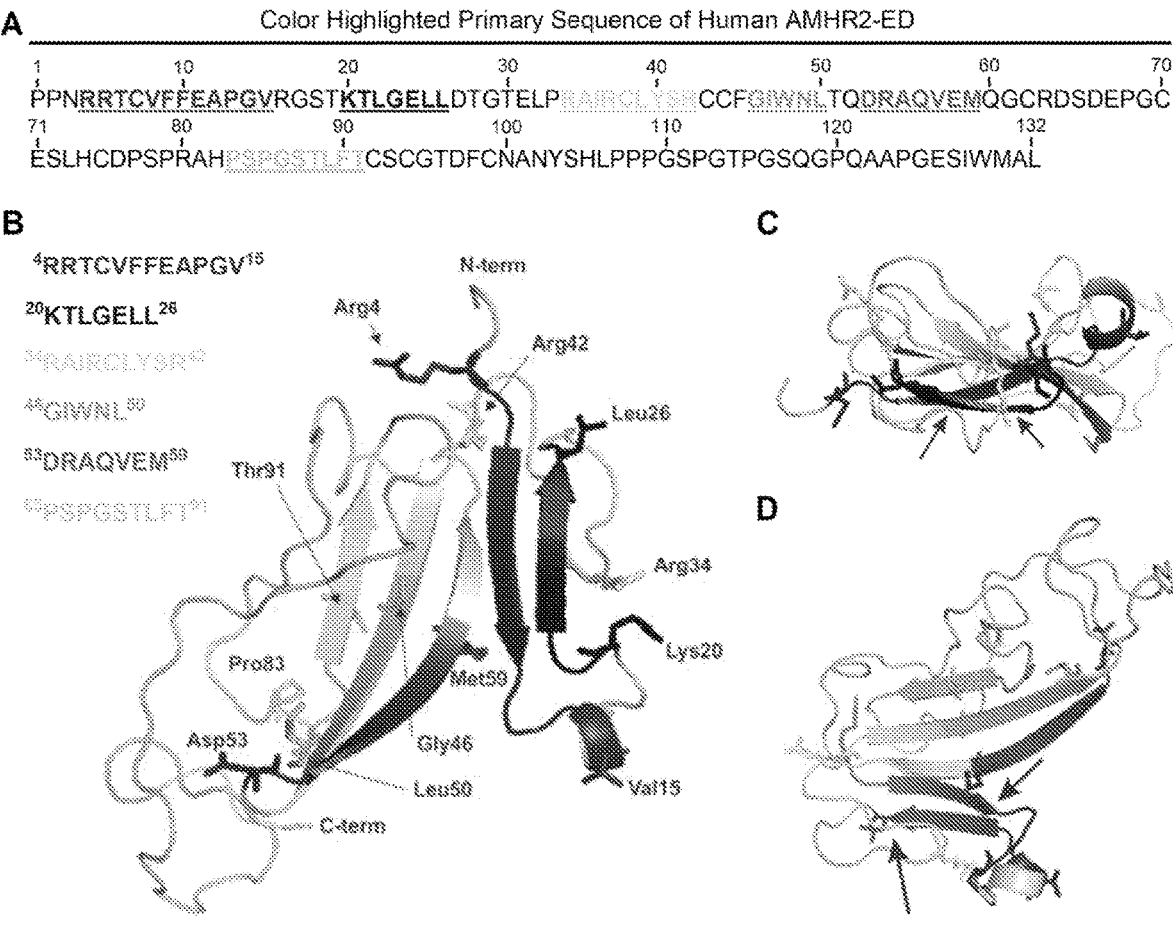
FIG. 4 shows molecular modeling of human AMHR2-ED (SEQ ID NO: 11). Proposed binding sites for the cognate AMH ligand include the key natural AMH binding site I, [4]RRTCVFFEAPGV[15] (SEQ ID NO: 15) represented in red in (A) the primary amino acid sequence and as a red beta sheet in (B) the ribbon model juxtaposed but antiparallel to the $^{20}$KTLGELL$^{26}$ (SEQ ID NO: 13) binding site of the 4D12G1 mAb depicted in blue in both the primary sequence and as a beta sheet in the ribbon model. Another strong AMH binding site II, $^{34}$RAIRCLYSR$^{42}$ (SEQ ID NO: 16) is represented by a long yellow loop also adjacent to the $^{20}$KTLGELL$^{26}$ (SEQ ID NO: 13) binding site of the 4D12G1 mAb. In contrast, the $^{53}$DRAQVEM$^{59}$ (SEQ ID NO: 17) binding site of the 12G4 mAb and its 3C23K humanized and glyco-engineered variant (a.k.a. GM102) is closer to the weaker tertiary and quaternary AMH binding sites $^{46}$GIWNL$^{50}$ (SEQ ID NO: 18) and $^{83}$PSPGSTLFT$^{91}$ (SEQ ID NO: 19), respectively. Arrows point to the juxtaposition of the blue $^{20}$KTLGELL$^{26}$ (SEQ ID NO: 13) binding site of the 4D12G1 mAb with the red AMH I binding site, $^{4}$RRTCVFFEAPGV$^{15}$ (SEQ ID NO: 15) and the yellow AMH binding site II $^{34}$RAIRCLYSR$^{42}$ (SEQ ID NO: 16) in (C) a top view of the ribbon model as well as in (D) a 90° rotational view.

To image the binding site region of the 4D12G1 mAb in the context of the entire AMHR2-ED protein, molecular modeling was performed using Phyre2 and 3DLigandSite tools and the highest confidence model was visualized using the PyMOL Molecular Graphics System, version 1.5.0.5. Proposed binding sites for the AMH cognate ligand include the key natural AMH I binding site spanning AMHR2-ED 4-15 [4]RRTCVFFEAPGV[15] (SEQ ID NO: 15) represented in red in the primary amino acid sequence (FIG. 4A) and as a red beta sheet in the ribbon model juxtaposed but antiparallel to the [20]KTLGELL[26] (SEQ ID NO: 13) binding site of the 4D12G1 mAb depicted in blue in both the primary sequence (FIG. 4A) and as a beta sheet in the ribbon model (FIG. 4B). Another strong AMH II binding site spanning AMHR2-ED 34-42 [34]RAIRCLYSR[42] (SEQ ID NO: 16) is represented by a long yellow loop also adjacent to the [20]KTLGELL[26] (SEQ ID NO: 13) binding site of the 4D12G1 mAb (FIG. 4B). The weak AMH III binding site spanning AMHR2-ED 46-50 [46]GIWNL[50] (SEQ ID NO: 18) in green and an even weaker AMH IV binding site spanning AMHR2-ED 83-91 [83]PSPGSTLFT[91] (SEQ ID NO: 19) in cyan are located quite distant from the [20]KTLGELL[26] (SEQ ID NO: 13) binding site of the 4D12G1 mAb (FIG. 4B). The juxtaposition of the blue [20]KTLGELL[26] (SEQ ID NO: 13) binding site of the 4D12G1 mAb with the red AMH I binding site [4]RRTCVFFEAPGV[15] (SEQ ID NO: 15) and the yellow AMH II binding site [34]RAIRCLYSR[42] (SEQ ID NO: 16) is also evident in a top view of the ribbon model (FIG. 4C) as well as in a 90° rotational view (FIG. 4D). Thus, the AMHR2-ED binding site recognized by the 4D12G1 mAb is in close proximity to the key primary and secondary AMH binding sites, a feature that likely accounts for the ability of AMH to compete with the 4D12G1 mAb for binding to AMHR2-ED (FIG. 2F). This view is supported by the fact that another characterized mAb against AMHR2-ED, the 12G4 mAb, is unable to compete with AMH for AMHR2-ED receptor binding likely because it recognizes the [53]DRAQVEM[59] (SEQ ID NO: 17) sequence of AMHR2-ED (in purple throughout FIG. 4) far from the strong AMH I and AMH II binding sites and much closer to the AMH III and AMH IV binding sites associated with weak binding of AMH to AMHR2-ED.

The 4D12G1 mAb Induces Programmed Cell Death of EOC Cells

Figure 5:
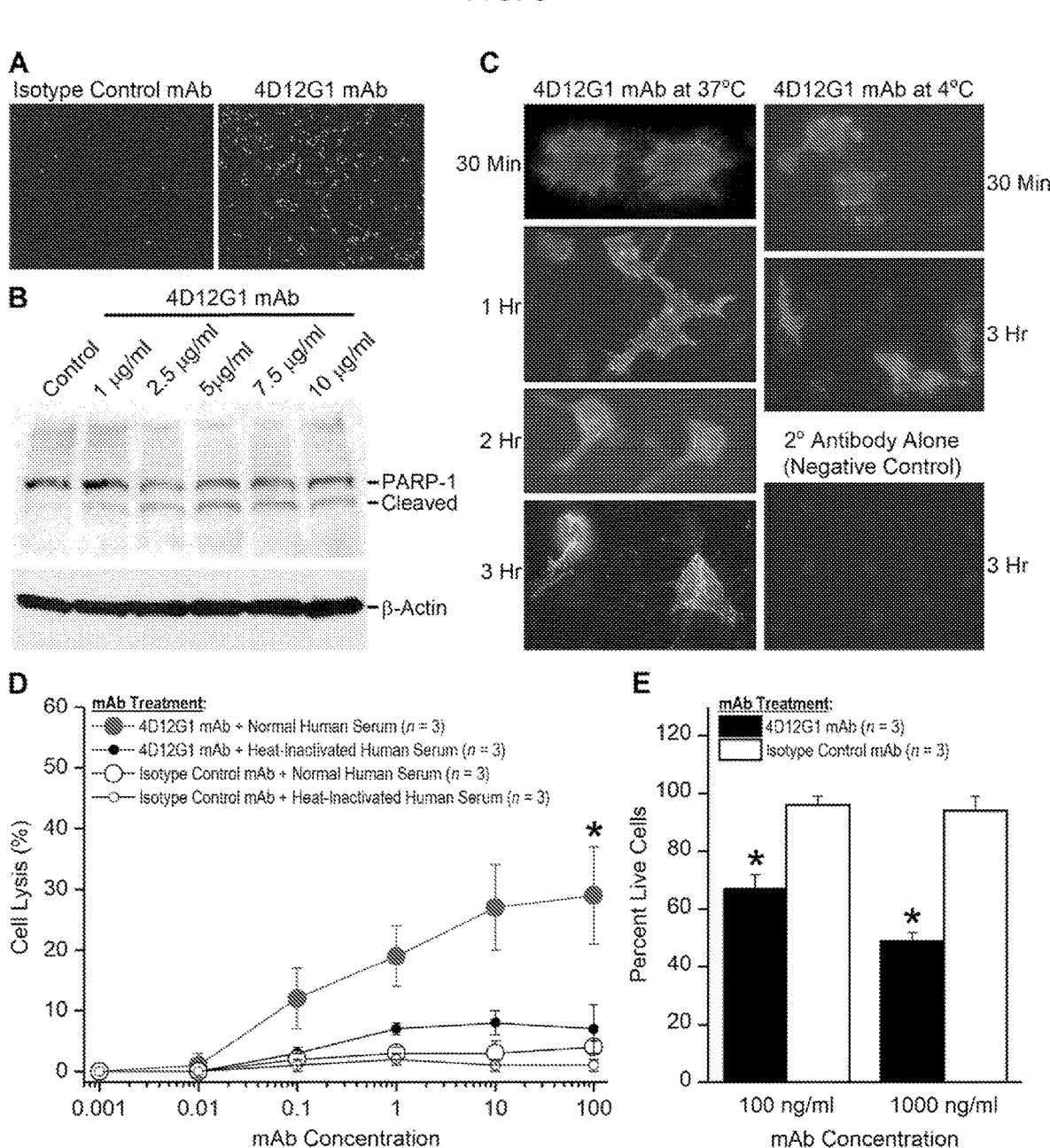
FIG. 5 shows that 4D12G1 mAb kills EOC cells by inducing apoptosis, CDC, and ADCP. (A) To assess whether the 4D12G1 mAb induced apoptosis of EOC cells, AMHR2-OVCAR8 cells were treated with a green fluorescent dye and the 4D12G1 mAb in DMEM supplemented with heat-inactivated serum and assessed for induction of apoptosis in real-time by live imaging using the IncuCyte S3 live-cell analysis system. Treatment with the 4D12G1 mAb for 16 hours induced substantial apoptosis (A, right panel) compared to treatment with an IgG1 isotype control mAb (A, left panel). (B) AMHR2-OVCAR8 cells were treated with different concentrations of the 4D12G1 mAb for 24 hours and Western blots of the cell lysates showed detection of the intact 116 kDa PARP-1 and its 89 kDa cleaved variant consistent with apoptosis. Immunostaining with a R-actin antibody was used to confirm normalized lysate loading. (C) AMHR2-OVCAR8 cells were incubated with the 4D12G1 mAb for different periods of time at either 37° C. (B, left column) or 4° C. (B, right column). Complexes of the 4D12G1 mAb with the AMHR2 receptor became evident in the cytoplasm of AMHR2-OVCAR8 cells by 1 hour after treatment at 37° C., and clustered patterns of cytoplasmic antibody-receptor complexes became increasingly more prominent 2 and 3 hours after treatment at 37° C., all consistent with induction of apoptosis. Treatment with the 4D12G1 mAb at 4° C. showed few cytoplasmic antibody-receptor complexes 3 hours after treatment and no staining occurred in cells treated with secondary antibody alone (C, right column, bottom panel). (D) To determine whether the 4D12G1 mAb induced CDC of EOC cells, AMHR2-OVCAR8 cells were incubated in either 10% normal human serum or 10% heat-inactivated human serum and treated for 4 hours with varying doses of either 4D12G1 mAb or isotype control mAb. Cell lysis was measured by release of LDH activity and occurred only in cells treated with the 4D12G1 mAb. (E) To determine whether the 4D12G1 mAb induced ADCP of EOC cells, AMHR2-OVCAR8 target cells were labeled with a green fluorescent dye and incubated with two different concentrations of 4D12G1 mAb or isotype control mAb for 30 minutes in the absence of any serum. The washed cells were mixed with effector macrophages from C57BL/6 mouse bone marrow at an effector to target cell ratio of 10:1, and the target cells were analyzed by flow cytometry 3 days later. Target cell death occurred only in cells treated with the 4D12G1 mAb. All error bars indicate ±SD, and all experiments are representative of three experiments yielding similar data.

To determine whether the 4D12G1 mAb inhibits the growth of EOC tumors by antibody-mediated induction of programmed cell death, we assessed real-time induction of apoptosis by live imaging of the AMHR2-OVCAR8 cells treated in vitro with the 4D12G1 mAb in DMEM supplemented with heat-inactivated serum. The results indicated that treatment for 16 hours with the 4D12G1 mAb induced a profound level of apoptosis in AMHR2-OVCAR8 cells (FIG. 5A; right panel) compared to treatment for 16 hours with an isotype control IgG1 mAb (FIG. 5A; left panel).

Detection of PARP-1 Cleavage

PARP-1 is a 116 kDa nuclear protein that serves as one of the main cleavage targets of caspase-3 resulting in generation of an 89 kDa fragment that can be detected as a signature of programmed cell death. Thus, we examined whether the 4D12G1 mAb was able to cleave PARP-1 as a consequence of inducing an apoptotic signal. AMHR2-OVCAR8 cells were treated with different concentrations of the 4D12G1 mAb for 24 hours, and cell lysates were examined by Western blots for the presence of the cleaved 89 kDa PARP-1 fragment. The results showed that cleaved PARP-1 was detected in the lysates at 4D12G1 mAb doses as low as 1.0 µg/ml (FIG. 5B). Immunostaining with a R-actin antibody (Sigma-Aldrich) was used to confirm normalized lysate loading.

Internalization of AMHR2-mAb Complexes

Since cognate AMH/AMHR2 signaling involves endocytic receptor internalization, we examined whether this process occurs in the AMHR2-OVCAR8 cells treated with the 4D12G1 mAb. AMHR2-OVCAR8 cells were incubated with the 4D12G1 mAb for different periods of time at either 37° C. (FIG. 5C; left column) or 4° C. (FIG. 5C; right column). Complexes of the 4D12G1 mAb with the AMHR2 receptor were evident in the cytoplasm of the AMHR2-OVCAR8 cells by 1 hour after treatment with the 4D12G1 mAb at 37° C., and clustered patterns of cytoplasmic mAb-receptor complexes were increasingly more prominent 2 and 3 hours after treatment at 37° C. In contrast, treatment with the 4D12G1 mAb at 4° C. showed virtually no cytoplasmic antibody-receptor complexes even 3 hours after treatment (FIG. 5C; right column, middle panel). Staining was not observed in cells treated with secondary detection antibody alone (FIG. 5C; right column, lower panel). Our results indicate that signaling induced by binding of the 4D12G1 mAb to AMHR2 results in apoptosis of EOC cells accompanied by endocytic internalization of the mAb-AMHR2 complexes and caspase-3 mediated cleavage of PARP-1.

The 4D12G1 mAb Induces EOC Cell Lysis by CDC

The ability of the 4D12G1 mAb to mediate CDC was determined. AMHR2-OVCAR8 cells were treated in vitro for 4 hours with varying doses of the 4D12G1 mAb in the presence of either 10% normal human serum containing complement or 10% normal human serum heated to inactivate complement. Additional controls included AMHR2-OVCAR8 cells treated for 4 hours with varying doses of an isotype control mAb in the presence of either 10% normal human serum or 10% heat-inactivated human serum. Cell lysis was measured by release of lactate dehydrogenase activity. The results showed that the 4D12G1 mAb induced significantly increased cell lysis (P<0.0001) in the presence of normal human serum containing complement compared to the lysis induced by the 4D12G1 mAb in the presence of heat-inactivated human serum (FIG. 5D).

The 4D12G1 mAb Induces EOC Cell Lysis by ADCP

The ability of the 4D12G1 mAb to mediate ADCP was determined. AMHR2-OVCAR8 target cells were labeled with a green fluorescent dye and incubated with two different concentrations of 4D12G1 mAb or isotype control mAb for 30 minutes in the absence of any serum. The washed cells were mixed with effector macrophages from C57BL/6 mouse bone marrow at an effector to target cell ratio of 10:1, and the percentage of live target cells were determined by flow cytometry 3 days later. The percentage of live target cells were significantly lower in AMHR2-OVCAR8 cells treated with the 4D12G1 mAb at 100 ng/ml (P=0.001) and at 1000 ng/ml (P=0.0002; FIG. 5E) compared to the same treatments with the isotype control mAb.

The 4D12G1 mAb Inhibits Growth of Xenografted Human EOCs

Figure 6:
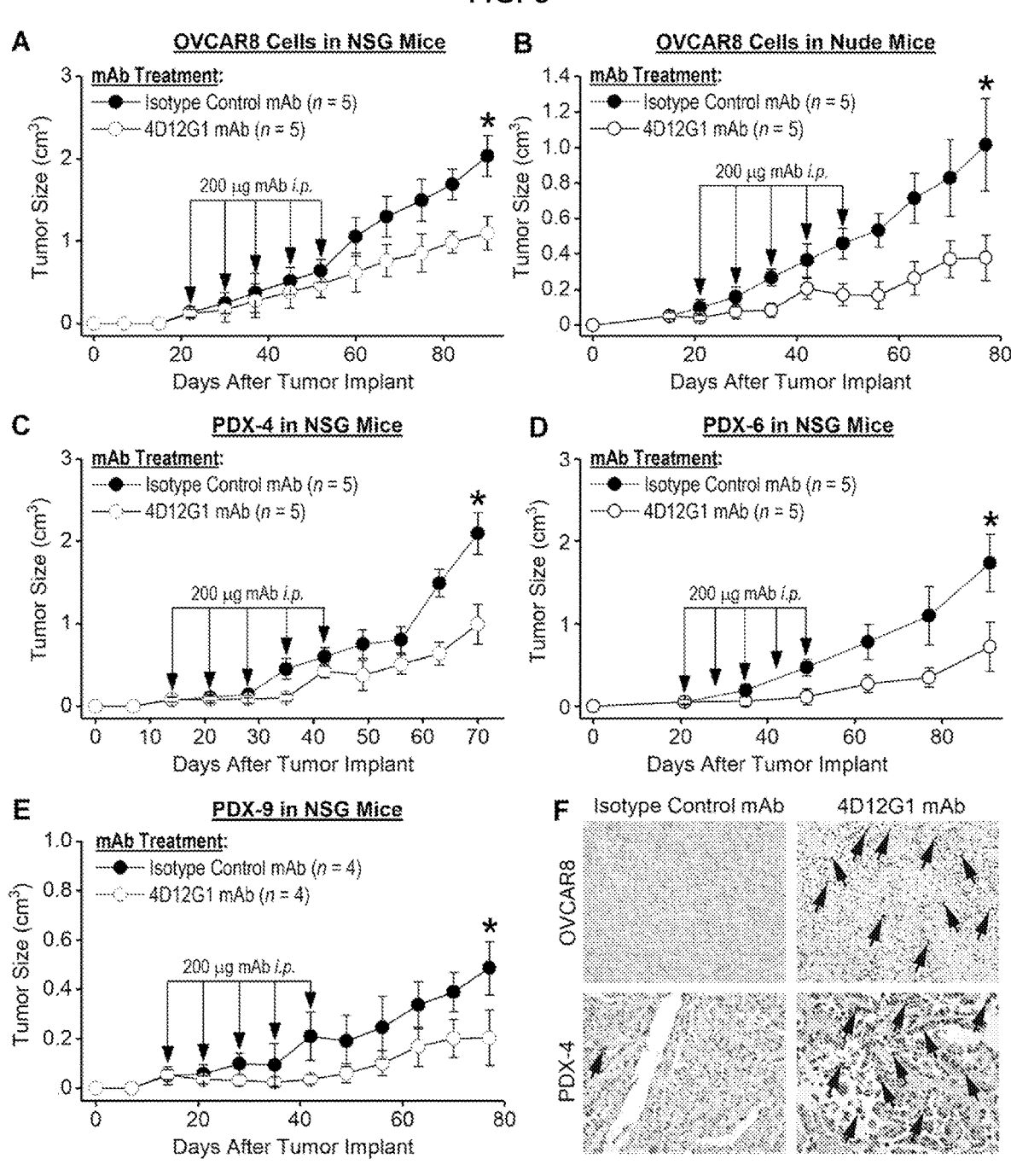
FIG. 6 shows that the 4D12G1 mAb inhibits growth of human EOC xenografts. Human EOC tumors were injected s.c. into immunodeficient mice. When tumors became palpable, mice were injected i.p. with 200 μg of either the 4D12G1 mAb or an isotype control mAb weekly for 5 continuous weeks. Treatment with the 4D12G1 mAb significantly inhibited the growth of OVCAR8 tumors in (A) severely immunodeficient NSG mice (P<0.001) and in (B) T cell-deficient athymic nude mice (P<0.0001). Treatment with the 4D12G1 mAb significantly inhibited the growth of three primary HGSOC tumors (P<0.0001 in all cases) generated from recently diagnosed patients and xenografted into immunodeficient NSG mice including (C) PDX-4, (D) PDX-6, and (E) PDX-9. (F) Detection of caspase-3 positive cells in the OVCAR8 (F, upper row) and PDX-4 tumors (F, lower row) from NSG mice at 20× is shown by arrows in mice treated with the 4D12G1 mAb (F, right column) compared to mice treated with isotype control mAb (F, left column). Caspase-3 data shown are representative of three experiments yielding similar results. All error bars indicate ±SD.

OVCAR8 cells and human HGSOC tumors were injected s.c. into the flanks of immunodeficient mice. When tumors became palpable at about 50 mm³, mice were injected i.p. with 200 µg of either the 4D12G1 mAb or an isotype control mAb weekly for 5 continuous weeks. The results showed that treatment with the 4D12G1 mAb significantly inhibited the growth of OVCAR8 tumors in severely immunodeficient NSG mice (P<0.001; FIG. 6A) or in T cell-deficient athymic nude mice (P<0.0001; FIG. 6B). Increased significant inhibition of tumor growth in athymic nude mice compared to NSG mice may reflect the absence of a hemolytic complement system, reduced dendritic cell function, and defective macrophage activity characteristic of NSG mice but not athymic nude mice thereby precluding contributions of CDC and ADCP immune mechanisms in the NSG anti-tumor response. Treatment with the 4D12G1 mAb significantly inhibited the growth (P<0.0001 in all cases) of three primary HGSOC tumors generated from recently diagnosed patients and xenografted into immunodeficient NSG mice including PDX-4 (FIG. 6C), PDX-6 (FIG. 6D), and PDX-9 (FIG. 6E). Detection of caspase-3 positive cells in the OVCAR8 tumor grown in an NSG mouse (FIG. 6F, upper row) and the PDX-4 tumor grown in an NSG mouse (FIG. 6F, lower row) is shown at 20x by arrows in mice treated with the 4D12G1 mAb (FIG. 6F, right column) compared to mice treated with an isotype control mAb (FIG. 6F, left column). Caspase-3 data shown are representative of three experiments yielding similar results. All error bars indicate ±SD.

Quantification of AMHR2 Receptor Density on the Surface of EOC Cells

As few as 4,000 AMHR2 receptors/cell may be sufficient to mediate inhibition of EOC growth in xenografts by an AMHR2-ED-specific mAb. To further examine this issue, we used the QIFIKIT® series of coated beads (Agilent Technologies) and flow cytometry analysis to measure the cell surface density of AMHR2 receptors on the EOC cells xenografted into immunodeficient mice. Cell surface densities of AMHR2 receptors were 2,674, 3,917, 2,674, 22,286, 8,907, and 10,067 receptors/cell measured, respectively, on OVCAR8 cells xenografted into nude mice, OVCAR8 cells xenografted into NSG mice, and PDX-4, PDX-6 and PDX-9 HGSOC tumor cells xenografted into NSG mice (data not shown). These results indicate that 2,674 receptors/cell are sufficient for the 4D12G1 mAb to mediate inhibition of EOC growth in xenografts differing somewhat from the 4,000 AMHR2 receptors/cell threshold indicated previously. These data show that human HGSOC tumors have enough AMHR2 molecules on their cell surface to provide sufficient available targets for mediating immunotherapy of ovarian cancer by treatment with the 4D12G1 mAb.

Together, the results in this Example show that 4D12G1 mAb is an IgG1 that shows high affinity antigen-specific binding to human AMHR2-ED in ELISA, in lysates of human EOC tumors, and in immunostained human EOC tissues. The 4D12G1 mAb recognizes the 7-mer AMHR2-ED sequence [20]KTLGELL[26] (SEQ ID NO: 13) that lies adjacent to the primary and secondary binding sites of the cognate anti-Müllerian hormone (AMH) ligand thereby allowing the 4D12G1 mAb to compete effectively with AMH for binding to the AMHR2-ED cognate receptor. 4D12G1 IgG1 mAb binds AMHR2-ED with a high affinity $K_D$ of 119 pM, and functions like the human AMH cognate ligand by inducing substantial apoptosis of AMHR2-expressing human EOC cells accompanied by endocytic internalization of receptor-mAb complexes and caspase-3 mediated cleavage of PARP-1. Additionally, the 4D12G1 mAb significantly inhibits the growth of human EOC xenografts in immunodeficient mice through a predominant apoptotic mechanism but is also capable of inducing CDC and ADCP against EOC cells.

INCORPORATION BY REFERENCE

The entire disclosure of each of the patent and scientific documents referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

INFORMAL SEQUENCE LISTING

| SEQ ID NO | Description | Sequence |
|---|---|---|
| 1 | CDR-H1 | RYFMS |
| 2 | CDR-H2 | AINSDGGRTYYPDTVKG |
| 3 | CDR-H3 | HIYSYYEDYFDY |
| 4 | CDR-L1 | RSSQSLVHSNGNTYLH |
| 5 | CDR-L2 | KVSKRFS |
| 6 | CDR-L3 | SQSTHVYT |
| 7 | VH | DVKLVESGGGLVKLGGSLKLSCAASGFTFSRYFMSWVRQTPEKRLELVAAIN SDGGRTYYPDTVKGRFTISRDNAKNTLYLQMSSLKSEDTALYYCTRHIYSYY EDYFDYWGQGTTLTVSS |
| 8 | VL | DVVMTQTPLSLPVSLGDQASISCRSSQSLVHSNGNTYLHWYLQKPGQSPKLL IYKVSKRFSGVPDRFSGSGSGTDFTLKISRVEAEDLGVYFCSQSTHVYTFGG GTKLEIK |
| 9 | Full human Anti-Müllerian Hormone Receptor II protein, Uniprot Q16671 | MLGSLGLWALLPTAVEAPPNRRTCVFFEAPGVRGSTKTLGELLDTGTELPRA IRCLYSRCCFGIWNLTQDRAQVEMQGCRDSDEPGCESLHCDPSPRAHPSPGS TLFTCSCGTDFCNANYSHLPPPGSPGTPGSQGPQAAPGESIWMALVLLGLFL LLLLLLGSIILALLQRKNYRVRGEPVPEPRPDSGRDWSVELQELPELCFSQV IREGGHAVVWAGQLQGKLVAIKAFPPRSVAQFQAERALYELPGLQHDHIVRF ITASRGGPGRLLSGPLLVLELHPKGSLCHYLTQYTSDWGSSLRMALSLAQGL AFLHEERWQNGQYKPGIAHRDLSSQNVLIREDGSCAIGDLGLALVLPGLTQP PAWTPTQPQGPAAIMEAGTQRYMAPELLDKTLDLQDWGMALRRADIYSLALL LWEILSRCPDLRPDSSPPPFQLAYEAELGNTPTSDELWALAVQERRRPYIPS TWRCFATDPDGLRELLEDCWDADPEARLTAECVQQRLAALAHPQESHPFPES CPRGCPPLCPEDCTSIPAPTILPCRPQRSACHFSVQQGPCSRNPQPACTLSP V |
| 10 | rhAMHR2 | MPPNRRTCVFFEAPGVRGSTKTLGELLDTGTELPRAIRCLYSRCCFGIWNLT QDRAQVEMQGCRDSDEPGCESLHCDPSPRAHPSPGSTLFTCSCGTDFCNANY SHLPPPGSPGTPGSQGPQAAPG |
| 11 | human Anti-Müllerian Hormone Receptor II-Extracellular domain | PPNRRTCVFFEAPGVRGSTKTLGELLDTGTELPRAIRCLYSRCCFGIWNLTQ DRAQVEMQGCRDSDEPGCESLHCDPSPRAHPSPGSTLFTCSCGTDFCNANYS HLPPPGSPGTPGSQGPQAAPGESIWMAL |
| 12 | Residues 11-32 of AMHR2-ED and 28-49 of AMHR2 | EAPGVRGSTKTLGELLDTGTEL |
| 13 | Residues 20-26 of AMHR2-ED and 37-43 of AMHR2 | KTLGELL |
| 14 | Residues 22-26 of AMHR2-ED and 39-43 of AMHR2 | LGELL |

The invention claimed is:

1. An isolated antibody, wherein said antibody comprises a heavy chain comprising a variable heavy (VH) chain sequence comprising three heavy chain CDR sequences, CDR-H1, CDR-H2, and CDR-H3, and a light chain comprising a variable light (VL) chain sequence comprising three light chain CDR sequences, CDR-L1, CDR-L2, and CDR-L3, wherein a) CDR-H1 comprises the sequence shown in SEQ ID NO: 1, b) CDR-H2 comprises the sequence shown in SEQ ID NO: 2, c) CDR-H3 comprises the sequence shown in SEQ ID NO: 3, d) CDR-L1 comprises the sequence shown in SEQ ID NO: 4, e) CDR-L2 comprises the sequence shown in SEQ ID NO: 5, and f) CDR-L3 comprises the sequence shown in SEQ ID NO: 6.

2. The isolated antibody of claim 1, wherein the VH chain sequence comprises the sequence shown in SEQ ID NO: 7.

3. The isolated antibody of claim 1, wherein the VL chain sequence comprises the sequence show in SEQ ID NO: 8.

4. The isolated antibody of claim 1, wherein the antibody is a humanized or chimeric antibody.

5. The isolated antibody of claim 1, wherein the antibody is a monoclonal antibody.

6. A method of treating cancer in a subject in need thereof, comprising administering to the subject the anti-AMHR2 antibody of claim 1, wherein said subject has an AMHR2-expressing cancer.

7. The method of claim 6, wherein the antibody has antibody-dependent cell-mediated cytotoxicity (ADCC) activity, antibody-mediated cellular phagocytosis (ADCP) activity, and/or complement-dependent cytotoxicity (CDC) activity.

8. The method of claim 6, wherein the subject is human.

9. The method of claim 6, wherein the cancer is a solid cancer.

10. The method of claim 6, wherein the cancer is ovarian cancer.

11. The method of claim 10, wherein the ovarian cancer is stage I, stage IA, stage IB, stage IC, stage II, stage IIA, stage IIB, stage III, stage IIIA1, stage IIIA2, stage IIIB, stage IIIC, stage IV, stage IVA, or stage IVB ovarian cancer.

12. The method of claim 6, wherein the antibody is effective at reducing a cancer volume as compared to the cancer volume prior to administration of the antibody.

13. An isolated polynucleotide or set of polynucleotides encoding:

a) an antibody that comprises a heavy chain comprising a variable heavy (VH) chain sequence comprising three heavy chain CDR sequences, CDR-H1, CDR-H2, and CDR-H3, and a light chain comprising a variable light (VL) chain sequence comprising three light chain CDR sequences, CDR-L1, CDR-L2, and CDR-L3, wherein:

i) CDR-H1 comprises the sequence shown in SEQ ID NO: 1, ii) CDR-H2 comprises the sequence shown in SEQ ID NO: 2, iii) CDR-H3 comprises the sequence shown in SEQ ID NO: 3, iv) CDR-L1 comprises the sequence shown in SEQ ID NO: 4, v) CDR-L2 comprises the sequence shown in SEQ ID NO: 5, and iv) CDR-L3 comprises the sequence shown in SEQ ID NO: 6, b) a VH of said antibody, c) a VL of said antibody, d) a light chain of said antibody, e) a heavy chain of said antibody, or f) an antigen-binding portion of said antibody.

14. The isolated polynucleotide or set of polynucleotides of claim 13, wherein said isolated polynucleotide or set of polynucleotides comprise cDNA.

15. The isolated polynucleotide or set of polynucleotides of claim 13, wherein said isolated polynucleotide encodes said VH of said antibody.

16. The isolated polynucleotide or set of polynucleotides of claim 13, wherein said isolated polynucleotide encodes said VL of said antibody.

\* \* \* \* \*

SEQUENCE LISTING

<160> NUMBER OF SEQ ID NOS: 19

<210> SEQ ID NO 1
<211> LENGTH: 5
<212> TYPE: PRT
<213> ORGANISM: Artificial Sequence
<220> FEATURE:
<223> OTHER INFORMATION: Synthetic

<400> SEQUENCE: 1

Arg Tyr Phe Met Ser
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic

<400> SEQUENCE: 2

Ala Ile Asn Ser Asp Gly Gly Arg Thr Tyr Tyr Pro Asp Thr Val Lys
1               5                   10                  15

Gly

<210> SEQ ID NO 3
<211> LENGTH: 12
<212> TYPE: PRT
<213> ORGANISM: Artificial Sequence
<220> FEATURE:
<223> OTHER INFORMATION: Synthetic

<400> SEQUENCE: 3

His Ile Tyr Ser Tyr Tyr Glu Asp Tyr Phe Asp Tyr
1               5                   10

<210> SEQ ID NO 4
<211> LENGTH: 16
<212> TYPE: PRT
<213> ORGANISM: Artificial Sequence
<220> FEATURE:
<223> OTHER INFORMATION: Synthetic

<400> SEQUENCE: 4

Arg Ser Ser Gln Ser Leu Val His Ser Asn Gly Asn Thr Tyr Leu His
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Synthetic

<400> SEQUENCE: 5

Lys Val Ser Lys Arg Phe Ser
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Ser Gln Ser Thr His Val Tyr Thr
1               5

<210> SEQ ID NO 7
<211> LENGTH: 121
<212> TYPE: PRT
<213> ORGANISM: Artificial Sequence
<220> FEATURE:
<223> OTHER INFORMATION: Synthetic

<400> SEQUENCE: 7

Asp Val Lys Leu Val Glu Ser Gly Gly Gly Leu Val Lys Leu Gly Gly
1               5                   10                  15

Ser Leu Lys Leu Ser Cys Ala Ala Ser Gly Phe Thr Phe Ser Arg Tyr
            20                  25                  30

Phe Met Ser Trp Val Arg Gln Thr Pro Glu Lys Arg Leu Glu Leu Val
        35                  40                  45

Ala Ala Ile Asn Ser Asp Gly Gly Arg Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Leu Tyr Tyr Cys
                85                  90                  95

Thr Arg His Ile Tyr Ser Tyr Tyr Glu Asp Tyr Phe Asp Tyr Trp Gly
            100                 105                 110

Gln Gly Thr Thr Leu Thr Val Ser Ser
        115                 120

<210> SEQ ID NO 8
<211> LENGTH: 111
<212> TYPE: PRT
<213> ORGANISM: Artificial Sequence
<220> FEATURE:
<223> OTHER INFORMATION: Synthetic

<400> SEQUENCE: 8

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Tyr Thr Phe Gly Gly Gly Thr Lys Leu Glu Ile Lys
            100                 105                 110

<210> SEQ ID NO 9
<211> LENGTH: 573
<212> TYPE: PRT
<213> ORGANISM: Homo sapiens
<220> FEATURE:
<221> NAME/KEY: misc_feature
<223> OTHER INFORMATION: Full human Anti-Mullerian Hormone Receptor II
      protein

<400> SEQUENCE: 9

```
Met Leu Gly Ser Leu Gly Leu Trp Ala Leu Leu Pro Thr Ala Val Glu
1               5                   10                  15

Ala Pro Pro Asn Arg Arg Thr Cys Val Phe Phe Glu Ala Pro Gly Val
                20                  25                  30

Arg Gly Ser Thr Lys Thr Leu Gly Glu Leu Leu Asp Thr Gly Thr Glu
            35                  40                  45

Leu Pro Arg Ala Ile Arg Cys Leu Tyr Ser Arg Cys Cys Phe Gly Ile
    50                  55                  60

Trp Asn Leu Thr Gln Asp Arg Ala Gln Val Glu Met Gln Gly Cys Arg
65                  70                  75                  80

Asp Ser Asp Glu Pro Gly Cys Glu Ser Leu His Cys Asp Pro Ser Pro
                85                  90                  95

Arg Ala His Pro Ser Pro Gly Ser Thr Leu Phe Thr Cys Ser Cys Gly
            100                 105                 110

Thr Asp Phe Cys Asn Ala Asn Tyr Ser His Leu Pro Pro Pro Gly Ser
            115                 120                 125

Pro Gly Thr Pro Gly Ser Gln Gly Pro Gln Ala Ala Pro Gly Glu Ser
    130                 135                 140

Ile Trp Met Ala Leu Val Leu Leu Gly Leu Phe Leu Leu Leu Leu Leu
145                 150                 155                 160

Leu Leu Gly Ser Ile Ile Leu Ala Leu Leu Gln Arg Lys Asn Tyr Arg
                165                 170                 175

Val Arg Gly Glu Pro Val Pro Glu Pro Arg Pro Asp Ser Gly Arg Asp
            180                 185                 190

Trp Ser Val Glu Leu Gln Glu Leu Pro Glu Leu Cys Phe Ser Gln Val
            195                 200                 205

Ile Arg Glu Gly Gly His Ala Val Val Trp Ala Gly Gln Leu Gln Gly
    210                 215                 220

Lys Leu Val Ala Ile Lys Ala Phe Pro Pro Arg Ser Val Ala Gln Phe
225                 230                 235                 240

Gln Ala Glu Arg Ala Leu Tyr Glu Leu Pro Gly Leu Gln His Asp His
            245                 250                 255

Ile Val Arg Phe Ile Thr Ala Ser Arg Gly Gly Pro Gly Arg Leu Leu
            260                 265                 270

Ser Gly Pro Leu Leu Val Leu Glu Leu His Pro Lys Gly Ser Leu Cys
    275                 280                 285

His Tyr Leu Thr Gln Tyr Thr Ser Asp Trp Gly Ser Ser Leu Arg Met
    290                 295                 300

Ala Leu Ser Leu Ala Gln Gly Leu Ala Phe Leu His Glu Glu Arg Trp
305                 310                 315                 320

Gln Asn Gly Gln Tyr Lys Pro Gly Ile Ala His Arg Asp Leu Ser Ser
            325                 330                 335

Gln Asn Val Leu Ile Arg Glu Asp Gly Ser Cys Ala Ile Gly Asp Leu
            340                 345                 350

Gly Leu Ala Leu Val Leu Pro Gly Leu Thr Gln Pro Pro Ala Trp Thr
    355                 360                 365

Pro Thr Gln Pro Gln Gly Pro Ala Ala Ile Met Glu Ala Gly Thr Gln
    370                 375                 380

Arg Tyr Met Ala Pro Glu Leu Leu Asp Lys Thr Leu Asp Leu Gln Asp
385                 390                 395                 400

Trp Gly Met Ala Leu Arg Arg Ala Asp Ile Tyr Ser Leu Ala Leu Leu
            405                 410                 415
```

-continued

```
Leu Trp Glu Ile Leu Ser Arg Cys Pro Asp Leu Arg Pro Asp Ser Ser
            420             425             430

Pro Pro Pro Phe Gln Leu Ala Tyr Glu Ala Glu Leu Gly Asn Thr Pro
            435             440             445

Thr Ser Asp Glu Leu Trp Ala Leu Ala Val Gln Glu Arg Arg Arg Pro
            450             455             460

Tyr Ile Pro Ser Thr Trp Arg Cys Phe Ala Thr Asp Pro Asp Gly Leu
465             470             475             480

Arg Glu Leu Leu Glu Asp Cys Trp Asp Ala Asp Pro Glu Ala Arg Leu
            485             490             495

Thr Ala Glu Cys Val Gln Gln Arg Leu Ala Ala Leu Ala His Pro Gln
            500             505             510

Glu Ser His Pro Phe Pro Glu Ser Cys Pro Arg Gly Cys Pro Pro Leu
            515             520             525

Cys Pro Glu Asp Cys Thr Ser Ile Pro Ala Pro Thr Ile Leu Pro Cys
            530             535             540

Arg Pro Gln Arg Ser Ala Cys His Phe Ser Val Gln Gln Gly Pro Cys
545             550             555             560

Ser Arg Asn Pro Gln Pro Ala Cys Thr Leu Ser Pro Val
            565             570
```

```
<210> SEQ ID NO 10
<211> LENGTH: 126
<212> TYPE: PRT
<213> ORGANISM: Artificial Sequence
<220> FEATURE:
<223> OTHER INFORMATION: Synthetic

<400> SEQUENCE: 10

Met Pro Pro Asn Arg Arg Thr Cys Val Phe Phe Glu Ala Pro Gly Val
1               5               10              15

Arg Gly Ser Thr Lys Thr Leu Gly Glu Leu Leu Asp Thr Gly Thr Glu
            20              25              30

Leu Pro Arg Ala Ile Arg Cys Leu Tyr Ser Arg Cys Cys Phe Gly Ile
            35              40              45

Trp Asn Leu Thr Gln Asp Arg Ala Gln Val Glu Met Gln Gly Cys Arg
            50              55              60

Asp Ser Asp Glu Pro Gly Cys Glu Ser Leu His Cys Asp Pro Ser Pro
65              70              75              80

Arg Ala His Pro Ser Pro Gly Ser Thr Leu Phe Thr Cys Ser Cys Gly
            85              90              95

Thr Asp Phe Cys Asn Ala Asn Tyr Ser His Leu Pro Pro Pro Gly Ser
            100             105             110

Pro Gly Thr Pro Gly Ser Gln Gly Pro Gln Ala Ala Pro Gly
            115             120             125
```

```
<210> SEQ ID NO 11
<211> LENGTH: 132
<212> TYPE: PRT
<213> ORGANISM: Homo sapiens
<220> FEATURE:
<221> NAME/KEY: misc_feature
<223> OTHER INFORMATION: Human Anti-Mullerian Hormone Receptor
      II-Extracellular domain

<400> SEQUENCE: 11

Pro Pro Asn Arg Arg Thr Cys Val Phe Phe Glu Ala Pro Gly Val Arg
1               5               10              15
```

```
Gly Ser Thr Lys Thr Leu Gly Glu Leu Leu Asp Thr Gly Thr Glu Leu
            20                  25                  30

Pro Arg Ala Ile Arg Cys Leu Tyr Ser Arg Cys Cys Phe Gly Ile Trp
        35                  40                  45

Asn Leu Thr Gln Asp Arg Ala Gln Val Glu Met Gln Gly Cys Arg Asp
    50                  55                  60

Ser Asp Glu Pro Gly Cys Glu Ser Leu His Cys Asp Pro Ser Pro Arg
65                  70                  75                  80

Ala His Pro Ser Pro Gly Ser Thr Leu Phe Thr Cys Ser Cys Gly Thr
                85                  90                  95

Asp Phe Cys Asn Ala Asn Tyr Ser His Leu Pro Pro Pro Gly Ser Pro
            100                 105                 110

Gly Thr Pro Gly Ser Gln Gly Pro Gln Ala Ala Pro Gly Glu Ser Ile
        115                 120                 125

Trp Met Ala Leu
    130
```

<210> SEQ ID NO 12
<211> LENGTH: 22
<212> TYPE: PRT
<213> ORGANISM: Artificial Sequence
<220> FEATURE:
<223> OTHER INFORMATION: Synthetic

<400> SEQUENCE: 12

```
Glu Ala Pro Gly Val Arg Gly Ser Thr Lys Thr Leu Gly Glu Leu Leu
1                   5                   10                  15

Asp Thr Gly Thr Glu Leu
                20
```

<210> SEQ ID NO 13
<211> LENGTH: 7
<212> TYPE: PRT
<213> ORGANISM: Artificial Sequence
<220> FEATURE:
<223> OTHER INFORMATION: Synthetic

<400> SEQUENCE: 13

```
Lys Thr Leu Gly Glu Leu Leu
1                   5
```

<210> SEQ ID NO 14
<211> LENGTH: 5
<212> TYPE: PRT
<213> ORGANISM: Artificial Sequence
<220> FEATURE:
<223> OTHER INFORMATION: Synthetic

<400> SEQUENCE: 14

```
Leu Gly Glu Leu Leu
1                   5
```

<210> SEQ ID NO 15
<211> LENGTH: 12
<212> TYPE: PRT
<213> ORGANISM: Artificial Sequence
<220> FEATURE:
<223> OTHER INFORMATION: Synthetic

<400> SEQUENCE: 15

```
Arg Arg Thr Cys Val Phe Phe Glu Ala Pro Gly Val
1                   5                   10
```

-continued

```
<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Arg Ala Ile Arg Cys Leu Tyr Ser Arg
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic

<400> SEQUENCE: 17

Asp Arg Ala Gln Val Glu Met
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic

<400> SEQUENCE: 18

Gly Ile Trp Asn Leu
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic

<400> SEQUENCE: 19

Pro Ser Pro Gly Ser Thr Leu Phe Thr
1               5
```